United States Patent
Leung et al.

(10) Patent No.: US 8,183,346 B2
(45) Date of Patent: May 22, 2012

(54) ANTI-FERROPORTIN 1 MONOCLONAL ANTIBODIES AND USES THEREOF

(75) Inventors: Donmienne Doen Mun Leung, San Diego, CA (US); Peng Luan, Livermore, CA (US); Joseph Vincent Manetta, Indianapolis, IN (US); Ying Tang, San Diego, CA (US); Derrick Ryan Witcher, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 104 days.

(21) Appl. No.: 12/628,263

(22) Filed: Dec. 1, 2009

(65) Prior Publication Data

US 2011/0129480 A1 Jun. 2, 2011
US 2012/0100148 A9 Apr. 26, 2012

Related U.S. Application Data

(60) Provisional application No. 61/120,076, filed on Dec. 5, 2008, provisional application No. 61/239,818, filed on Sep. 4, 2009.

(51) Int. Cl.
*C07K 16/00* (2006.01)
*C07K 16/28* (2006.01)
*C07K 16/46* (2006.01)

(52) U.S. Cl. .............. 530/387.1; 530/387.3; 530/387.9; 530/388.2

(58) Field of Classification Search .................. None
See application file for complete search history.

(56) References Cited

U.S. PATENT DOCUMENTS

| 7,166,446 B2 | 1/2007 | Tekamp-Olson |
| 7,166,448 B1 | 1/2007 | Zon et al. |
| 7,521,055 B2 | 4/2009 | Zon et al. |
| 2008/0213277 A1 | 9/2008 | Sasu et al. |

FOREIGN PATENT DOCUMENTS

WO 2009094551 A1 7/2009

OTHER PUBLICATIONS

Beiboer et al., "Guided selection of a pan carcinoma specific antibody reveals similar binding characteristics yet structural divergence between the original murine antibody and its human equivalent" J. Mol Biol. (2000) 296: 833-849.*
Klimka et al., "Human anti-CD30 recombinant antibodies by duided phage antibody selection using cell panning" British Journal of Cancer (2000) 83: 252-260.*
Portolano et al., "Lack of promiscuity in autoantigen-specific H and L chain combinations as revealed by human H and L chain "Roulette"" (1993) 150(3): 880-887.*
Abboud, et al., "A Novel Mammalian Iron-regulated Protein Involved in Intracellular Iron Metabolism", The Journal of Biological Chemistry 275(26):19906-19912 (Jun. 30, 2000).
De Domenico, et al., "The Hepcidin-Binding Site on Ferroportin is Evolutionarily Conserved", Cell Metabolism 8:146-156 (Aug. 6, 2008).
Donovan, et al., "Positional cloning of zebrafish ferroportin1 identified a conserved vertebrate iron exporter", Nature 403:776-781 (Feb. 17, 2000).
Kong, et al al., "Effect of erythropoietin on hepcidin, DMT1 with IRE, and hephaestin gene expression in duodenum of rats", J Gastroenterol 43:136-143 (2008).
Liu, et al., "Functional consequences of ferroportin 1 mutations", Blood Cells, Molecules, and Diseases 35:33-46 (2005).
McKie, et al., "The SLC40 basolateral iron transporter family (IREG1/ferroportin/MTP1)", Eur J Physiol 447:801-806 (2004).
McKie, et al., "A Novel Duodenal Iron-Regulated Transporter, IREG1, Implicated in the Basolateral Transfer of Iron to the Circulation", Molecular Cell 5:299-309 (Feb. 2000).
Nemeth, et al., "Hepcidin Regulates Iron Efflux by Binding to Ferroportin and Inducing Its Internalization", Sciencexpress www.sciencexpress.org/ (Oct. 28, 2004).
Oates, et al al., "Augmented internalisation of ferroportin to late endosomes impairs iron uptake by enterocyte-like IEC-6 cells", Eur J Physiol 450:317-325 (2005).
Thomas, et al., "Ferroportin/IREG-1/MTP-1/SLC40A1 modulates the uptake of iron at the apical membrane of enterocytes", Gut 53:44-49 (2004).
Wallace, et al., "A novel mutation in ferroportin implicated in iron overload", Journal of Hepatology 46:921-926 (2007).
Young, et al., "Hepcidin for Clinicians", Clin J Am Soc Nephrol 4:1384-1387 (2009).
Nemeth, et al., "Regulation of iron metabolism by hepcidin," Annual Review of Nutrition, 26:323-342 (2006).
Dunn, et al., "Iron uptake and metabolism in the new millennium," Trends in Cell Biology, Elsevier Science Ltd., 17(2): 93-100 (Feb. 6, 2007).

* cited by examiner

*Primary Examiner* — Maher Haddad
*Assistant Examiner* — James Rogers
(74) *Attorney, Agent, or Firm* — Robert L. Sharp

(57) ABSTRACT

Provided are monoclonal antibodies and antigen-binding fragments thereof that bind to, and inhibit the activity of human FPN1, and which are effective in maintaining or increasing the transport of iron out of mammalian cells and/or maintaining or increasing the level of serum iron, reticulocyte count, red blood cell count, hemoglobin, and/or hematocrit in a subject in vivo.

7 Claims, 11 Drawing Sheets

Mab 34A9

- ← FpnE3a:    GGSPFEDIRSRFIQGESITPTKGC
- ← 060719Z:   GGSPFEDIRSRFIQGC
- ← 060719Y:   GGIQGESITPTKIPEITTEGC
- ← 0708L4A:   GGMPGSPLDLSVSPFEDGC
- ← 0708L4B:   GGSPLDLSVSPFEDIRSGC
- ← 0708L4C:   GGEDIRSRFIQGESITGC
- ← 0708L4D:   GGRSRFIQGESITPTKGC

FIGURE 1

A. Amino acid sequence of human light chain framework
O2 with interspersed CDR residues

FRL1 (SEQ ID NO: 74)        FRL2 (SEQ ID NO: 75)
                  LCDR1                          LCDR2
DIQMTQSPSSLSASVGDRVTITCXXXXXXXXXXXWYQQKPGKAPKLLIYXXXXXXX

FRL3 (SEQ ID NO: 76)          FRL4 (SEQID NO:77)
                            LCDR3
GVPSRFSGSGSGTDFTLTISSLQPEDFATYYCXXXXXXXXXFGGGTKVEIK

B. Amino acid sequence of a human heavy chain framework
VH1-69 with interspersed CDR residues

FRH1 (SEQ ID NO: 78)       FRH2 (SEQ ID NO: 79)
                          HCDR1
QVQLVQSGAEVKKPGSSVKVSCKASXXXXXXXXXXXWVRQAPGQGLEWMG

FRH3 (SEQ ID NO: 80)
   HCDR2
XXXXXXXXXXXXXXXXXXRVTITADKSTSTAYMELSSLRSEDTAVYYCAR

FRH4 (SEQ ID NO: 81)
HCDR3
XXXXXWGQGTTVTVSS

FIGURE 2

A. Amino acid sequence of human light chain framework O18 with interspersed CDR residues

FRL1 (SEQ ID NO: 74)    FRL2 (SEQ ID NO: 75)
                    LCDR1                              LCDR2
DIQMTQSPSSLSASVGDRVTITCXXXXXXXXXXXWYQQKPGKAPKLLIYXXXXXXX

FRL3 (SEQ ID NO: 82)         FRL4 (SEQID NO:77)
                        LCDR3
GVPSRFSGSGSGTDFTFTISSLQPEDIATYYCXXXXXXXXXFGGGTKVEIK

B. Amino acid sequence of a human heavy chain framework VH1-18 with interspersed CDR residues

FRH1 (SEQ ID NO: 83)        FRH2 (SEQ ID NO: 79)
                        HCDR1
QVQLVQSGAEVKKPGASVKVSCKASXXXXXXXXXXXWVRQAPGQGLEWMG

FRH3 (SEQ ID NO: 84)
    HCDR2
XXXXXXXXXXXXXXXXXRVTMTTDTSTSTAYMELRSLRSD**DTAVYYCAR

FRH4 (SEQ ID NO: 81)
    HCDR3
XXXXXWGQGTTVTVSS

FIGURE 3

A. Amino acid sequence of human light chain framework L12 with interspersed CDR residues

FRL1 (SEQ ID NO: 85)　　　　　　　　　FRL2 (SEQ ID NO: 75)
　　　　　　　　　　　　　　LCDR1　　　　　　　　　　　　　　　LCDR2
DIQMTQSPSTLSASVGDRVTITCXXXXXXXXXXXWYQQKPGKAPKLLIYXXXXXXX

FRL3 (SEQ ID NO: 86)　　　　　　　　FRL4 (SEQID NO:77)
　　　　　　　　　　　　　LCDR3
GVPSRFSGSGSGTEFTLTISSLQPDDFATYYCXXXXXXXXXFGGGTKVEIK

B. Amino acid sequence of a human heavy chain framework VH1-46 with interspersed CDR residues

FRH1 (SEQ ID NO: 83)　　　　　　　　　FRH2 (SEQ ID NO: 79)
　　　　　　　　　　　　　HCDR1
QVQLVQSGAEVKKPGASVKVSCKASXXXXXXXXXXXWVRQAPGQGLEWMG

FRH3 (SEQ ID NO: 87)
　HCDR2
XXXXXXXXXXXXXXXXRVTMTRDTSTSTVYMELSSLRSEDTAVYYCAR

FRH4 (SEQ ID NO: 81)
HCDR3
XXXXXWGQGTTVTVSS

FIGURE 4

Amino acid sequence of human light chain framework L1 with interspersed CDR residues

FRL1 (SEQ ID NO: 74)            FRL2 (SEQ ID NO: 168)
                      LCDR1                     LCDR2
DIQMTQSPSSLSASVGDRVTITCXXXXXXXXXXXWFQQKPGKAPKSLIYXXXXXXX

FRL3 (SEQ ID NO: 76)              FRL4
                                  (SEQID NO:169)
                             LCDR3
GVPSRFSGSGSGTDFTLTISSLQPEDFATYYCXXXXXXXXXFGQGTKLEIK

FIGURE 5

```
1    1F8
2    Combi11
3    Com11GY
4    1B7
5    3D8
6    4A10-3
7    L2.2-4
8    Consensus*

1    QVQLVQSGAEVKKPGSSVKVSCKASGYRFTSFLIEWVRQAPGQGLEWMGT
2    ................................A................
3    ................................A................
4    ..................................................
5    ..........................................A.......
6    ............................................A.....
7    ............................................A.....
8    ........................................X1........

1    SNPRTGRTKYKTKFRGRVTITADKSTSTAYMELSSLRSEDTAVYYCAREF
2    ...........S......................................
3    ......G....S......................................
4    ......G....E......................................
5    ......G....E......................................
6    ......GR...E......................................
7    ......GR...E......................................
8    ......X2X3...X4...................................

1    FDYWGQGTTVTVSS  (SEQ ID NO: 142)
2    ..............  (SEQ ID NO: 130)
3    ..............  (SEQ ID NO: 178)
4    .V............  (SEQ ID NO: 146)
5    ..............  (SEQ ID NO: 46)
6    ..............  (SEQ ID NO: 134)
7    ..............  (SEQ ID NO: 138)
8    .X5...........  (SEQ ID NO: 56)
```

```
1    1F8
2    Combi11
3    Com11GY
4    1B7
5    3D8
6    4A10-3
7    L2.2-4
8    Consensus*
```

```
1    DIQMTQSPSSLSASVGDRVTITCRASKSISKYTAWYQQKPGKAPKLLIYA
2    .................................................
3    .................................................
4    .................................................
5    .................................................
6    .................................................
7    .................................................
8    .................................................
```

```
1    GSKRYYGVPSRFSGSGSGTDFTLTISSLQPEDFATYYCQQHNEYPYTFGG
2    ....HW...........................................
3    ....H............................................
4    ....Y............................................
5    ...LHS...........................................
6    ...LHW...........................................
7    ...LRS...........................................
8    ...X₆X₇X₈........................................
```

```
1    GTKVEIK  (SEQ ID NO: 144)
2    .......  (SEQ ID NO: 132)
3    .......  (SEQ ID NO: 180)
4    .......  (SEQ ID NO: 148)
5    .......  (SEQ ID NO:  49)
6    .......  (SEQ ID NO: 136)
7    .......  (SEQ ID NO: 140)
8    .......  (SEQ ID NO:  57)
```

*$X_6$ is L or R; $X_7$ is H, R or Y; and $X_8$ is S, W, or Y.

SEQUENCE LISTING

<160> NUMBER OF SEQ ID NOS: 214

<210> SEQ ID NO 1
<211> LENGTH: 571
<212> TYPE: PRT
<213> ORGANISM: Homo sapiens

<400> SEQUENCE: 1

```
Met Thr Arg Ala Gly Asp His Asn Arg Gln Arg Gly Cys Cys Gly Ser
1               5                   10                  15

Leu Ala Asp Tyr Leu Thr Ser Ala Lys Phe Leu Leu Tyr Leu Gly His
            20                  25                  30

Ser Leu Ser Thr Trp Gly Asp Arg Met Trp His Phe Ala Val Ser Val
        35                  40                  45

Phe Leu Val Glu Leu Tyr Gly Asn Ser Leu Leu Leu Thr Ala Val Tyr
    50                  55                  60

Gly Leu Val Val Ala Gly Ser Val Leu Val Leu Gly Ala Ile Ile Gly
65                  70                  75                  80

Asp Trp Val Asp Lys Asn Ala Arg Leu Lys Val Ala Gln Thr Ser Leu
                85                  90                  95

Val Val Gln Asn Val Ser Val Ile Leu Cys Gly Ile Ile Leu Met Met
            100                 105                 110

Val Phe Leu His Lys His Glu Leu Leu Thr Met Tyr His Gly Trp Val
        115                 120                 125

Leu Thr Ser Cys Tyr Ile Leu Ile Ile Thr Ile Ala Asn Ile Ala Asn
    130                 135                 140

Leu Ala Ser Thr Ala Thr Ala Ile Thr Ile Gln Arg Asp Trp Ile Val
145                 150                 155                 160

Val Val Ala Gly Glu Asp Arg Ser Lys Leu Ala Asn Met Asn Ala Thr
                165                 170                 175

Ile Arg Arg Ile Asp Gln Leu Thr Asn Ile Leu Ala Pro Met Ala Val
            180                 185                 190
```

```
Gly Gln Ile Met Thr Phe Gly Ser Pro Val Ile Gly Cys Gly Phe Ile
        195                 200                 205

Ser Gly Trp Asn Leu Val Ser Met Cys Val Glu Tyr Val Leu Leu Trp
210                 215                 220

Lys Val Tyr Gln Lys Thr Pro Ala Leu Ala Val Lys Ala Gly Leu Lys
225                 230                 235                 240

Glu Glu Glu Thr Glu Leu Lys Gln Leu Asn Leu His Lys Asp Thr Glu
            245                 250                 255

Pro Lys Pro Leu Glu Gly Thr His Leu Met Gly Val Lys Asp Ser Asn
                260                 265                 270

Ile His Glu Leu Glu His Glu Gln Glu Pro Thr Cys Ala Ser Gln Met
        275                 280                 285

Ala Glu Pro Phe Arg Thr Phe Arg Asp Gly Trp Val Ser Tyr Tyr Asn
290                 295                 300

Gln Pro Val Phe Leu Ala Gly Met Gly Leu Ala Phe Leu Tyr Met Thr
305                 310                 315                 320

Val Leu Gly Phe Asp Cys Ile Thr Thr Gly Tyr Ala Tyr Thr Gln Gly
            325                 330                 335

Leu Ser Gly Ser Ile Leu Ser Ile Leu Met Gly Ala Ser Ala Ile Thr
                340                 345                 350

Gly Ile Met Gly Thr Val Ala Phe Thr Trp Leu Arg Arg Lys Cys Gly
        355                 360                 365

Leu Val Arg Thr Gly Leu Ile Ser Gly Leu Ala Gln Leu Ser Cys Leu
370                 375                 380

Ile Leu Cys Val Ile Ser Val Phe Met Pro Gly Ser Pro Leu Asp Leu
385                 390                 395                 400

Ser Val Ser Pro Phe Glu Asp Ile Arg Ser Arg Phe Ile Gln Gly Glu
            405                 410                 415

Ser Ile Thr Pro Thr Lys Ile Pro Glu Ile Thr Thr Glu Ile Tyr Met
                420                 425                 430

Ser Asn Gly Ser Asn Ser Ala Asn Ile Val Pro Glu Thr Ser Pro Glu
        435                 440                 445

Ser Val Pro Ile Ile Ser Val Ser Leu Leu Phe Ala Gly Val Ile Ala
450                 455                 460

Ala Arg Ile Gly Leu Trp Ser Phe Asp Leu Thr Val Thr Gln Leu Leu
465                 470                 475                 480

Gln Glu Asn Val Ile Glu Ser Glu Arg Gly Ile Ile Asn Gly Val Gln
            485                 490                 495

Asn Ser Met Asn Tyr Leu Leu Asp Leu Leu His Phe Ile Met Val Ile
                500                 505                 510

Leu Ala Pro Asn Pro Glu Ala Phe Gly Leu Leu Val Leu Ile Ser Val
        515                 520                 525

Ser Phe Val Ala Met Gly His Ile Met Tyr Phe Arg Phe Ala Gln Asn
530                 535                 540

Thr Leu Gly Asn Lys Leu Phe Ala Cys Gly Pro Asp Ala Lys Glu Val
545                 550                 555                 560

Arg Lys Glu Asn Gln Ala Asn Thr Ser Val Val
            565                 570

<210> SEQ ID NO 2
<211> LENGTH: 1716
<212> TYPE: DNA
<213> ORGANISM: Homo sapiens
```

```
<400> SEQUENCE: 2
atgaccaggg cgggagatca caaccgccag agaggatgct gtggatcctt ggccgactac    60
ctgacctctg caaaattcct tctctacctt ggtcattctc tctctacttg gggagatcgg   120
atgtggcact ttgcggtgtc tgtgtttctg gtagagctct atggaaacag cctccttttg   180
acagcagtct acgggctggt ggtggcaggg tctgttctgg tcctgggagc catcatcggt   240
gactgggtgg acaagaatgc tagacttaaa gtgcccagaa cctcgctggt ggtacagaat   300
gtttcagtca tcctgtgtgg aatcatcctg atgatggttt tcttacataa acatgagctt   360
ctgaccatgt accatggatg ggttctcact tcctgctata tcctgatcat cactattgca   420
aatattgcaa atttggccag tactgctact gcaatcacaa tccaaaggga ttggattgtt   480
gttgttgcag gagaagacag aagcaaacta gcaaatatga atgccacaat acgaaggatt   540
gaccagttaa ccaacatctt agcccccatg gctgttggcc agattatgac atttggctcc   600
ccagtcatcg gctgtggctt tatttcggga tggaacttgg tatccatgtg cgtggagtac   660
gttctgctct ggaaggttta ccagaaaacc ccagctctag ctgtgaaagc tggtcttaaa   720
gaagaggaaa ctgaattgaa acagctgaat ttacacaaag atactgagcc aaaacccctg   780
gagggaactc atctaatggg tgtgaaagac tctaacatcc atgagcttga acatgagcaa   840
gagcctactt gtgcctccca gatggctgag ccctttccgta ccttccgaga tggatgggtc   900
tcctactaca ccagcctgt gtttctggct ggcatgggtc ttgctttcct ttatatgact   960
gtcctgggct ttgactgcat caccacaggg tacgcctaca ctcagggact gagtggttcc  1020
atcctcagta ttttgatggg agcatcagct ataactggaa taatgggaac tgtagctttt  1080
acttggctac gtcgaaaatg tggtttggtt cggacaggtc tgatctcagg attggcacag  1140
cttttcctgt tgatcttgtg tgtgatctct gtattcatgc ctggaagccc cctggacttg  1200
tccgtttctc cttttgaaga tatccgatca aggttcattc aaggagagtc aattacacct  1260
accaagatac ctgaaattac aactgaaata tacatgtcta atgggtctaa ttctgctaat  1320
attgtcccgg agacaagtcc tgaatctgtg cccataatct ctgtcagtct gctgtttgca  1380
ggcgtcattg ctgctagaat cggtctttgg tcctttgatt taactgtgac acagttgctg  1440
caagaaaatg taattgaatc tgaaagaggc attataaatg gtgtacagaa ctccatgaac  1500
tatcttcttg atcttctgca tttcatcatg gtcatcctgg ctccaaatcc tgaagctttt  1560
ggcttgctcg tattgatttc agtctccttt gtggcaatgg ccacattat gtatttccga  1620 tttgcccaaa atactctggg aaacaagctc tttgcttgcg gtcctgatgc aaaagaagtt  1680
aggaaggaaa atcaagcaaa tacatctgtt gtgtag                            1716

<210> SEQ ID NO 3
<211> LENGTH: 573
<212> TYPE: PRT
<213> ORGANISM: Macaca irus

<400> SEQUENCE: 3

Met Thr Arg Ala Gly Asp His Asn Arg Gln Arg Gly Cys Cys Gly Ser
1               5                   10                  15

Leu Ala Asp Tyr Leu Thr Ser Ala Lys Phe Leu Leu Tyr Leu Gly His
            20                  25                  30

Ser Leu Ser Thr Trp Gly Asp Arg Met Trp His Phe Ala Val Ser Val
        35                  40                  45

Phe Leu Val Glu Leu Tyr Gly Asn Ser Leu Leu Leu Thr Ala Val Tyr
    50                  55                  60
```

```
Gly Leu Val Val Ala Gly Ser Val Leu Val Leu Gly Ala Ile Ile Gly
 65                  70                  75                  80

Asp Trp Val Asp Lys Asn Ala Arg Leu Lys Val Ala Gln Thr Ser Leu
                 85                  90                  95

Val Val Gln Asn Val Ser Val Ile Leu Cys Gly Ile Ile Leu Met Met
            100                 105                 110

Val Phe Leu His Lys His Glu Leu Leu Thr Met Tyr His Gly Trp Val
        115                 120                 125

Leu Thr Ser Cys Tyr Ile Leu Ile Thr Ile Ala Asn Ile Ala Asn
    130                 135                 140

Leu Ala Ser Thr Ala Thr Ala Ile Thr Ile Gln Arg Asp Trp Ile Val
145                 150                 155                 160

Val Val Ala Gly Glu Asp Arg Ser Lys Leu Ala Asn Met Asn Ala Thr
                165                 170                 175

Ile Arg Arg Ile Asp Gln Leu Thr Asn Ile Leu Ala Pro Met Ala Val
            180                 185                 190

Gly Gln Ile Met Thr Phe Gly Ser Pro Val Ile Gly Cys Gly Phe Ile
        195                 200                 205

Ser Gly Trp Asn Leu Val Ser Met Cys Val Glu Tyr Phe Leu Leu Trp
210                 215                 220

Lys Val Tyr Gln Lys Thr Pro Ala Leu Ala Val Lys Ala Ala Phe Lys
225                 230                 235                 240

Glu Glu Glu Thr Glu Leu Lys Gln Leu Asn Leu His Lys Asp Thr Glu
                245                 250                 255

Pro Lys Pro Leu Glu Gly Thr His Leu Met Gly Val Lys Asp Ser Asn
            260                 265                 270

Ile His Glu Leu Glu His Glu Gln Glu Pro Thr Cys Ala Ser Gln Met
        275                 280                 285

Ala Glu Pro Phe Arg Thr Phe Arg Asp Gly Trp Val Ser Tyr Tyr Asn
    290                 295                 300

Gln Pro Val Phe Leu Ala Gly Met Gly Leu Ala Phe Leu Tyr Met Thr
305                 310                 315                 320

Val Leu Gly Phe Asp Cys Ile Thr Thr Gly Tyr Ala Tyr Thr Gln Gly
                325                 330                 335

Leu Ser Gly Ser Ile Leu Ser Ile Leu Met Gly Ala Ser Ala Ile Thr
            340                 345                 350

Gly Ile Met Gly Thr Val Ala Phe Thr Trp Leu Arg Arg Lys Cys Gly
        355                 360                 365

Leu Val Arg Thr Gly Leu Ile Ser Gly Leu Ala Gln Leu Ser Cys Leu
    370                 375                 380

Ile Leu Cys Val Ile Ser Val Phe Met Pro Gly Ser Pro Leu Asp Leu
385                 390                 395                 400

Ser Val Ser Pro Phe Glu Asp Ile Arg Ser Arg Phe Ile Gln Gly Glu
                405                 410                 415

Ser Ile Thr Pro Thr Lys Ile Pro Glu Thr Ile Thr Thr Glu Ile
            420                 425                 430

Tyr Met Ser Asn Gly Ser Asn Ser Ala Asn Ile Val Pro Glu Thr Ser
        435                 440                 445

Pro Glu Ser Val Pro Ile Ile Ser Val Ser Leu Leu Phe Ala Gly Val
    450                 455                 460

Ile Ala Ala Arg Ile Gly Leu Trp Ser Phe Asp Leu Thr Val Thr Gln
465                 470                 475                 480

Leu Leu Gln Glu Asn Val Ile Glu Ser Glu Arg Gly Ile Ile Asn Gly
                485                 490                 495
```

Val Gln Asn Ser Met Asn Tyr Leu Leu Asp Leu Leu His Phe Ile Met
            500                 505                 510

Val Ile Leu Ala Pro Asn Pro Glu Ala Phe Gly Leu Leu Val Leu Ile
        515                 520                 525

Ser Val Ser Phe Val Ala Met Gly His Ile Met Tyr Phe Arg Phe Ala
    530                 535                 540

His Asn Thr Leu Gly Asn Lys Leu Phe Ala Cys Gly Pro Asp Ala Lys
545                 550                 555                 560

Glu Val Arg Lys Glu Asn Gln Ala Asn Thr Ser Val Val
                565                 570

<210> SEQ ID NO 4
<211> LENGTH: 1320
<212> TYPE: DNA
<213> ORGANISM: Artificial
<220> FEATURE:
<223> OTHER INFORMATION: Synthetic

<400> SEQUENCE: 4
caggtgcagc tggtgcagtc tggggctgag gtgaagaagc ctgggtcctc agtgaaggtt      60
tcctgcaagg catctggcta cgccttcact tcgttcttga tagagtgggt gcgacaggcc     120
cctggacaag gccttgagtg gatgggaacg agtaatccta ggactgggag acgaagtat      180 aaatccaagt tcaggggcag agtcaccatt accgcggaca atccacgag cacagcctac     240 atggagctga gcagcctgag atctgaggac acggccgtgt attactgtgc gcgcgagttt     300
tttgactact ggggccaagg aaccacggtc accgtctcct cagcctccac caagggccca     360
tcggtcttcc cgctagcgcc ctgctccagg agcacctccg agagcacagc cgccctgggc     420
tgcctggtca aggactactt ccccgaaccg gtgacggtgt cgtggaactc aggcgccctg     480
accagcggcg tgcacacctt cccggctgtc ctacagtcct caggactcta ctccctcagc     540
agcgtggtga ccgtgccctc agcagcttg gcacgaaga cctacacctg caacgtagat     600
cacaagccca gcaacaccaa ggtggacaag agagttgagt ccaaatatgg tcccccatgc     660
ccaccctgcc cagcacctga gccgccggg ggaccatcag tcttcctgtt ccccccaaaa     720
cccaaggaca ctctcatgat ctcccggacc cctgaggtca cgtgcgtggt ggtggacgtg     780
agccaggaag acccccgaggt ccagttcaac tggtacgtgg atggcgtgga ggtgcataat     840
gccaagacaa agccgcggga ggagcagttc aacagcacgt accgtgtggt cagcgtcctc     900
accgtcctgc accaggactg gctgaacggc aaggagtaca agtgcaaggt ctccaacaaa     960
ggcctcccgt cctccatcga gaaaaccatc tccaaagcca agggcagcc cgagagcca     1020 caggtgtaca ccctgccccc atcccaggag gagatgacca gaaccaggt cagcctgacc     1080 tgcctggtca aaggcttcta ccccagcgac atcgccgtgg agtgggaaag caatgggcag     1140
ccggagaaca actacaagac cacgcctccc gtgctggact ccgacggctc cttcttcctc     1200
tacagcaggc taaccgtgga caagagcagg tggcaggagg ggaatgtctt ctcatgctcc     1260
gtgatgcatg aggctctgca caaccactac acacagaaga gcctctccct gtctctgggt     1320

<210> SEQ ID NO 5
<211> LENGTH: 570
<212> TYPE: PRT
<213> ORGANISM: Rattus sp

<400> SEQUENCE: 5

Met Thr Lys Ser Arg Asp Gln Thr His Gln Glu Gly Cys Cys Gly Ser
1               5                   10                  15

```
Leu Ala Asn Tyr Leu Thr Ser Ala Lys Phe Leu Leu Tyr Leu Gly His
             20                  25                  30

Ser Leu Ser Thr Trp Gly Asp Arg Met Trp His Phe Ala Val Ser Val
         35                  40                  45

Phe Leu Val Glu Leu Tyr Gly Asn Ser Leu Leu Leu Thr Ala Val Tyr
 50                  55                  60

Gly Leu Val Val Ala Gly Ser Val Leu Val Leu Gly Ala Ile Ile Gly
 65                  70                  75                  80

Asp Trp Val Asp Lys Asn Ala Arg Leu Lys Val Ala Gln Thr Ser Leu
                 85                  90                  95

Val Val Gln Asn Val Ser Val Ile Leu Cys Gly Ile Ile Leu Met Met
            100                 105                 110

Val Phe Leu His Lys Asn Glu Leu Leu Asn Met Tyr His Gly Trp Val
        115                 120                 125

Leu Thr Val Cys Tyr Ile Leu Ile Ile Thr Ile Ala Asn Ile Ala Asn
130                 135                 140

Leu Ala Ser Thr Ala Thr Ala Ile Thr Ile Gln Arg Asp Trp Ile Val
145                 150                 155                 160

Val Val Ala Gly Glu Asn Arg Ser Arg Leu Ala Asp Met Asn Ala Thr
                165                 170                 175

Ile Arg Arg Ile Asp Gln Leu Thr Asn Ile Leu Ala Pro Met Ala Val
            180                 185                 190

Gly Gln Ile Met Thr Phe Gly Ser Pro Val Ile Gly Cys Gly Phe Ile
        195                 200                 205

Ser Gly Trp Asn Leu Val Ser Met Cys Val Glu Tyr Phe Leu Leu Trp
210                 215                 220

Lys Val Tyr Gln Lys Thr Pro Ala Leu Ala Val Lys Ala Ala Leu Lys
225                 230                 235                 240

Val Glu Glu Ser Glu Leu Lys Gln Leu Thr Ser Pro Lys Asp Thr Glu
                245                 250                 255

Pro Lys Pro Leu Glu Gly Thr His Leu Met Gly Glu Lys Asp Ser Asn
            260                 265                 270

Ile Arg Glu Leu Glu Cys Glu Gln Glu Pro Thr Cys Ala Ser Gln Ile
        275                 280                 285

Ala Glu Pro Phe Arg Thr Phe Arg Asp Gly Trp Val Ser Tyr Tyr Asn
290                 295                 300

Gln Pro Val Phe Leu Ala Gly Met Gly Leu Ala Phe Leu Tyr Met Thr
305                 310                 315                 320

Val Leu Gly Phe Asp Cys Ile Thr Thr Gly Tyr Ala Tyr Thr Gln Gly
                325                 330                 335

Leu Ser Gly Ser Ile Leu Ser Val Leu Met Gly Ala Ser Ala Ile Thr
            340                 345                 350

Gly Ile Met Gly Thr Val Ala Phe Thr Trp Leu Arg Arg Lys Cys Gly
        355                 360                 365

Leu Val Arg Thr Gly Leu Phe Ser Gly Leu Ala Gln Leu Ser Cys Leu
370                 375                 380

Ile Leu Cys Val Ile Ser Val Phe Met Pro Gly Ser Pro Leu Asp Leu
385                 390                 395                 400

Ser Val Ser Pro Phe Glu Asp Ile Arg Ser Arg Phe Ile His Glu Glu
                405                 410                 415

Ala Val Ser Ser Thr Thr Lys Ile Pro Glu Thr Glu Met Leu Met Ser
            420                 425                 430

Asn Val Ser Asn Val Val Asn Thr Val His Glu Met Ser Thr Lys Ser
```

```
                435                 440                 445
Val Pro Ile Ile Ser Val Ser Leu Leu Phe Ala Gly Val Ile Ala Ala
    450                 455                 460

Arg Ile Gly Leu Trp Ser Phe Asp Leu Thr Val Thr Gln Leu Leu Gln
465                 470                 475                 480

Glu Asn Val Ile Glu Ser Glu Arg Gly Ile Ile Asn Gly Val Gln Asn
                485                 490                 495

Ser Met Asn Tyr Leu Leu Asp Leu Leu His Phe Ile Met Val Ile Leu
                500                 505                 510

Ala Pro Asn Pro Glu Ala Phe Gly Leu Leu Val Leu Ile Ser Val Ser
                515                 520                 525

Phe Val Ala Met Gly His Leu Met Tyr Phe Arg Phe Ala Gln Lys Thr
            530                 535                 540

Leu Gly Asn Gln Ile Phe Val Cys Ala Pro Asp Glu Lys Glu Val Thr
545                 550                 555                 560

Asp Glu Ser Gln Pro Asn Thr Ser Val Val
                565                 570

<210> SEQ ID NO 6
<211> LENGTH: 1713
<212> TYPE: DNA
<213> ORGANISM: Rattus sp

<400> SEQUENCE: 6
atgaccaagt caagagatca gacccatcag gaaggatgct gtggatcttt agcaaactac      60
ctgacctcag caaaattcct cctctacctt ggccactctc tctccacttg gggggatcgg     120
atgtggcact ttgcagtgtc tgtgtttctg gtggaactct acggaaacag cctcctcttg     180
acagctgtct acgggttggt ggtggcaggc tctgttctgg tcctgggagc catcattggt     240
gactgggtgg ataagaatgc cagacttaaa gtgcccagag cgtccctggt ggttcagaat     300
gtatcagtca ttctctgcgg gatcatcctg atgatggttt tcttacacaa gaatgagctt     360
ctgaacatgt atcatggatg gtccttact gtctgctaca tcctgatcat caccattgca     420
aacattgcga atttggccag tactgccact gcaattacaa tccaaaggga ctggattgtt     480
gtcgtagcag agaaaacag gagcagatta gcagacatga atgctaccat tagaaggatt     540
gaccagctaa ccaacatcct ggcccccatg gctgttggcc agattatgac attcggttcc     600
ccagtcattg gctgtggttt catttctggt tggaatttgg tgtccatgtg tgtggagtac     660
ttcttgctct ggaaggttta ccagaagacc ctgctctgg ctgtaaaagc tgctctcaag     720
gtagaggagt cagaactgaa gcagctgacc tcacctaaag atactgagcc aaaaccttg     780 gagggaactc acctaatggg tgagaaagac tctaacatcc gtgaacttga atgtgaacaa     840
gaacccacct gtgcctccca gatcgcagaa cccttccgca cttttcgaga tggatgggtc     900
tcctactata accagcccgt attttttggct ggcatgggcc tggctttcct ctatatgaca     960
gtcctgggct tcgactgtat caccacagga tatgcttaca ctcagggact gagtggttcc    1020
atcctcagtg ttttgatggg agcatcagca ataactggaa taatgggaac ctgtgccttc    1080
acttggctac gtcgaaaatg tggccttgtt cggactggtc tgttctcagg actggctcag    1140
ctttcttgtt tgatccttgtg tgtgatctcc gtgttcatgc ctggaagccc cttgacctg    1200 tctgtttctc catttgaaga tatccgttct aggtttatac atgaggaggc agtgtcctca    1260
actaccaaaa tacctgaaac agaaatgctt atgtctaatg tgtctaatgt tgtcaatacc    1320
gtccatgaga tgagtactaa atccgtcccc ataatctccg tcagcctgct gtttgcagga    1380
```

```
gtcattgctg ctagaatcgg tctttggtcc tttgatttga ctgtgacaca gttgctgcaa    1440
gaaaatgtaa ttgaatcaga aagaggcatt atcaatggtg tgcagaactc catgaactac    1500
cttctcgacc ttctgcattt catcatggtc atcttggccc caaatcctga agcttttggc    1560
ttgctagtat tgatttcagt ctcctttgtg gcaatgggac atcttatgta tttccgtttt    1620
gcccagaaga ctctgggcaa ccagattttt gtttgtgctc ctgatgaaaa ggaagttaca    1680
gatgaaagtc agcctaatac atctgttgtg tag                                 1713
```

<210> SEQ ID NO 7
<211> LENGTH: 570
<212> TYPE: PRT
<213> ORGANISM: Mus sp

<400> SEQUENCE: 7

```
Met Thr Lys Ala Arg Asp Gln Thr His Gln Glu Gly Cys Cys Gly Ser
1               5                   10                  15

Leu Ala Asn Tyr Leu Thr Ser Ala Lys Phe Leu Leu Tyr Leu Gly His
            20                  25                  30

Ser Leu Ser Thr Trp Gly Asp Arg Met Trp His Phe Ala Val Ser Val
        35                  40                  45

Phe Leu Val Glu Leu Tyr Gly Asn Ser Leu Leu Leu Thr Ala Val Tyr
    50                  55                  60

Gly Leu Val Val Ala Gly Ser Val Leu Val Leu Gly Ala Ile Ile Gly
65                  70                  75                  80

Asp Trp Val Asp Lys Asn Ala Arg Leu Lys Val Ala Gln Thr Ser Leu
                85                  90                  95

Val Val Gln Asn Val Ser Val Ile Leu Cys Gly Ile Ile Leu Met Met
            100                 105                 110

Val Phe Leu His Lys Asn Glu Leu Leu Thr Met Tyr His Gly Trp Val
        115                 120                 125

Leu Thr Val Cys Tyr Ile Leu Ile Ile Thr Ile Ala Asn Ile Ala Asn
    130                 135                 140

Leu Ala Ser Thr Ala Thr Ala Ile Thr Ile Gln Arg Asp Trp Ile Val
145                 150                 155                 160

Val Val Ala Gly Glu Asn Arg Ser Arg Leu Ala Asp Met Asn Ala Thr
                165                 170                 175

Ile Arg Arg Ile Asp Gln Leu Thr Asn Ile Leu Ala Pro Met Ala Val
            180                 185                 190

Gly Gln Ile Met Thr Phe Gly Ser Pro Val Ile Gly Cys Gly Phe Ile
        195                 200                 205

Ser Gly Trp Asn Leu Val Ser Met Cys Val Glu Tyr Phe Leu Leu Trp
    210                 215                 220

Lys Val Tyr Gln Lys Thr Pro Ala Leu Ala Val Lys Ala Ala Leu Lys
225                 230                 235                 240

Val Glu Glu Ser Glu Leu Lys Gln Leu Thr Ser Pro Lys Asp Thr Glu
                245                 250                 255

Pro Lys Pro Leu Glu Gly Thr His Leu Met Gly Glu Lys Asp Ser Asn
            260                 265                 270

Ile Arg Glu Leu Glu Cys Glu Gln Glu Pro Thr Cys Ala Ser Gln Met
        275                 280                 285

Ala Glu Pro Phe Arg Thr Phe Arg Asp Gly Trp Val Ser Tyr Tyr Asn
    290                 295                 300

Gln Pro Val Phe Leu Ala Gly Met Gly Leu Ala Phe Leu Tyr Met Thr
305                 310                 315                 320
```

```
Val Leu Gly Phe Asp Cys Ile Thr Thr Gly Tyr Ala Tyr Thr Gln Gly
            325                 330                 335

Leu Ser Gly Ser Ile Leu Ser Ile Leu Met Gly Ala Ser Ala Ile Thr
        340                 345                 350

Gly Ile Met Gly Thr Val Ala Phe Thr Trp Leu Arg Arg Lys Cys Gly
    355                 360                 365

Leu Val Arg Thr Gly Leu Phe Ser Gly Leu Ala Gln Leu Ser Cys Leu
370                 375                 380

Ile Leu Cys Val Ile Ser Val Phe Met Pro Gly Ser Pro Leu Asp Leu
385                 390                 395                 400

Ser Val Ser Pro Phe Glu Asp Ile Arg Ser Arg Phe Val Asn Val Glu
            405                 410                 415

Pro Val Ser Pro Thr Thr Lys Ile Pro Glu Thr Val Phe Thr Thr Glu
        420                 425                 430

Met His Met Ser Asn Met Ser Asn Val His Glu Met Ser Thr Lys Pro
    435                 440                 445

Ile Pro Ile Val Ser Val Ser Leu Leu Phe Ala Gly Val Ile Ala Ala
450                 455                 460

Arg Ile Gly Leu Trp Ser Phe Asp Leu Thr Val Thr Gln Leu Leu Gln
465                 470                 475                 480

Glu Asn Val Ile Glu Ser Glu Arg Gly Ile Ile Asn Gly Val Gln Asn
            485                 490                 495

Ser Met Asn Tyr Leu Leu Asp Leu His Phe Ile Met Val Ile Leu
        500                 505                 510

Ala Pro Asn Pro Glu Ala Phe Gly Leu Leu Val Leu Ile Ser Val Ser
    515                 520                 525

Phe Val Ala Met Gly His Leu Met Tyr Phe Arg Phe Ala Gln Lys Thr
530                 535                 540

Leu Gly Asn Gln Ile Phe Val Cys Gly Pro Asp Glu Lys Glu Val Thr
545                 550                 555                 560

Asp Glu Asn Gln Pro Asn Thr Ser Val Val
            565                 570

<210> SEQ ID NO 8
<211> LENGTH: 1713
<212> TYPE: DNA
<213> ORGANISM: Mus sp

<400> SEQUENCE: 8
atgaccaagg caagagatca aacccatcag gaaggatgct gtggatcctt agcaaactac      60
ctgacctcag caaaattcct cctctacctt ggccactctc tctccacttg ggggatcgg     120 atgtggcact ttgcagtgtc tgtgtttctg gtggaactct atggaaacag ccttctcttg     180
acagctgtct atggactggt ggtggcaggc tctgttctgg tcctgggagc catcattggt     240
gactgggtgg ataagaatgc cagacttaaa gtgcccagag cgtcactagt ggttcagaat     300
gtgtccgtca tcctctgcgg aatcatcctg atgatggttt tcctacacaa gaatgagctc     360
ctgaccatgt accatggatg ggtccttact gtctgctaca tcctgatcat cactattgca     420
aacattgcaa atttggccag tactgccact gcgatcacaa tccaagggga ctggattgtt     480
gttgtggcag agaaaacaga gagcagatta gcagacatga atgctaccat agaaggatt     540 gaccagctaa ccaacatcct ggccccatg gctgtcggcc agattatgac atttggttct     600
ccagtcattg gctgtggttt catttccggt tggaatttgg tggccatgtg tgtggagtac     660
ttcttgctct ggaaggttta ccagaagacc cctgctctgg ctgtaaaagc tgctctcaag     720
```

```
gtagaggagt cagaactgaa gcagctgacc tcacctaaag atactgagcc aaaacctttg      780
gagggaactc atctaatggg tgagaaagac tccaacatcc gtgaacttga atgtgaacaa      840
gagcccacct gtgcctccca gatggcagag cccttccgca ctttccgaga tggatgggtc      900
tcctactata accagccagt gtttctggct ggcatgggcc tggcttttcct ctatatgaca     960 gtcctgggct tgactgtat cactacaggg tacgcctaca ctcaggggct gagtggatcc       1020
atccttagta ttttgatggg agcatcagca ataactggaa taatgggaac tgtggccttc     1080
acctggctac gtcgaaaatg tggccttgtt cggactggtc tattctcagg actagcccag     1140 cttttcctgtt taatcttgtg tgtgatctcc gtattcatgc ctggaagccc cttggacctg    1200
tctgtttctc catttgaaga tatccgttct aggtttgtga atgtggagcc agtgtcccca     1260
actaccaaaa tacctgagac cgtctttaca acagaaatgc atatgtccaa catgtctaat     1320
gtccatgaga tgagtactaa acccatcccc atagtctctg tcagcctgct gtttgcagga    1380
gtcattgctg ctagaatcgg tctttggtcc tttgatttga cggtgacaca gttgctgcaa    1440
gaaaatgtaa ttgaatctga aagaggcatt atcaatggtg tgcagaactc catgaactac    1500
cttcttgacc ttctgcattt catcatggtc atcttggccc caaatcctga agcttttggc    1560
ttgctggtat tgatttcagt ctcctttgtg gcaatgggac atcttatgta tttccgattt    1620
gcccagaaga ctctgggcaa ccagatttttt gtttgtggtc ctgatgaaaa agaagttaca    1680
gatgaaaatc aaccgaatac atctgttgta tag                                 1713
```

<210> SEQ ID NO 9
<211> LENGTH: 56
<212> TYPE: PRT
<213> ORGANISM: Homo sapiens

<400> SEQUENCE: 9

```
Pro Gly Ser Pro Leu Asp Leu Ser Val Ser Pro Phe Glu Asp Ile Arg
 1               5                  10                  15

Ser Arg Phe Ile Gln Gly Glu Ser Ile Thr Pro Thr Lys Ile Pro Glu
            20                  25                  30

Ile Thr Thr Glu Ile Tyr Met Ser Asn Gly Ser Asn Ser Ala Asn Ile
        35                  40                  45

Val Pro Glu Thr Ser Pro Glu Ser
    50                  55
```

<210> SEQ ID NO 10
<211> LENGTH: 642
<212> TYPE: DNA
<213> ORGANISM: Artificial
<220> FEATURE:
<223> OTHER INFORMATION: Synthetic

<400> SEQUENCE: 10

```
gacatccaga tgacccagtc tccatcctcc ctgtctgcat ctgtaggaga cagagtcacc       60
atcacttgca gggcgagtaa gagcattagc aaatatacag cctggtatca gcagaaacca      120
gggaaagccc ctaagctcct gatctatgct ggtccaagc ggcactgggg agtcccatca       180
aggttcagtg gcagtggatc tgggacagat ttcactctca ccatcagcag tctgcaacct     240
gaagattttg caacttacta ttgtcaacaa cataatgaat acccgtacac gttcggcgga     300
gggaccaagg tggagatcaa acggactgtg gctgcaccat ctgtcttcat cttcccgcca     360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
```

```
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gc                       642
```

```
<210> SEQ ID NO 11
<211> LENGTH: 39
<212> TYPE: PRT
<213> ORGANISM: Artificial
<220> FEATURE:
<223> OTHER INFORMATION: Synthetic

<400> SEQUENCE: 11

Ile Ser Gln Ala Val His Ala Ala His Ala Glu Ile Asn Glu Gly Pro
1               5                   10                  15

Gly Pro Gly Ser Pro Phe Glu Asp Ile Arg Ser Arg Phe Ile Gln Gly
            20                  25                  30

Glu Ser Ile Thr Pro Thr Lys
        35

<210> SEQ ID NO 12
<211> LENGTH: 20
<212> TYPE: PRT
<213> ORGANISM: Homo sapiens

<400> SEQUENCE: 12

Ser Pro Phe Glu Asp Ile Arg Ser Arg Phe Ile Gln Gly Glu Ser Ile
1               5                   10                  15

Thr Pro Thr Lys
            20

<210> SEQ ID NO 13
<211> LENGTH: 14
<212> TYPE: PRT
<213> ORGANISM: Homo sapiens

<400> SEQUENCE: 13

Glu Asp Ile Arg Ser Arg Phe Ile Gln Gly Glu Ser Ile Thr
1               5                   10

<210> SEQ ID NO 14
<211> LENGTH: 14
<212> TYPE: PRT
<213> ORGANISM: Homo sapiens

<400> SEQUENCE: 14

Arg Ser Arg Phe Ile Gln Gly Glu Ser Ile Thr Pro Thr Lys
1               5                   10

<210> SEQ ID NO 15
<211> LENGTH: 13
<212> TYPE: PRT
<213> ORGANISM: Homo sapiens

<400> SEQUENCE: 15

Ser Pro Phe Glu Asp Ile Arg Ser Arg Phe Ile Gln Gly
1               5                   10

<210> SEQ ID NO 16
<211> LENGTH: 11
<212> TYPE: PRT
<213> ORGANISM: Homo sapiens

<400> SEQUENCE: 16
```

```
Arg Ser Arg Phe Ile Gln Gly Glu Ser Ile Thr
1               5                   10
```

<210> SEQ ID NO 17
<211> LENGTH: 10
<212> TYPE: PRT
<213> ORGANISM: Artificial
<220> FEATURE:
<223> OTHER INFORMATION: Synthetic

<400> SEQUENCE: 17

```
Gly Tyr Ala Phe Thr Asn Phe Leu Ile Glu
1               5                   10
```

<210> SEQ ID NO 18
<211> LENGTH: 17
<212> TYPE: PRT
<213> ORGANISM: Artificial
<220> FEATURE:
<223> OTHER INFORMATION: Synthetic

<400> SEQUENCE: 18

```
Thr Ile Asn Pro Glu Thr Gly Gly Thr Lys Tyr Asn Glu Lys Phe Arg
1               5                   10                  15

Gly
```

<210> SEQ ID NO 19
<211> LENGTH: 5
<212> TYPE: PRT
<213> ORGANISM: Artificial
<220> FEATURE:
<223> OTHER INFORMATION: Synthetic

<400> SEQUENCE: 19

```
Glu Phe Phe Asp Tyr
1               5
```

<210> SEQ ID NO 20
<211> LENGTH: 11
<212> TYPE: PRT
<213> ORGANISM: Artificial
<220> FEATURE:
<223> OTHER INFORMATION: Synthetic

<400> SEQUENCE: 20

```
Arg Ala Ser Lys Ser Ile Ser Lys Tyr Leu Ala
1               5                   10
```

<210> SEQ ID NO 21
<211> LENGTH: 7
<212> TYPE: PRT
<213> ORGANISM: Artificial
<220> FEATURE:
<223> OTHER INFORMATION: Synthetic

<400> SEQUENCE: 21

```
Ala Gly Ser Thr Leu His Ser
1               5
```

<210> SEQ ID NO 22
<211> LENGTH: 9
<212> TYPE: PRT
<213> ORGANISM: Artificial
<220> FEATURE:
<223> OTHER INFORMATION: Synthetic

<400> SEQUENCE: 22

Gln Gln His Asn Glu Tyr Pro Tyr Thr
1               5

<210> SEQ ID NO 23
<211> LENGTH: 10
<212> TYPE: PRT
<213> ORGANISM: Artificial
<220> FEATURE:
<223> OTHER INFORMATION: Synthetic

<400> SEQUENCE: 23

Gly Tyr Ala Phe Thr Ser Phe Leu Ile Glu
1               5                   10

<210> SEQ ID NO 24
<211> LENGTH: 17
<212> TYPE: PRT
<213> ORGANISM: Artificial
<220> FEATURE:
<223> OTHER INFORMATION: Synthetic

<400> SEQUENCE: 24

Thr Ile Asn Pro Arg Thr Gly Gly Thr Lys Tyr Asn Glu Lys Phe Arg
1               5                   10                  15

Gly

<210> SEQ ID NO 25
<211> LENGTH: 17
<212> TYPE: PRT
<213> ORGANISM: Artificial
<220> FEATURE:
<223> OTHER INFORMATION: Synthetic

<400> SEQUENCE: 25

Thr Ile Asn Pro Lys Thr Gly Gly Thr Lys Tyr Asn Glu Lys Phe Arg
1               5                   10                  15

Gly

<210> SEQ ID NO 26
<211> LENGTH: 17
<212> TYPE: PRT
<213> ORGANISM: Artificial
<220> FEATURE:
<223> OTHER INFORMATION: Synthetic

<400> SEQUENCE: 26

Thr Ile Asn Pro Glu Thr Gly Gly Thr Lys Tyr Asn Ala Lys Phe Arg
1               5                   10                  15

Gly

<210> SEQ ID NO 27
<211> LENGTH: 7
<212> TYPE: PRT
<213> ORGANISM: Artificial
<220> FEATURE:
<223> OTHER INFORMATION: Synthetic

<400> SEQUENCE: 27

Ala Gly Ser Lys Leu His Ser
1               5

<210> SEQ ID NO 28
<211> LENGTH: 7
<212> TYPE: PRT
<213> ORGANISM: Artificial
<220> FEATURE:

```
<223> OTHER INFORMATION: Synthetic

<400> SEQUENCE: 28

Ala Gly Ser Arg Leu His Ser
1               5

<210> SEQ ID NO 29
<211> LENGTH: 9
<212> TYPE: PRT
<213> ORGANISM: Artificial
<220> FEATURE:
<223> OTHER INFORMATION: Synthetic

<400> SEQUENCE: 29

Phe Gln His Asn Glu Tyr Pro Tyr Thr
1               5

<210> SEQ ID NO 30
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Xaa is Asn or Ser

<400> SEQUENCE: 30

Gly Tyr Ala Phe Thr Xaa Phe Leu Ile Glu
1               5                   10

<210> SEQ ID NO 31
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Xaa is Glu, Lys, or Arg
<220> FEATURE:
<221> NAME/KEY: MISC_FEATURE
<222> LOCATION: (13)..(13)
<223> OTHER INFORMATION: Xaa is Glu or Ala

<400> SEQUENCE: 31

Thr Ile Asn Pro Xaa Thr Gly Gly Thr Lys Tyr Asn Xaa Lys Phe Arg
1               5                   10                  15

Gly

<210> SEQ ID NO 32
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is Thr, Lys, or Arg

<400> SEQUENCE: 32

Ala Gly Ser Xaa Leu His Ser
1               5

<210> SEQ ID NO 33
<211> LENGTH: 9
```

```
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is Phe, His, or Gln

<400> SEQUENCE: 33

Xaa Gln His Asn Glu Tyr Pro Tyr Thr
1               5

<210> SEQ ID NO 34
<211> LENGTH: 17
<212> TYPE: PRT
<213> ORGANISM: Artificial
<220> FEATURE:
<223> OTHER INFORMATION: Synthetic

<400> SEQUENCE: 34

Thr Ile Asn Pro Lys Thr Gly Gly Thr Lys Tyr Asn Ala Lys Phe Arg
1               5                   10                  15

Gly

<210> SEQ ID NO 35
<211> LENGTH: 17
<212> TYPE: PRT
<213> ORGANISM: Artificial
<220> FEATURE:
<223> OTHER INFORMATION: Synthetic

<400> SEQUENCE: 35

Thr Ser Asn Pro Arg Thr Gly Gly Thr Lys Tyr Asn Glu Lys Phe Arg
1               5                   10                  15

Gly

<210> SEQ ID NO 36
<211> LENGTH: 17
<212> TYPE: PRT
<213> ORGANISM: Artificial
<220> FEATURE:
<223> OTHER INFORMATION: Synthetic

<400> SEQUENCE: 36

Thr Ile Asn Pro Arg Thr Gly Gly Thr Lys Tyr Lys Glu Lys Phe Arg
1               5                   10                  15

Gly

<210> SEQ ID NO 37
<211> LENGTH: 11
<212> TYPE: PRT
<213> ORGANISM: Artificial
<220> FEATURE:
<223> OTHER INFORMATION: Synthetic

<400> SEQUENCE: 37

Arg Ala Ser Lys Ser Ile Ser Lys Tyr Thr Ala
1               5                   10

<210> SEQ ID NO 38
<211> LENGTH: 11
<212> TYPE: PRT
<213> ORGANISM: Artificial
<220> FEATURE:
<223> OTHER INFORMATION: Synthetic
```

```
<400> SEQUENCE: 38

Arg Ala Ser Lys Ser Ile Ser Lys Tyr Ser Ala
1               5                   10

<210> SEQ ID NO 39
<211> LENGTH: 11
<212> TYPE: PRT
<213> ORGANISM: Artificial
<220> FEATURE:
<223> OTHER INFORMATION: Synthetic

<400> SEQUENCE: 39

Arg Ala Ser Lys Ser Ile Ser Lys Tyr Ala Ala
1               5                   10

<210> SEQ ID NO 40
<211> LENGTH: 9
<212> TYPE: PRT
<213> ORGANISM: Artificial
<220> FEATURE:
<223> OTHER INFORMATION: Synthetic

<400> SEQUENCE: 40

His Gln His Asn Glu Tyr Pro Tyr Thr
1               5

<210> SEQ ID NO 41
<211> LENGTH: 17
<212> TYPE: PRT
<213> ORGANISM: Artificial
<220> FEATURE:
<223> OTHER INFORMATION: Synthetic

<400> SEQUENCE: 41

Thr Ser Asn Pro Arg Thr Gly Gly Thr Lys Tyr Lys Glu Lys Phe Arg
1               5                   10                  15
Gly

<210> SEQ ID NO 42
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: Xaa is Leu, Thr, Ser, or Ala

<400> SEQUENCE: 42

Arg Ala Ser Lys Ser Ile Ser Lys Tyr Xaa Ala
1               5                   10

<210> SEQ ID NO 43
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa is Ser or Ile
<220> FEATURE:
<221> NAME/KEY: MISC_FEATURE
<222> LOCATION: (5)..(5)
<223> OTHER INFORMATION: Xaa is Glu, Lys, or Arg
<220> FEATURE:
<221> NAME/KEY: MISC_FEATURE
```

```
<222> LOCATION: (12)..(12)
<223> OTHER INFORMATION: Xaa is Asn or Lys
<220> FEATURE:
<221> NAME/KEY: MISC_FEATURE
<222> LOCATION: (13)..(13)
<223> OTHER INFORMATION: Xaa is Glu or Ala

<400> SEQUENCE: 43

Thr Xaa Asn Pro Xaa Thr Gly Gly Thr Lys Tyr Xaa Xaa Lys Phe Arg
1               5                   10                  15

Gly

<210> SEQ ID NO 44
<211> LENGTH: 114
<212> TYPE: PRT
<213> ORGANISM: Mus sp

<400> SEQUENCE: 44

Gln Val Gln Leu Lys Gln Ser Gly Ala Glu Leu Val Arg Pro Gly Thr
1               5                   10                  15

Ser Val Lys Val Ser Cys Lys Ala Ser Gly Tyr Ala Phe Thr Asn Phe
                20                  25                  30

Leu Ile Glu Trp Leu Lys Gln Arg Pro Gly Gln Gly Leu Glu Trp Ile
            35                  40                  45

Gly Thr Ile Asn Pro Glu Thr Gly Gly Thr Lys Tyr Asn Glu Lys Phe
        50                  55                  60

Arg Gly Lys Ala Thr Leu Thr Ala Asp Lys Ser Ser Thr Ala Tyr
65                  70                  75                  80

Met Gln Leu Asn Ser Leu Thr Ser Asp Asp Ser Ala Val Tyr Phe Cys
                85                  90                  95

Val Arg Glu Phe Phe Asp Tyr Trp Gly Gln Gly Thr Ser Leu Thr Val
            100                 105                 110

Ser Ser

<210> SEQ ID NO 45
<211> LENGTH: 114
<212> TYPE: PRT
<213> ORGANISM: Artificial
<220> FEATURE:
<223> OTHER INFORMATION: Synthetic

<400> SEQUENCE: 45

Gln Val Gln Leu Lys Gln Ser Gly Ala Glu Leu Val Arg Pro Gly Thr
1               5                   10                  15

Ser Val Lys Val Ser Cys Lys Ala Ser Gly Tyr Ala Phe Thr Ser Phe
                20                  25                  30

Leu Ile Glu Trp Leu Lys Gln Arg Pro Gly Gln Gly Leu Glu Trp Ile
            35                  40                  45

Gly Thr Ile Asn Pro Arg Thr Gly Gly Thr Lys Tyr Asn Glu Lys Phe
        50                  55                  60

Arg Gly Lys Ala Thr Leu Thr Ala Asp Lys Ser Ser Thr Ala Tyr
65                  70                  75                  80

Met Gln Leu Asn Ser Leu Thr Ser Asp Asp Ser Ala Val Tyr Phe Cys
                85                  90                  95

Val Arg Glu Phe Phe Asp Tyr Trp Gly Gln Gly Thr Ser Leu Thr Val
            100                 105                 110

Ser Ser

<210> SEQ ID NO 46
```

```
<211> LENGTH: 114
<212> TYPE: PRT
<213> ORGANISM: Artificial
<220> FEATURE:
<223> OTHER INFORMATION: Synthetic

<400> SEQUENCE: 46

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Ser Phe
            20                  25                  30

Leu Ile Glu Trp Val Arg Gln Ala Pro Gly Gln Gly Leu Glu Trp Met
        35                  40                  45

Gly Thr Ser Asn Pro Arg Thr Gly Gly Thr Lys Tyr Lys Glu Lys Phe
    50                  55                  60

Arg Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Phe Phe Asp Tyr Trp Gly Gln Gly Thr Thr Val Thr Val
            100                 105                 110

Ser Ser

<210> SEQ ID NO 47
<211> LENGTH: 107
<212> TYPE: PRT
<213> ORGANISM: Mus sp

<400> SEQUENCE: 47

Glu Thr Thr Val Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Phe Gln Glu Lys Pro Gly Lys Thr Asn Lys Leu Leu Ile
        35                  40                  45

Tyr Ala Gly Ser Thr Leu His Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Tyr
                85                  90                  95

Thr Phe Gly Gly Gly Thr Lys Leu Glu Leu Lys
            100                 105

<210> SEQ ID NO 48
<211> LENGTH: 107
<212> TYPE: PRT
<213> ORGANISM: Artificial
<220> FEATURE:
<223> OTHER INFORMATION: Synthetic

<400> SEQUENCE: 48

Glu Thr Thr Val Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Phe Gln Glu Lys Pro Gly Lys Thr Asn Lys Leu Leu Ile
        35                  40                  45

Tyr Ala Gly Ser Lys Leu His Ser Gly Ile Pro Ser Arg Phe Ser Gly
```

```
                    50                  55                  60

Ser Gly Ser Gly Thr Asp Phe Thr Leu Thr Ile Ser Ser Leu Glu Pro
 65                  70                  75                  80

Glu Asp Phe Ala Met Tyr Tyr Cys Phe Gln His Asn Glu Tyr Pro Tyr
                 85                  90                  95

Thr Phe Gly Gly Gly Thr Lys Leu Glu Leu Lys
            100                 105

<210> SEQ ID NO 49
<211> LENGTH: 107
<212> TYPE: PRT
<213> ORGANISM: Artificial
<220> FEATURE:
<223> OTHER INFORMATION: Synthetic

<400> SEQUENCE: 49

Asp Ile Gln Met Thr Gln Ser Pro Ser Ser Leu Ser Ala Ser Val Gly
  1               5                  10                  15

Asp Arg Val Thr Ile Thr Cys Arg Ala Ser Lys Ser Ile Ser Lys Tyr
                 20                  25                  30

Thr Ala Trp Tyr Gln Gln Lys Pro Gly Lys Ala Pro Lys Leu Leu Ile
             35                  40                  45

Tyr Ala Gly Ser Lys Leu His Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln His Asn Glu Tyr Pro Tyr
                 85                  90                  95

Thr Phe Gly Gly Gly Thr Lys Val Glu Ile Lys
            100                 105

<210> SEQ ID NO 50
<211> LENGTH: 438
<212> TYPE: PRT
<213> ORGANISM: Mus sp

<400> SEQUENCE: 50

Gln Val Gln Leu Lys Gln Ser Gly Ala Glu Leu Val Arg Pro Gly Thr
  1               5                  10                  15

Ser Val Lys Val Ser Cys Lys Ala Ser Gly Tyr Ala Phe Thr Asn Phe
                 20                  25                  30

Leu Ile Glu Trp Leu Lys Gln Arg Pro Gly Gln Gly Leu Glu Trp Ile
             35                  40                  45

Gly Thr Ile Asn Pro Glu Thr Gly Gly Thr Lys Tyr Asn Glu Lys Phe
 50                  55                  60

Arg Gly Lys Ala Thr Leu Thr Ala Asp Lys Ser Ser Ser Thr Ala Tyr
 65                  70                  75                  80

Met Gln Leu Asn Ser Leu Thr Ser Asp Asp Ser Ala Val Tyr Phe Cys
                 85                  90                  95

Val Arg Glu Phe Phe Asp Tyr Trp Gly Gln Gly Thr Ser Leu Thr Val
            100                 105                 110

Ser Ser Ala Lys Thr Thr Pro Pro Ser Val Tyr Pro Leu Ala Pro Gly
            115                 120                 125

Ser Ala Ala Gln Thr Asn Ser Met Val Thr Leu Gly Cys Leu Val Lys
        130                 135                 140

Gly Tyr Phe Pro Glu Pro Val Thr Val Thr Trp Asn Ser Gly Ser Leu
145                 150                 155                 160
```

```
Ser Ser Gly Val His Thr Phe Pro Ala Val Leu Gln Ser Asp Leu Tyr
            165                 170                 175
Thr Leu Ser Ser Ser Val Thr Val Pro Ser Ser Thr Trp Pro Ser Glu
        180                 185                 190
Thr Val Thr Cys Asn Val Ala His Pro Ala Ser Ser Thr Lys Val Asp
            195                 200                 205
Lys Lys Ile Val Pro Arg Asp Cys Gly Cys Lys Pro Cys Ile Cys Thr
        210                 215                 220
Val Pro Glu Val Ser Ser Val Phe Ile Phe Pro Pro Lys Pro Lys Asp
225                 230                 235                 240
Val Leu Thr Ile Thr Leu Thr Pro Lys Val Thr Cys Val Val Val Asp
            245                 250                 255
Ile Ser Lys Asp Asp Pro Glu Val Gln Phe Ser Trp Phe Val Asp Asp
        260                 265                 270
Val Glu Val His Thr Ala Gln Thr Gln Pro Arg Glu Glu Gln Phe Asn
            275                 280                 285
Ser Thr Phe Arg Ser Val Ser Glu Leu Pro Ile Met His Gln Asp Trp
        290                 295                 300
Leu Asn Gly Lys Glu Phe Lys Cys Arg Val Asn Ser Ala Ala Phe Pro
305                 310                 315                 320
Ala Pro Ile Glu Lys Thr Ile Ser Lys Thr Lys Gly Arg Pro Lys Ala
            325                 330                 335
Pro Gln Val Tyr Thr Ile Pro Pro Lys Glu Gln Met Ala Lys Asp
        340                 345                 350
Lys Val Ser Leu Thr Cys Met Ile Thr Asp Phe Phe Pro Glu Asp Ile
            355                 360                 365
Thr Val Glu Trp Gln Trp Asn Gly Gln Pro Ala Glu Asn Tyr Lys Asn
        370                 375                 380
Thr Gln Pro Ile Met Asp Thr Asp Gly Ser Tyr Phe Val Tyr Ser Lys
385                 390                 395                 400
Leu Asn Val Gln Lys Ser Asn Trp Glu Ala Gly Asn Thr Phe Thr Cys
            405                 410                 415
Ser Val Leu His Glu Gly Leu His Asn His His Thr Glu Lys Ser Leu
        420                 425                 430
Ser His Ser Pro Gly Lys
            435

<210> SEQ ID NO 51
<211> LENGTH: 438
<212> TYPE: PRT
<213> ORGANISM: Artificial
<220> FEATURE:
<223> OTHER INFORMATION: Synthetic

<400> SEQUENCE: 51

Gln Val Gln Leu Lys Gln Ser Gly Ala Glu Leu Val Arg Pro Gly Thr
1               5                   10                  15
Ser Val Lys Val Ser Cys Lys Ala Ser Gly Tyr Ala Phe Thr Ser Phe
            20                  25                  30
Leu Ile Glu Trp Leu Lys Gln Arg Pro Gly Gln Gly Leu Glu Trp Ile
        35                  40                  45
Gly Thr Ile Asn Pro Arg Thr Gly Gly Thr Lys Tyr Asn Glu Lys Phe
    50                  55                  60
Arg Gly Lys Ala Thr Leu Thr Ala Asp Lys Ser Ser Ser Thr Ala Tyr
65                  70                  75                  80
Met Gln Leu Asn Ser Leu Thr Ser Asp Asp Ser Ala Val Tyr Phe Cys
```

```
                    85                  90                  95
Val Arg Glu Phe Phe Asp Tyr Trp Gly Gln Gly Thr Ser Leu Thr Val
                100                 105                 110

Ser Ser Ala Lys Thr Thr Pro Pro Ser Val Tyr Pro Leu Ala Pro Gly
            115                 120                 125

Ser Ala Ala Gln Thr Asn Ser Met Val Thr Leu Gly Cys Leu Val Lys
        130                 135                 140

Gly Tyr Phe Pro Glu Pro Val Thr Val Thr Trp Asn Ser Gly Ser Leu
145                 150                 155                 160

Ser Ser Gly Val His Thr Phe Pro Ala Val Leu Gln Ser Asp Leu Tyr
                165                 170                 175

Thr Leu Ser Ser Ser Val Thr Val Pro Ser Ser Thr Trp Pro Ser Glu
            180                 185                 190

Thr Val Thr Cys Asn Val Ala His Pro Ala Ser Ser Thr Lys Val Asp
        195                 200                 205

Lys Lys Ile Val Pro Arg Asp Cys Gly Cys Lys Pro Cys Ile Cys Thr
    210                 215                 220

Val Pro Glu Val Ser Ser Val Phe Ile Phe Pro Pro Lys Pro Lys Asp
225                 230                 235                 240

Val Leu Thr Ile Thr Leu Thr Pro Lys Val Thr Cys Val Val Val Asp
                245                 250                 255

Ile Ser Lys Asp Asp Pro Glu Val Gln Phe Ser Trp Phe Val Asp Asp
            260                 265                 270

Val Glu Val His Thr Ala Gln Thr Gln Pro Arg Glu Glu Gln Phe Asn
        275                 280                 285

Ser Thr Phe Arg Ser Val Ser Glu Leu Pro Ile Met His Gln Asp Trp
    290                 295                 300

Leu Asn Gly Lys Glu Phe Lys Cys Arg Val Asn Ser Ala Ala Phe Pro
305                 310                 315                 320

Ala Pro Ile Glu Lys Thr Ile Ser Lys Thr Lys Gly Arg Pro Lys Ala
                325                 330                 335

Pro Gln Val Tyr Thr Ile Pro Pro Lys Glu Gln Met Ala Lys Asp
            340                 345                 350

Lys Val Ser Leu Thr Cys Met Ile Thr Asp Phe Phe Pro Glu Asp Ile
        355                 360                 365

Thr Val Glu Trp Gln Trp Asn Gly Gln Pro Ala Glu Asn Tyr Lys Asn
    370                 375                 380

Thr Gln Pro Ile Met Asp Thr Asp Gly Ser Tyr Phe Val Tyr Ser Lys
385                 390                 395                 400

Leu Asn Val Gln Lys Ser Asn Trp Glu Ala Gly Asn Thr Phe Thr Cys
                405                 410                 415

Ser Val Leu His Glu Gly Leu His Asn His His Thr Glu Lys Ser Leu
            420                 425                 430

Ser His Ser Pro Gly Lys
        435

<210> SEQ ID NO 52
<211> LENGTH: 440
<212> TYPE: PRT
<213> ORGANISM: Artificial
<220> FEATURE:
<223> OTHER INFORMATION: Synthetic

<400> SEQUENCE: 52

Gln Val Gln Leu Val Gln Ser Gly Ala Glu Val Lys Lys Pro Gly Ser
1               5                   10                  15
```

Ser Val Lys Val Ser Cys Lys Ala Ser Gly Tyr Ala Phe Thr Ser Phe
            20                  25                  30

Leu Ile Glu Trp Val Arg Gln Ala Pro Gly Gln Gly Leu Glu Trp Met
        35                  40                  45

Gly Thr Ser Asn Pro Arg Thr Gly Gly Thr Lys Tyr Lys Glu Lys Phe
    50                  55                  60

Arg Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Phe Phe Asp Tyr Trp Gly Gln Gly Thr Thr Val Thr Val
                100                 105                 110

Ser Ser Ala Ser Thr Lys Gly Pro Ser Val Phe Pro Leu Ala Pro Cys
            115                 120                 125

Ser Arg Ser Thr Ser Glu Ser Thr Ala Ala Leu Gly Cys Leu Val Lys
        130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
                180                 185                 190

Lys Thr Tyr Thr Cys Asn Val Asp His Lys Pro Ser Asn Thr Lys Val
            195                 200                 205

Asp Lys Arg Val Glu Ser Lys Tyr Gly Pro Pro Cys Pro Pro Cys Pro
210                 215                 220

Ala Pro Glu Ala Ala Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser Gln Glu Asp Pro Glu Val Gln Phe Asn Trp Tyr
            260                 265                 270

Val Asp Gly Val Glu Val His Asn Ala Lys Thr Lys Pro Arg Glu Glu
        275                 280                 285

Gln Phe Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Gly Leu Pro Ser Ser Ile Glu Lys Thr Ile Ser Lys Ala Lys Gly Gln
                325                 330                 335

Pro Arg Glu Pro Gln Val Tyr Thr Leu Pro Pro Ser Gln Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Arg Leu Thr Val Asp Lys Ser Arg Trp Gln Glu Gly Asn Val
                405                 410                 415

Phe Ser Cys Ser Val Met His Glu Ala Leu His Asn His Tyr Thr Gln
            420                 425                 430

Lys Ser Leu Ser Leu Ser Leu Gly

<210> SEQ ID NO 53
<211> LENGTH: 214
<212> TYPE: PRT
<213> ORGANISM: Mus sp

<400> SEQUENCE: 53

Glu Thr Thr Val Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Phe Gln Glu Lys Pro Gly Lys Thr Asn Lys Leu Leu Ile
        35                  40                  45

Tyr Ala Gly Ser Thr Leu His Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Tyr
                85                  90                  95

Thr Phe Gly Gly Gly Thr Lys Leu Glu Leu Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 54
<211> LENGTH: 214
<212> TYPE: PRT
<213> ORGANISM: Artificial
<220> FEATURE:
<223> OTHER INFORMATION: Synthetic

<400> SEQUENCE: 54

Glu Thr Thr Val Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Phe Gln Glu Lys Pro Gly Lys Thr Asn Lys Leu Leu Ile
        35                  40                  45

Tyr Ala Gly Ser Lys Leu His Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Phe Gln His Asn Glu Tyr Pro Tyr
                85                  90                  95

```
Thr Phe Gly Gly Gly Thr Lys Leu Glu Leu Lys Arg Ala Asp Ala Ala
                100                 105                 110

Pro Thr Val Ser Ile Phe Pro Pro Ser Ser Glu Gln Leu Thr Ser Gly
            115                 120                 125

Gly Ala Ser Val Val Cys Phe Leu Asn Asn Phe Tyr Pro Lys Asp Ile
        130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 55
<211> LENGTH: 214
<212> TYPE: PRT
<213> ORGANISM: Artificial
<220> FEATURE:
<223> OTHER INFORMATION: Synthetic

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Ile Ser Lys Tyr
            20                  25                  30

Thr Ala Trp Tyr Gln Gln Lys Pro Gly Lys Ala Pro Lys Leu Leu Ile
        35                  40                  45

Tyr Ala Gly Ser Lys Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asn Glu Tyr Pro Tyr
                85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 56
<211> LENGTH: 114
<212> TYPE: PRT
```

```
<213> ORGANISM: Artificial
<220> FEATURE:
<223> OTHER INFORMATION: Synthetic
<220> FEATURE:
<221> NAME/KEY: MISC_FEATURE
<222> LOCATION: (28)..(28)
<223> OTHER INFORMATION: Xaa is Ala or Arg
<220> FEATURE:
<221> NAME/KEY: MISC_FEATURE
<222> LOCATION: (57)..(57)
<223> OTHER INFORMATION: Xaa is Gly or Arg
<220> FEATURE:
<221> NAME/KEY: MISC_FEATURE
<222> LOCATION: (58)..(58)
<223> OTHER INFORMATION: Xaa is Thr or Arg
<220> FEATURE:
<221> NAME/KEY: MISC_FEATURE
<222> LOCATION: (62)..(62)
<223> OTHER INFORMATION: Xaa is Glu, Ser, or Thr
<220> FEATURE:
<221> NAME/KEY: MISC_FEATURE
<222> LOCATION: (102)..(102)
<223> OTHER INFORMATION: Xaa is Asp or Val

<400> SEQUENCE: 56

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Xaa Phe Thr Ser Phe
            20                  25                  30

Leu Ile Glu Trp Val Arg Gln Ala Pro Gly Gln Gly Leu Glu Trp Met
        35                  40                  45

Gly Thr Ser Asn Pro Arg Thr Gly Xaa Xaa Lys Tyr Lys Xaa Lys Phe
    50                  55                  60

Arg Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Phe Phe Xaa Tyr Trp Gly Gln Gly Thr Thr Val Thr Val
            100                 105                 110

Ser Ser

<210> SEQ ID NO 57
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (54)..(54)
<223> OTHER INFORMATION: Xaa is Leu or Arg
<220> FEATURE:
<221> NAME/KEY: MISC_FEATURE
<222> LOCATION: (55)..(55)
<223> OTHER INFORMATION: Xaa is His, Arg, or Tyr
<220> FEATURE:
<221> NAME/KEY: MISC_FEATURE
<222> LOCATION: (56)..(56)
<223> OTHER INFORMATION: Xaa is Ser, Trp, or Tyr

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Ile Ser Lys Tyr
            20                  25                  30

Thr Ala Trp Tyr Gln Gln Lys Pro Gly Lys Ala Pro Lys Leu Leu Ile
        35                  40                  45
```

```
Tyr Ala Gly Ser Lys Xaa Xaa Xaa Gly Val Pro Ser Arg Phe Ser Gly
    50              55                  60

Ser Gly Ser Gly Thr Asp Phe Thr Leu Thr Ile Ser Ser Leu Gln Pro
65              70              75                      80

Glu Asp Phe Ala Thr Tyr Tyr Cys Gln Gln His Asn Glu Tyr Pro Tyr
                85              90                  95

Thr Phe Gly Gly Gly Thr Lys Val Glu Ile Lys
            100             105
```

<210> SEQ ID NO 58
<211> LENGTH: 342
<212> TYPE: DNA
<213> ORGANISM: Mus sp

<400> SEQUENCE: 58

| | | |
|---|---|---|
| caggtgcagc tgaagcagtc tggagctgaa ctggtaaggc ctgggacttc agtgaaggtg | 60 |
| tcctgcaagg cttctggata cgccttcact aatttcttga tagagtggtt aaagcagagg | 120 |
| cctggacagg gccttgagtg gattggaacg attaatcctg aaactggtgg tactaagtat | 180 |
| aatgagaagt tcaggggcaa ggcaacactg actgctgaca atcttccag cactgcctat | 240 |
| atgcagctca acagcctgac atctgatgac tctgcggtct atttctgtgt cagagagttt | 300 |
| tttgactact ggggccaagg caccagtctc acagtctcct ca | 342 |

<210> SEQ ID NO 59
<211> LENGTH: 321
<212> TYPE: DNA
<213> ORGANISM: Mus sp

<400> SEQUENCE: 59

| | | |
|---|---|---|
| gaaacaactg tgacccagtc tccatcttat cttgctgcat ctcctggaga aaccattact | 60 |
| attaattgca gggcgagtaa gagcattagc aaatatttag cctggtttca agagaaacct | 120 |
| gggaaaacta ataagcttct tatctacgct ggatccactt tgcactctgg aattccatca | 180 |
| aggttcagtg gcagtggatc cggtacagat ttcactctca ccatcagtag cctggagcct | 240 |
| gaagattttg caatgtatta ctgtcaacaa cataatgaat acccgtacac gttcggagga | 300 |
| gggaccaagc tggagctgaa a | 321 |

<210> SEQ ID NO 60
<211> LENGTH: 342
<212> TYPE: DNA
<213> ORGANISM: Artificial
<220> FEATURE:
<223> OTHER INFORMATION: Synthetic

<400> SEQUENCE: 60

| | | |
|---|---|---|
| caggtgcagc tgaagcagtc tggagctgaa ctggtaaggc ctgggacttc agtgaaggtg | 60 |
| tcctgcaagg cttctggata cgccttcact tcgttcttga tagtggtt aaagcagagg | 120 |
| cctggacagg gccttgagtg gattggaacg attaatccta ggactggtgg tactaagtat | 180 |
| aatgagaagt tcaggggcaa ggcaacactg actgctgaca atcttccag cactgcctat | 240 |
| atgcagctca acagcctgac atctgatgac tctgcggtct atttctgtgt cagagagttt | 300 |
| tttgactact ggggccaagg caccagtctc acagtctcct ca | 342 |

<210> SEQ ID NO 61
<211> LENGTH: 321
<212> TYPE: DNA
<213> ORGANISM: Artificial
<220> FEATURE:

<223> OTHER INFORMATION: Synthetic

<400> SEQUENCE: 61

```
gaaacaactg tgacccagtc tccatcttat cttgctgcat ctcctggaga aaccattact      60
attaattgca gggcgagtaa gagcattagc aaatatttag cctggtttca agagaaacct     120
gggaaaacta ataagcttct tatctacgct ggatccaagt tgcactctgg aattccatca     180
aggttcagtg gcagtggatc cggtacagat ttcactctca ccatcagtag cctggagcct     240
gaagattttg caatgtatta ctgtttccaa cataatgaat acccgtacac gttcggagga     300
gggaccaagc tggagctgaa a                                               321
```

<210> SEQ ID NO 62
<211> LENGTH: 342
<212> TYPE: DNA
<213> ORGANISM: Artificial
<220> FEATURE:
<223> OTHER INFORMATION: Synthetic

<400> SEQUENCE: 62

```
caggtgcagc tggtgcagtc tggggctgag gtgaagaagc ctgggtcctc agtgaaggtt      60
tcctgcaagg catctggcta cgccttcact tcgttcttga tagagtgggt gcgacaggcc     120
cctggacaag gcttgagtg gatgggaacg attaatccta ggactggtgg tactaagtat      180
aatgagaagt tcaggggcag agtcaccatt accgcggaca atccacgag cacagcctac      240
atggagctga gcagcctgag atctgaggac acggccgtgt attactgtgc gcgcgagttt     300
tttgactact ggggccaagg aaccacggtc accgtctcct ca                        342
```

<210> SEQ ID NO 63
<211> LENGTH: 321
<212> TYPE: DNA
<213> ORGANISM: Artificial
<220> FEATURE:
<223> OTHER INFORMATION: Synthetic

<400> SEQUENCE: 63

```
gacatccaga tgacccagtc tccatcctcc ctgtctgcat ctgtaggaga cagagtcacc      60
atcacttgca gggcgagtaa gagcattagc aaatatttag cctggtatca gcagaaacca     120
gggaaagccc ctaagctcct gatctatgct ggatccaagt tgcactctgg agtcccatca     180
aggttcagtg gcagtggatc tgggacagat ttcactctca ccatcagcag tctgcaacct     240
gaagattttg caacttacta ttgtttccaa cataatgaat acccgtacac gttcggcgga     300
gggaccaagg tggagatcaa a                                               321
```

<210> SEQ ID NO 64
<211> LENGTH: 342
<212> TYPE: DNA
<213> ORGANISM: Artificial
<220> FEATURE:
<223> OTHER INFORMATION: Synthetic

<400> SEQUENCE: 64

```
caggtgcagc tggtgcagtc tggggctgag gtgaagaagc ctgggtcctc agtgaaggtt      60
tcctgcaagg catctggcta cgccttcact tcgttcttga tagagtgggt gcgacaggcc     120
cctggacaag gcttgagtg gatgggaacg agtaatccta ggactggtgg tactaagtat      180
aaagagaagt tcaggggcag agtcaccatt accgcggaca atccacgag cacagcctac      240
atggagctga gcagcctgag atctgaggac acggccgtgt attactgtgc gcgcgagttt     300
```

-continued

```
tttgactact ggggccaagg aaccacggtc accgtctcct ca            342
```

<210> SEQ ID NO 65
<211> LENGTH: 321
<212> TYPE: DNA
<213> ORGANISM: Artificial
<220> FEATURE:
<223> OTHER INFORMATION: Synthetic

<400> SEQUENCE: 65

```
gacatccaga tgacccagtc tccatcctcc ctgtctgcat ctgtaggaga cagagtcacc    60
atcacttgca gggcgagtaa gagcattagc aaatatacag cctggtatca gcagaaacca   120
gggaaagccc ctaagctcct gatctatgct gggtccaagt tgcactctgg agtcccatca   180
aggttcagtg gcagtggatc tgggacagat ttcactctca ccatcagcag tctgcaacct   240
gaagattttg caacttacta ttgtcaacaa cataatgaat acccgtacac gttcggcgga   300
gggaccaagg tggagatcaa a                                             321
```

<210> SEQ ID NO 66
<211> LENGTH: 329
<212> TYPE: PRT
<213> ORGANISM: Artificial
<220> FEATURE:
<223> OTHER INFORMATION: Synthetic

<400> SEQUENCE: 66

```
Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
```

```
                        245                 250                 255
Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 67
<211> LENGTH: 329
<212> TYPE: PRT
<213> ORGANISM: Artificial
<220> FEATURE:
<223> OTHER INFORMATION: Synthetic

<400> SEQUENCE: 67

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

```
Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 68
<211> LENGTH: 325
<212> TYPE: PRT
<213> ORGANISM: Homo sapiens

<400> SEQUENCE: 68

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Met Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly
                325
```

<210> SEQ ID NO 69
<211> LENGTH: 326
<212> TYPE: PRT
<213> ORGANISM: Artificial
<220> FEATURE:
<223> OTHER INFORMATION: Synthetic

<400> SEQUENCE: 69

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
                325
```

<210> SEQ ID NO 70
<211> LENGTH: 326
<212> TYPE: PRT
<213> ORGANISM: Artificial
<220> FEATURE:

<223> OTHER INFORMATION: Synthetic

<400> SEQUENCE: 70

```
Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Pro Cys Pro Ala Pro
            100                 105                 110
Glu Ala Ala Gly Gly Pro Ser Val Phe Leu Phe Pro Pro Lys Pro Lys
        115                 120                 125
Asp Thr Leu Met Ile Ser Arg Thr Pro Glu Val Thr Cys Val Val Val
130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
Asn Ser Thr Tyr Arg Val Val Ser Val Leu Thr Val Leu His Gln Asp
            180                 185                 190
Trp Leu Asn Gly Lys Glu Tyr Lys Cys Lys Val Ser Asn Lys Gly Leu
        195                 200                 205
Pro Ser Ser Ile Glu Lys Thr Ile Ser Lys Ala Lys Gly Gln Pro Arg
    210                 215                 220
Glu Pro Gln Val Tyr Thr Leu Pro Pro Ser Gln Glu Glu Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
            260                 265                 270
Thr Thr Pro Pro Val Leu Asp Ser Asp Gly Ser Phe Phe Leu Tyr Ser
        275                 280                 285
Arg Leu Thr Val Asp Lys Ser Arg Trp Gln Glu Gly Asn Val Phe Ser
    290                 295                 300
Cys Ser Val Met His Glu Ala Leu His Asn His Tyr Thr Gln Lys Ser
305                 310                 315                 320
Leu Ser Leu Ser Leu Gly
                325
```

<210> SEQ ID NO 71
<211> LENGTH: 978
<212> TYPE: DNA
<213> ORGANISM: Artificial
<220> FEATURE:
<223> OTHER INFORMATION: Synthetic

<400> SEQUENCE: 71

```
gcctccacca agggcccatc ggtcttcccg ctagcgccct gctccaggag cacctccgag    60
agcacagccg ccctgggctg cctggtcaag gactacttcc ccgaaccggt gacggtgtcg   120
```

```
tggaactcag gcgccctgac cagcggcgtg cacaccttcc cggctgtcct acagtcctca      180
ggactctact ccctcagcag cgtggtgacc gtgccctcca gcagcttggg cacgaagacc      240
tacacctgca acgtagatca caagcccagc aacaccaagg tggacaagag agttgagtcc      300
aaatatggtc ccccatgccc accctgccca gcacctgagg ccgccggggg accatcagtc      360
ttcctgttcc ccccaaaacc caaggacact ctcatgatct cccggacccc tgaggtcacg      420
tgcgtggtgg tggacgtgag ccaggaagac cccgaggtcc agttcaactg gtacgtggat      480
ggcgtggagg tgcataatgc caagacaaag ccgcgggagg agcagttcaa cagcacgtac      540
cgtgtggtca gcgtcctcac cgtcctgcac caggactggc tgaacggcaa ggagtacaag      600
tgcaaggtct ccaacaaagg cctcccgtcc tccatcgaga aaaccatctc caaagccaaa      660
gggcagcccc gagagccaca ggtgtacacc ctgcccccat cccaggagga gatgaccaag      720
aaccaggtca gcctgacctg cctggtcaaa ggcttctacc ccagcgacat cgccgtggag      780
tgggaaagca atgggcagcc ggagaacaac tacaagacca cgcctcccgt gctggactcc      840
gacggctcct tcttcctcta cagcaggcta accgtggaca agagcaggtg gcaggagggg      900
aatgtcttct catgctccgt gatgcatgag gctctgcaca accactacac acagaagagc      960
ctctccctgt ctctgggt                                                   978

<210> SEQ ID NO 72
<211> LENGTH: 107
<212> TYPE: PRT
<213> ORGANISM: Homo sapiens

<400> SEQUENCE: 72

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 73
<211> LENGTH: 321
<212> TYPE: DNA
<213> ORGANISM: Homo sapiens

<400> SEQUENCE: 73
cggactgtgg ctgcaccatc tgtcttcatc ttcccgccat ctgatgagca gttgaaatct      60
ggaactgcct ctgttgtgtg cctgctgaat aacttctatc ccagagaggc caaagtacag      120
tggaaggtgg ataacgccct ccaatcgggt aactcccagg agagtgtcac agagcaggac      180
agcaaggaca gcacctacag cctcagcagc accctgacgc tgagcaaagc agactacgag      240
aaacacaaag tctacgcctg cgaagtcacc catcagggcc tgagctcgcc cgtcacaaag      300
agcttcaaca ggggagagtg c                                               321
```

<210> SEQ ID NO 74
<211> LENGTH: 23
<212> TYPE: PRT
<213> ORGANISM: Homo sapiens

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 75
<211> LENGTH: 15
<212> TYPE: PRT
<213> ORGANISM: Homo sapiens

<400> SEQUENCE: 75

Trp Tyr Gln Gln Lys Pro Gly Lys Ala Pro Lys Leu Leu Ile Tyr
1               5                   10                  15

<210> SEQ ID NO 76
<211> LENGTH: 32
<212> TYPE: PRT
<213> ORGANISM: Homo sapiens

<400> SEQUENCE: 76

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 77
<211> LENGTH: 10
<212> TYPE: PRT
<213> ORGANISM: Homo sapiens

<400> SEQUENCE: 77

Phe Gly Gly Gly Thr Lys Val Glu Ile Lys
1               5                   10

<210> SEQ ID NO 78
<211> LENGTH: 25
<212> TYPE: PRT
<213> ORGANISM: Homo sapiens

<400> SEQUENCE: 78

Gln Val Gln Leu Val Gln Ser Gly Ala Glu Val Lys Lys Pro Gly Ser
1               5                   10                  15

Ser Val Lys Val Ser Cys Lys Ala Ser
            20                  25

<210> SEQ ID NO 79
<211> LENGTH: 14
<212> TYPE: PRT
<213> ORGANISM: Homo sapiens

<400> SEQUENCE: 79

Trp Val Arg Gln Ala Pro Gly Gln Gly Leu Glu Trp Met Gly
1               5                   10

<210> SEQ ID NO 80
<211> LENGTH: 32
<212> TYPE: PRT
<213> ORGANISM: Homo sapiens

```
<400> SEQUENCE: 80

Arg Val Thr Ile Thr Ala Asp Lys Ser Thr Ser Thr Ala Tyr Met Glu
1               5                   10                  15

Leu Ser Ser Leu Arg Ser Glu Asp Thr Ala Val Tyr Tyr Cys Ala Arg
                20                  25                  30

<210> SEQ ID NO 81
<211> LENGTH: 11
<212> TYPE: PRT
<213> ORGANISM: Homo sapiens

<400> SEQUENCE: 81

Trp Gly Gln Gly Thr Thr Val Thr Val Ser Ser
1               5                   10

<210> SEQ ID NO 82
<211> LENGTH: 32
<212> TYPE: PRT
<213> ORGANISM: Homo sapiens

<400> SEQUENCE: 82

Gly Val Pro Ser Arg Phe Ser Gly Ser Gly Ser Gly Thr Asp Phe Thr
1               5                   10                  15

Phe Thr Ile Ser Ser Leu Gln Pro Glu Asp Ile Ala Thr Tyr Tyr Cys
                20                  25                  30

<210> SEQ ID NO 83
<211> LENGTH: 25
<212> TYPE: PRT
<213> ORGANISM: Homo sapiens

<400> SEQUENCE: 83

Gln Val Gln Leu Val Gln Ser Gly Ala Glu Val Lys Lys Pro Gly Ala
1               5                   10                  15

Ser Val Lys Val Ser Cys Lys Ala Ser
                20                  25

<210> SEQ ID NO 84
<211> LENGTH: 32
<212> TYPE: PRT
<213> ORGANISM: Homo sapiens

<400> SEQUENCE: 84

Arg Val Thr Met Thr Thr Asp Thr Ser Thr Ser Thr Ala Tyr Met Glu
1               5                   10                  15

Leu Arg Ser Leu Arg Ser Asp Asp Thr Ala Val Tyr Tyr Cys Ala Arg
                20                  25                  30

<210> SEQ ID NO 85
<211> LENGTH: 23
<212> TYPE: PRT
<213> ORGANISM: Homo sapiens

<400> SEQUENCE: 85

Asp Ile Gln Met Thr Gln Ser Pro Ser Thr Leu Ser Ala Ser Val Gly
1               5                   10                  15

Asp Arg Val Thr Ile Thr Cys
                20

<210> SEQ ID NO 86
<211> LENGTH: 32
<212> TYPE: PRT
```

-continued

<213> ORGANISM: Homo sapiens

<400> SEQUENCE: 86

Gly Val Pro Ser Arg Phe Ser Gly Ser Gly Thr Glu Phe Thr
1               5                   10                  15

Leu Thr Ile Ser Ser Leu Gln Pro Asp Asp Phe Ala Thr Tyr Tyr Cys
            20                  25                  30

<210> SEQ ID NO 87
<211> LENGTH: 32
<212> TYPE: PRT
<213> ORGANISM: Homo sapiens

<400> SEQUENCE: 87

Arg Val Thr Met Thr Arg Asp Thr Ser Thr Ser Thr Val Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 88
<211> LENGTH: 193
<212> TYPE: PRT
<213> ORGANISM: Homo sapiens

<400> SEQUENCE: 88

Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 89
<211> LENGTH: 84
<212> TYPE: PRT
<213> ORGANISM: Homo sapiens

<400> SEQUENCE: 89

Met Ala Leu Ser Ser Gln Ile Trp Ala Ala Cys Leu Leu Leu Leu Leu
1               5                   10                  15

Leu Leu Ala Ser Leu Thr Ser Gly Ser Val Phe Pro Gln Gln Thr Gly
            20                  25                  30

Gln Leu Ala Glu Leu Gln Pro Gln Asp Arg Ala Gly Ala Arg Ala Ser
        35                  40                  45

Trp Met Pro Met Phe Gln Arg Arg Arg Arg Asp Thr His Phe Pro
 50                  55                  60

Ile Cys Ile Phe Cys Cys Gly Cys Cys His Arg Ser Lys Cys Gly Met
 65                  70                  75                  80

Cys Cys Lys Thr

<210> SEQ ID NO 90
<211> LENGTH: 61
<212> TYPE: PRT
<213> ORGANISM: Homo sapiens

<400> SEQUENCE: 90

Gly Ser Val Phe Pro Gln Gln Thr Gly Gln Leu Ala Glu Leu Gln Pro
 1               5                  10                  15

Gln Asp Arg Ala Gly Ala Arg Ala Ser Trp Met Pro Met Phe Gln Arg
            20                  25                  30

Arg Arg Arg Arg Asp Thr His Phe Pro Ile Cys Ile Phe Cys Cys Gly
        35                  40                  45

Cys Cys His Arg Ser Lys Cys Gly Met Cys Cys Lys Thr
     50                  55                  60

<210> SEQ ID NO 91
<211> LENGTH: 25
<212> TYPE: PRT
<213> ORGANISM: HOMO SAPIENS

<400> SEQUENCE: 91

Asp Thr His Phe Pro Ile Cys Ile Phe Cys Cys Gly Cys Cys His Arg
 1               5                  10                  15

Ser Lys Cys Gly Met Cys Cys Lys Thr
            20                  25

<210> SEQ ID NO 92
<211> LENGTH: 25
<212> TYPE: PRT
<213> ORGANISM: MONKEY

<400> SEQUENCE: 92

Asp Thr His Phe Pro Ile Cys Ile Phe Cys Cys Gly Cys Cys His Arg
 1               5                  10                  15

Ser Lys Cys Gly Met Cys Cys Arg Thr
            20                  25

<210> SEQ ID NO 93
<211> LENGTH: 25
<212> TYPE: PRT
<213> ORGANISM: RATTUS SP

<400> SEQUENCE: 93

Asp Thr Asn Phe Pro Ile Cys Leu Phe Cys Cys Lys Cys Cys Lys Asn
 1               5                  10                  15

Ser Ser Cys Gly Leu Cys Cys Ile Thr
            20                  25

<210> SEQ ID NO 94
<211> LENGTH: 25

```
<212> TYPE: PRT
<213> ORGANISM: MUS SP

<400> SEQUENCE: 94

Asp Thr Asn Phe Pro Ile Cys Ile Phe Cys Cys Lys Cys Cys Asn Asn
1               5                   10                  15

Ser Gln Cys Gly Ile Cys Cys Lys Thr
            20                  25

<210> SEQ ID NO 95
<211> LENGTH: 7
<212> TYPE: PRT
<213> ORGANISM: Homo sapiens

<400> SEQUENCE: 95

Arg Ser Arg Phe Ile Gln Gly
1               5

<210> SEQ ID NO 96
<211> LENGTH: 24
<212> TYPE: PRT
<213> ORGANISM: Artificial
<220> FEATURE:
<223> OTHER INFORMATION: Synthetic

<400> SEQUENCE: 96

Gly Gly Ser Pro Phe Glu Asp Ile Arg Ser Arg Phe Ile Gln Gly Glu
1               5                   10                  15

Ser Ile Thr Pro Thr Lys Gly Cys
            20

<210> SEQ ID NO 97
<211> LENGTH: 16
<212> TYPE: PRT
<213> ORGANISM: Artificial
<220> FEATURE:
<223> OTHER INFORMATION: Synthetic

<400> SEQUENCE: 97

Gly Gly Ser Pro Phe Glu Asp Ile Arg Ser Arg Phe Ile Gln Gly Cys
1               5                   10                  15

<210> SEQ ID NO 98
<211> LENGTH: 21
<212> TYPE: PRT
<213> ORGANISM: Artificial
<220> FEATURE:
<223> OTHER INFORMATION: Synthetic

<400> SEQUENCE: 98

Gly Gly Ile Gln Gly Glu Ser Ile Thr Pro Thr Lys Ile Pro Glu Ile
1               5                   10                  15

Thr Thr Glu Gly Cys
            20

<210> SEQ ID NO 99
<211> LENGTH: 19
<212> TYPE: PRT
<213> ORGANISM: Artificial
<220> FEATURE:
<223> OTHER INFORMATION: Synthetic

<400> SEQUENCE: 99

Gly Gly Met Pro Gly Ser Pro Leu Asp Leu Ser Val Ser Pro Phe Glu
1               5                   10                  15
```

Asp Gly Cys

<210> SEQ ID NO 100
<211> LENGTH: 19
<212> TYPE: PRT
<213> ORGANISM: Artificial
<220> FEATURE:
<223> OTHER INFORMATION: Synthetic

<400> SEQUENCE: 100

Gly Gly Ser Pro Leu Asp Leu Ser Val Ser Pro Phe Glu Asp Ile Arg
1               5                   10                  15

Ser Gly Cys

<210> SEQ ID NO 101
<211> LENGTH: 18
<212> TYPE: PRT
<213> ORGANISM: Artificial
<220> FEATURE:
<223> OTHER INFORMATION: Synthetic

<400> SEQUENCE: 101

Gly Gly Glu Asp Ile Arg Ser Arg Phe Ile Gln Gly Glu Ser Ile Thr
1               5                   10                  15

Gly Cys

<210> SEQ ID NO 102
<211> LENGTH: 18
<212> TYPE: PRT
<213> ORGANISM: Artificial
<220> FEATURE:
<223> OTHER INFORMATION: Synthetic

<400> SEQUENCE: 102

Gly Gly Arg Ser Arg Phe Ile Gln Gly Glu Ser Ile Thr Pro Thr Lys
1               5                   10                  15

Gly Cys

<210> SEQ ID NO 103
<211> LENGTH: 10
<212> TYPE: PRT
<213> ORGANISM: Artificial
<220> FEATURE:
<223> OTHER INFORMATION: Synthetic

<400> SEQUENCE: 103

Gly Arg Ala Phe Thr Ser Phe Leu Ile Glu
1               5                   10

<210> SEQ ID NO 104
<211> LENGTH: 10
<212> TYPE: PRT
<213> ORGANISM: Artificial
<220> FEATURE:
<223> OTHER INFORMATION: Synthetic

<400> SEQUENCE: 104

Gly Lys Ala Phe Thr Ser Phe Leu Ile Glu
1               5                   10

<210> SEQ ID NO 105
<211> LENGTH: 10
<212> TYPE: PRT
<213> ORGANISM: Artificial
<220> FEATURE:
<223> OTHER INFORMATION: Synthetic

```
<400> SEQUENCE: 105

Gly Tyr Arg Phe Thr Ser Phe Leu Ile Glu
1               5                   10

<210> SEQ ID NO 106
<211> LENGTH: 10
<212> TYPE: PRT
<213> ORGANISM: Artificial
<220> FEATURE:
<223> OTHER INFORMATION: Synthetic

<400> SEQUENCE: 106

Gly Tyr Ala Phe Arg Ser Phe Leu Ile Glu
1               5                   10

<210> SEQ ID NO 107
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa is Tyr, Arg, or Lys
<220> FEATURE:
<221> NAME/KEY: MISC_FEATURE
<222> LOCATION: (3)..(3)
<223> OTHER INFORMATION: Xaa is Ala or Arg
<220> FEATURE:
<221> NAME/KEY: MISC_FEATURE
<222> LOCATION: (5)..(5)
<223> OTHER INFORMATION: Xaa is Thr or Arg

<400> SEQUENCE: 107

Gly Xaa Xaa Phe Xaa Ser Phe Leu Ile Glu
1               5                   10

<210> SEQ ID NO 108
<211> LENGTH: 17
<212> TYPE: PRT
<213> ORGANISM: Artificial
<220> FEATURE:
<223> OTHER INFORMATION: Synthetic

<400> SEQUENCE: 108

Thr Ser Asn Pro Arg Thr Arg Gly Thr Lys Tyr Lys Glu Lys Phe Arg
1               5                   10                  15

Gly

<210> SEQ ID NO 109
<211> LENGTH: 17
<212> TYPE: PRT
<213> ORGANISM: Artificial
<220> FEATURE:
<223> OTHER INFORMATION: Synthetic

<400> SEQUENCE: 109

Thr Ser Asn Pro Arg Thr Gly Arg Thr Lys Tyr Lys Glu Lys Phe Arg
1               5                   10                  15

Gly

<210> SEQ ID NO 110
<211> LENGTH: 17
<212> TYPE: PRT
<213> ORGANISM: Artificial
<220> FEATURE:
```

<223> OTHER INFORMATION: Synthetic

<400> SEQUENCE: 110

Thr Ser Asn Pro Arg Thr Gly Gly Arg Lys Tyr Lys Glu Lys Phe Arg
1               5                   10                  15
Gly

<210> SEQ ID NO 111
<211> LENGTH: 17
<212> TYPE: PRT
<213> ORGANISM: Artificial
<220> FEATURE:
<223> OTHER INFORMATION: Synthetic

<400> SEQUENCE: 111

Thr Ser Asn Pro Arg Thr Gly Gly Thr Lys Tyr Lys Thr Lys Phe Arg
1               5                   10                  15
Gly

<210> SEQ ID NO 112
<211> LENGTH: 17
<212> TYPE: PRT
<213> ORGANISM: Artificial
<220> FEATURE:
<223> OTHER INFORMATION: Synthetic

<400> SEQUENCE: 112

Thr Ser Asn Pro Arg Thr Gly Gly Thr Lys Tyr Lys Ser Lys Phe Arg
1               5                   10                  15
Gly

<210> SEQ ID NO 113
<211> LENGTH: 17
<212> TYPE: PRT
<213> ORGANISM: Artificial
<220> FEATURE:
<223> OTHER INFORMATION: Synthetic

<400> SEQUENCE: 113

Thr Ser Asn Pro Arg Thr Gly Gly Thr Lys Tyr Lys Trp Lys Phe Arg
1               5                   10                  15
Gly

<210> SEQ ID NO 114
<211> LENGTH: 17
<212> TYPE: PRT
<213> ORGANISM: Artificial
<220> FEATURE:
<223> OTHER INFORMATION: Synthetic

<400> SEQUENCE: 114

Thr Ser Asn Pro Arg Thr Gly Gly Thr Lys Tyr Lys Glu Val Phe Arg
1               5                   10                  15
Gly

<210> SEQ ID NO 115
<211> LENGTH: 17
<212> TYPE: PRT
<213> ORGANISM: Artificial
<220> FEATURE:
<223> OTHER INFORMATION: Synthetic

<400> SEQUENCE: 115

Thr Ser Asn Pro Arg Thr Gly Gly Thr Lys Tyr Lys Glu Lys Phe Arg

```
                 1               5                  10                 15
Arg

<210> SEQ ID NO 116
<211> LENGTH: 17
<212> TYPE: PRT
<213> ORGANISM: Artificial
<220> FEATURE:
<223> OTHER INFORMATION: Synthetic

<400> SEQUENCE: 116

Thr Ser Asn Pro Arg Thr Gly Arg Thr Lys Tyr Lys Ser Lys Phe Arg
1               5                   10                  15

Gly

<210> SEQ ID NO 117
<211> LENGTH: 17
<212> TYPE: PRT
<213> ORGANISM: Artificial
<220> FEATURE:
<223> OTHER INFORMATION: Synthetic

<400> SEQUENCE: 117

Thr Ser Asn Pro Arg Thr Gly Arg Thr Lys Tyr Lys Thr Lys Phe Arg
1               5                   10                  15

Gly

<210> SEQ ID NO 118
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Xaa is Gly or Arg
<220> FEATURE:
<221> NAME/KEY: MISC_FEATURE
<222> LOCATION: (8)..(8)
<223> OTHER INFORMATION: Xaa is Gly or Arg
<220> FEATURE:
<221> NAME/KEY: MISC_FEATURE
<222> LOCATION: (9)..(9)
<223> OTHER INFORMATION: Xaa is Thr or Arg
<220> FEATURE:
<221> NAME/KEY: MISC_FEATURE
<222> LOCATION: (13)..(13)
<223> OTHER INFORMATION: Xaa is Glu, Thr, Ser, or Trp
<220> FEATURE:
<221> NAME/KEY: MISC_FEATURE
<222> LOCATION: (14)..(14)
<223> OTHER INFORMATION: Xaa is Lys or Val
<220> FEATURE:
<221> NAME/KEY: MISC_FEATURE
<222> LOCATION: (17)..(17)
<223> OTHER INFORMATION: Xaa is Gly or Arg

<400> SEQUENCE: 118

Thr Ser Asn Pro Arg Thr Xaa Xaa Xaa Lys Tyr Lys Xaa Xaa Phe Arg
1               5                   10                  15

Xaa

<210> SEQ ID NO 119
<211> LENGTH: 5
<212> TYPE: PRT
<213> ORGANISM: Artificial
<220> FEATURE:
<223> OTHER INFORMATION: Synthetic
```

```
<400> SEQUENCE: 119

Glu Phe Phe Val Tyr
1               5

<210> SEQ ID NO 120
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is Asp or Val

<400> SEQUENCE: 120

Glu Phe Phe Xaa Tyr
1               5

<210> SEQ ID NO 121
<211> LENGTH: 7
<212> TYPE: PRT
<213> ORGANISM: Artificial
<220> FEATURE:
<223> OTHER INFORMATION: Synthetic

<400> SEQUENCE: 121

Ala Gly Ser Lys Arg His Ser
1               5

<210> SEQ ID NO 122
<211> LENGTH: 7
<212> TYPE: PRT
<213> ORGANISM: Artificial
<220> FEATURE:
<223> OTHER INFORMATION: Synthetic

<400> SEQUENCE: 122

Ala Gly Ser Lys Leu Arg Ser
1               5

<210> SEQ ID NO 123
<211> LENGTH: 7
<212> TYPE: PRT
<213> ORGANISM: Artificial
<220> FEATURE:
<223> OTHER INFORMATION: Synthetic

<400> SEQUENCE: 123

Ala Gly Ser Lys Leu Val Ser
1               5

<210> SEQ ID NO 124
<211> LENGTH: 7
<212> TYPE: PRT
<213> ORGANISM: Artificial
<220> FEATURE:
<223> OTHER INFORMATION: Synthetic

<400> SEQUENCE: 124

Ala Gly Ser Lys Leu Tyr Ser
1               5

<210> SEQ ID NO 125
<211> LENGTH: 7
<212> TYPE: PRT
<213> ORGANISM: Artificial
```

```
<220> FEATURE:
<223> OTHER INFORMATION: Synthetic

<400> SEQUENCE: 125

Ala Gly Ser Lys Leu His Trp
1               5

<210> SEQ ID NO 126
<211> LENGTH: 7
<212> TYPE: PRT
<213> ORGANISM: Artificial
<220> FEATURE:
<223> OTHER INFORMATION: Synthetic

<400> SEQUENCE: 126

Ala Gly Ser Lys Leu His Tyr
1               5

<210> SEQ ID NO 127
<211> LENGTH: 7
<212> TYPE: PRT
<213> ORGANISM: Artificial
<220> FEATURE:
<223> OTHER INFORMATION: Synthetic

<400> SEQUENCE: 127

Ala Gly Ser Lys Arg His Trp
1               5

<210> SEQ ID NO 128
<211> LENGTH: 7
<212> TYPE: PRT
<213> ORGANISM: Artificial
<220> FEATURE:
<223> OTHER INFORMATION: Synthetic

<400> SEQUENCE: 128

Ala Gly Ser Lys Arg Tyr Tyr
1               5

<210> SEQ ID NO 129
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Xaa is Leu or Arg
<220> FEATURE:
<221> NAME/KEY: MISC_FEATURE
<222> LOCATION: (6)..(6)
<223> OTHER INFORMATION: Xaa is His, Arg, Val, or Tyr
<220> FEATURE:
<221> NAME/KEY: MISC_FEATURE
<222> LOCATION: (7)..(7)
<223> OTHER INFORMATION: Xaa is Ser, Trp, or Tyr

<400> SEQUENCE: 129

Ala Gly Ser Lys Xaa Xaa Xaa
1               5

<210> SEQ ID NO 130
<211> LENGTH: 114
<212> TYPE: PRT
<213> ORGANISM: Artificial
<220> FEATURE:
<223> OTHER INFORMATION: Synthetic
```

<400> SEQUENCE: 130

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Ser Phe
            20                  25                  30

Leu Ile Glu Trp Val Arg Gln Ala Pro Gly Gln Gly Leu Glu Trp Met
        35                  40                  45

Gly Thr Ser Asn Pro Arg Thr Gly Arg Thr Lys Tyr Ser Lys Phe
50                  55                  60

Arg Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Phe Phe Asp Tyr Trp Gly Gln Gly Thr Thr Val Thr Val
            100                 105                 110

Ser Ser
```

<210> SEQ ID NO 131
<211> LENGTH: 342
<212> TYPE: DNA
<213> ORGANISM: Artificial
<220> FEATURE:
<223> OTHER INFORMATION: Synthetic

<400> SEQUENCE: 131

```
caggtgcagc tggtgcagtc tggggctgag gtgaagaagc ctgggtcctc agtgaaggtt      60
tcctgcaagg catctggcta cgccttcact tcgttcttga tagagtgggt gcgacaggcc     120
cctggacaag gccttgagtg gatgggaacg agtaatccta ggactgggag gacgaagtat     180
aaatccaagt tcaggggcag agtcaccatt accgcggaca aatccacgag cacagcctac     240
atggagctga gcagcctgag atctgaggac acggccgtgt attactgtgc gcgcgagttt     300
tttgactact ggggccaagg aaccacggtc accgtctcct ca                        342
```

<210> SEQ ID NO 132
<211> LENGTH: 107
<212> TYPE: PRT
<213> ORGANISM: Artificial
<220> FEATURE:
<223> OTHER INFORMATION: Synthetic

<400> SEQUENCE: 132

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Ile Ser Lys Tyr
            20                  25                  30

Thr Ala Trp Tyr Gln Gln Lys Pro Gly Lys Ala Pro Lys Leu Leu Ile
        35                  40                  45

Tyr Ala Gly Ser Lys Arg His Trp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asn Glu Tyr Pro Tyr
                85                  90                  95

Thr Phe Gly Gly Gly Thr Lys Val Glu Ile Lys
            100                 105
```

<210> SEQ ID NO 133

<211> LENGTH: 321
<212> TYPE: DNA
<213> ORGANISM: Artificial
<220> FEATURE:
<223> OTHER INFORMATION: Synthetic

<400> SEQUENCE: 133

```
gacatccaga tgacccagtc tccatcctcc ctgtctgcat ctgtaggaga cagagtcacc      60
atcacttgca gggcgagtaa gagcattagc aaatatacag cctggtatca gcagaaacca     120
gggaaagccc ctaagctcct gatctatgct gggtccaagc ggcactgggg agtcccatca     180
aggttcagtg gcagtggatc tgggacagat ttcactctca ccatcagcag tctgcaacct     240
gaagattttg caacttacta ttgtcaacaa cataatgaat acccgtacac gttcggcgga     300
gggaccaagg tggagatcaa a                                                321
```

<210> SEQ ID NO 134
<211> LENGTH: 114
<212> TYPE: PRT
<213> ORGANISM: Artificial
<220> FEATURE:
<223> OTHER INFORMATION: Synthetic

<400> SEQUENCE: 134

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Ser Phe
            20                  25                  30

Leu Ile Glu Trp Val Arg Gln Ala Pro Gly Gln Gly Leu Glu Trp Met
        35                  40                  45

Gly Thr Ser Asn Pro Arg Thr Gly Gly Arg Lys Tyr Lys Glu Lys Phe
    50                  55                  60

Arg Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Phe Phe Asp Tyr Trp Gly Gln Gly Thr Thr Val Thr Val
            100                 105                 110

Ser Ser

<210> SEQ ID NO 135
<211> LENGTH: 342
<212> TYPE: DNA
<213> ORGANISM: Artificial
<220> FEATURE:
<223> OTHER INFORMATION: Synthetic

<400> SEQUENCE: 135

```
caggtgcagc tggtgcagtc tggggctgag gtgaagaagc ctgggtcctc agtgaaggtt      60
tcctgcaagg catctggcta cgccttcact tcgttcttga tagagtgggt gcgacaggcc     120
cctggacaag gccttgagtg gatgggaacg agtaatccta ggactggtgg tcggaagtat     180
aaagagaagt tcaggggcag agtcaccatt accgcggaca aatccacgag cacagcctac     240
atggagctga gcagcctgag atctgaggac acggccgtgt attactgtgc gcgcgagttt     300
tttgactact ggggccaagg aaccacggtc accgtctcct ca                        342
```

<210> SEQ ID NO 136
<211> LENGTH: 107
<212> TYPE: PRT
<213> ORGANISM: Artificial
<220> FEATURE:
<223> OTHER INFORMATION: Synthetic

<400> SEQUENCE: 136

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Ile Ser Lys Tyr
            20                  25                  30

Thr Ala Trp Tyr Gln Gln Lys Pro Gly Lys Ala Pro Lys Leu Leu Ile
        35                  40                  45

Tyr Ala Gly Ser Lys Leu His Trp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asn Glu Tyr Pro Tyr
                85                  90                  95

Thr Phe Gly Gly Gly Thr Lys Val Glu Ile Lys
            100                 105

<210> SEQ ID NO 137
<211> LENGTH: 321
<212> TYPE: DNA
<213> ORGANISM: Artificial
<220> FEATURE:
<223> OTHER INFORMATION: Synthetic

<400> SEQUENCE: 137
gacatccaga tgacccagtc tccatcctcc ctgtctgcat ctgtaggaga cagagtcacc        60
atcacttgca gggcgagtaa gagcattagc aaatatacag cctggtatca gcagaaacca       120
gggaaagccc ctaagctcct gatctatgct gggtccaagc tgcactgggg agtcccatca       180
aggttcagtg gcagtggatc tgggacagat ttcactctca ccatcagcag tctgcaacct       240
gaagattttg caacttacta ttgtcaacaa cataatgaat acccgtacac gttcggcgga       300
gggaccaagg tggagatcaa a                                                 321

<210> SEQ ID NO 138
<211> LENGTH: 114
<212> TYPE: PRT
<213> ORGANISM: Artificial
<220> FEATURE:
<223> OTHER INFORMATION: Synthetic

<400> SEQUENCE: 138

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Ser Phe
            20                  25                  30

Leu Ile Glu Trp Val Arg Gln Ala Pro Gly Gln Gly Leu Glu Trp Met
        35                  40                  45

Gly Thr Ser Asn Pro Arg Thr Gly Gly Arg Lys Tyr Lys Glu Lys Phe
    50                  55                  60

Arg Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Phe Phe Asp Tyr Trp Gly Gln Gly Thr Thr Val Thr Val
            100                 105                 110

Ser Ser

<210> SEQ ID NO 139
<211> LENGTH: 342
<212> TYPE: DNA
<213> ORGANISM: Artificial
<220> FEATURE:
<223> OTHER INFORMATION: Synthetic

<400> SEQUENCE: 139

| caggtgcagc | tggtgcagtc | tggggctgag | gtgaagaagc | tggggtcctc | agtgaaggtt | 60 |
| tcctgcaagg | catctggcta | cgccttcact | tcgttcttga | tagagtgggt | gcgacaggcc | 120 |
| cctggacaag | ggcttgagtg | gatgggaacg | agtaatccta | ggactggggg | gaggaagtat | 180 |
| aaagagaagt | tcaggggag | agtcaccatt | accgcggaca | aatccacgag | cacagcctac | 240 |
| atggagctga | gcagcctgag | atctgaggac | acggccgtgt | attactgtgc | gcgcgagttt | 300 |
| tttgactact | ggggccaagg | aaccacggtc | accgtctcct | ca | | 342 |

<210> SEQ ID NO 140
<211> LENGTH: 107
<212> TYPE: PRT
<213> ORGANISM: Artificial
<220> FEATURE:
<223> OTHER INFORMATION: Synthetic

<400> SEQUENCE: 140

Asp Ile Gln Met Thr Gln Ser Pro Ser Ser Leu Ser Ala Ser Val Gly
1               5                   10                  15
Asp Arg Val Thr Ile Thr Cys Arg Ala Ser Lys Ser Ile Ser Lys Tyr
            20                  25                  30
Thr Ala Trp Tyr Gln Gln Lys Pro Gly Lys Ala Pro Lys Leu Leu Ile
        35                  40                  45
Tyr Ala Gly Ser Lys Leu Arg Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln His Asn Glu Tyr Pro Tyr
                85                  90                  95
Thr Phe Gly Gly Gly Thr Lys Val Glu Ile Lys
            100                 105

<210> SEQ ID NO 141
<211> LENGTH: 321
<212> TYPE: DNA
<213> ORGANISM: Artificial
<220> FEATURE:
<223> OTHER INFORMATION: Synthetic

<400> SEQUENCE: 141

| gacatccaga | tgacccagtc | tccatcctcc | ctgtctgcat | ctgtaggaga | cagagtcacc | 60 |
| atcacttgca | gggcgagtaa | gagcattagc | aaatatacag | cctggtatca | gcagaaacca | 120 |
| gggaaagccc | ctaagctcct | gatctatgct | ggtccaagt | tgcggtctgg | agtcccatca | 180 |
| aggttcagtg | gcagtggatc | tgggacagat | ttcactctca | ccatcagcag | tctgcaacct | 240 |
| gaagattttg | caacttacta | ttgtcaacaa | cataatgaat | acccgtacac | gttcggcgga | 300 |
| gggaccaagg | tggagatcaa | a | | | | 321 |

<210> SEQ ID NO 142
<211> LENGTH: 114
<212> TYPE: PRT

<213> ORGANISM: Artificial
<220> FEATURE:
<223> OTHER INFORMATION: Synthetic

<400> SEQUENCE: 142

Gln Val Gln Leu Val Gln Ser Gly Ala Glu Val Lys Lys Pro Gly Ser
1               5                   10                  15
Ser Val Lys Val Ser Cys Lys Ala Ser Gly Tyr Arg Phe Thr Ser Phe
            20                  25                  30
Leu Ile Glu Trp Val Arg Gln Ala Pro Gly Gln Gly Leu Glu Trp Met
        35                  40                  45
Gly Thr Ser Asn Pro Arg Thr Gly Arg Thr Lys Tyr Lys Thr Lys Phe
    50                  55                  60
Arg Gly Arg Val Thr Ile Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Glu Phe Phe Asp Tyr Trp Gly Gln Gly Thr Thr Val Thr Val
            100                 105                 110
Ser Ser

<210> SEQ ID NO 143
<211> LENGTH: 342
<212> TYPE: DNA
<213> ORGANISM: Artificial
<220> FEATURE:
<223> OTHER INFORMATION: Synthetic

<400> SEQUENCE: 143
caggtgcagc tggtgcagtc tggggctgag gtgaagaagc ctgggtcctc agtgaaggtt      60
tcctgcaagg catctggcta ccgcttcact tcgttcttga tagagtgggt gcgacaggcc     120
cctggacaag gcttgagtg gatgggaacg agtaatccta ggactggtag acaaagtat      180
aaaaccaagt tcaggggcag agtcaccatt accgcggaca atccacgag cacagcctac     240
atggagctga gcagcctgag atctgaggac acggccgtgt attactgtgc gcgcgagttt     300
tttgactact ggggccaagg aaccacggtc accgtctcct ca                        342

<210> SEQ ID NO 144
<211> LENGTH: 107
<212> TYPE: PRT
<213> ORGANISM: Artificial
<220> FEATURE:
<223> OTHER INFORMATION: Synthetic

<400> SEQUENCE: 144

Asp Ile Gln Met Thr Gln Ser Pro Ser Ser Leu Ser Ala Ser Val Gly
1               5                   10                  15
Asp Arg Val Thr Ile Thr Cys Arg Ala Ser Lys Ser Ile Ser Lys Tyr
            20                  25                  30
Thr Ala Trp Tyr Gln Gln Lys Pro Gly Lys Ala Pro Lys Leu Leu Ile
        35                  40                  45
Tyr Ala Gly Ser Lys Arg Tyr Tyr Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln His Asn Glu Tyr Pro Tyr
                85                  90                  95
Thr Phe Gly Gly Gly Thr Lys Val Glu Ile Lys

<210> SEQ ID NO 145
<211> LENGTH: 321
<212> TYPE: DNA
<213> ORGANISM: Artificial
<220> FEATURE:
<223> OTHER INFORMATION: Synthetic

<400> SEQUENCE: 145

```
gacatccaga tgacccagtc tccatcctcc ctgtctgcat ctgtaggaga cagagtcacc    60
atcacttgca gggcgagtaa gagcattagc aaatatacag cctggtatca gcagaaacca   120
gggaaagccc ctaagctcct gatctatgct gggtccaagc ggtactacgg agtcccatca   180
aggttcagtg gcagtggatc tgggacagat ttcactctca ccatcagcag tctgcaacct   240
gaagattttg caacttacta ttgtcaacaa cataatgaat acccgtacac gttcggcgga   300
gggaccaagg tggagatcaa a                                             321
```

<210> SEQ ID NO 146
<211> LENGTH: 114
<212> TYPE: PRT
<213> ORGANISM: Artificial
<220> FEATURE:
<223> OTHER INFORMATION: Synthetic

<400> SEQUENCE: 146

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Arg Phe Thr Ser Phe
            20                  25                  30

Leu Ile Glu Trp Val Arg Gln Ala Pro Gly Gln Gly Leu Glu Trp Met
        35                  40                  45

Gly Thr Ser Asn Pro Arg Thr Gly Gly Thr Lys Tyr Lys Glu Lys Phe
    50                  55                  60

Arg Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Phe Phe Val Tyr Trp Gly Gln Gly Thr Thr Val Thr Val
            100                 105                 110

Ser Ser
```

<210> SEQ ID NO 147
<211> LENGTH: 342
<212> TYPE: DNA
<213> ORGANISM: Artificial
<220> FEATURE:
<223> OTHER INFORMATION: Synthetic

<400> SEQUENCE: 147

```
caggtgcagc tggtgcagtc tggggctgag gtgaagaagc ctgggtcctc agtgaaggtt    60
tcctgcaagg catctggcta ccgcttcact tcgttcttga tagagtgggt gcgacaggcc   120
cctggacaag gcttgagtg gatgggaacg agtaatccta ggactggtgg acaaagtat    180
aaagagaagt tcaggggcag agtcaccatt accgcggaca aatccacgag cacagcctac   240
atggagctga gcagcctgag atctgaggac acggccgtgt attactgtgc gcgcgagttt   300
tttgtctact ggggccaagg aaccacggtc accgtctcct ca                      342
```

```
<210> SEQ ID NO 148
<211> LENGTH: 107
<212> TYPE: PRT
<213> ORGANISM: Artificial
<220> FEATURE:
<223> OTHER INFORMATION: Synthetic

<400> SEQUENCE: 148

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Ile Ser Lys Tyr
            20                  25                  30

Thr Ala Trp Tyr Gln Gln Lys Pro Gly Lys Ala Pro Lys Leu Leu Ile
        35                  40                  45

Tyr Ala Gly Ser Lys Arg Tyr Tyr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asn Glu Tyr Pro Tyr
                85                  90                  95

Thr Phe Gly Gly Gly Thr Lys Val Glu Ile Lys
            100                 105

<210> SEQ ID NO 149
<211> LENGTH: 321
<212> TYPE: DNA
<213> ORGANISM: Artificial
<220> FEATURE:
<223> OTHER INFORMATION: Synthetic

<400> SEQUENCE: 149
gacatccaga tgacccagtc tccatcctcc ctgtctgcat ctgtaggaga cagagtcacc    60
atcacttgca gggcgagtaa gagcattagc aaatatacag cctggtatca gcagaaacca   120
gggaaagccc ctaagctcct gatctatgct gggtccaagc ggtactacgg agtcccatca   180
aggttcagtg gcagtggatc tgggacagat ttcactctca ccatcagcag tctgcaacct   240
gaagattttg caacttacta ttgtcaacaa cataatgaat acccgtacac gttcggcgga   300
gggaccaagg tggagatcaa a                                             321

<210> SEQ ID NO 150
<211> LENGTH: 440
<212> TYPE: PRT
<213> ORGANISM: Artificial
<220> FEATURE:
<223> OTHER INFORMATION: Synthetic

<400> SEQUENCE: 150

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Ser Phe
            20                  25                  30

Leu Ile Glu Trp Val Arg Gln Ala Pro Gly Gln Gly Leu Glu Trp Met
        35                  40                  45

Gly Thr Ser Asn Pro Arg Thr Gly Arg Thr Lys Tyr Lys Ser Lys Phe
    50                  55                  60

Arg Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

```
Ala Arg Glu Phe Phe Asp Tyr Trp Gly Gln Gly Thr Thr Val Thr Val
            100                 105                 110

Ser Ser Ala Ser Thr Lys Gly Pro Ser Val Phe Pro Leu Ala Pro Cys
        115                 120                 125

Ser Arg Ser Thr Ser Glu Ser Thr Ala Ala Leu Gly Cys Leu Val Lys
130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Lys Thr Tyr Thr Cys Asn Val Asp His Lys Pro Ser Asn Thr Lys Val
        195                 200                 205

Asp Lys Arg Val Glu Ser Lys Tyr Gly Pro Pro Cys Pro Pro Cys Pro
210                 215                 220

Ala Pro Glu Ala Ala Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser Gln Glu Asp Pro Glu Val Gln Phe Asn Trp Tyr
            260                 265                 270

Val Asp Gly Val Glu Val His Asn Ala Lys Thr Lys Pro Arg Glu Glu
        275                 280                 285

Gln Phe Asn Ser Thr Tyr Arg Val Val Ser Val Leu Thr Val Leu His
290                 295                 300

Gln Asp Trp Leu Asn Gly Lys Glu Tyr Lys Cys Lys Val Ser Asn Lys
305                 310                 315                 320

Gly Leu Pro Ser Ser Ile Glu Lys Thr Ile Ser Lys Ala Lys Gly Gln
                325                 330                 335

Pro Arg Glu Pro Gln Val Tyr Thr Leu Pro Pro Ser Gln Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
370                 375                 380

Tyr Lys Thr Thr Pro Pro Val Leu Asp Ser Asp Gly Ser Phe Phe Leu
385                 390                 395                 400

Tyr Ser Arg Leu Thr Val Asp Lys Ser Arg Trp Gln Glu Gly Asn Val
                405                 410                 415

Phe Ser Cys Ser Val Met His Glu Ala Leu His Asn His Tyr Thr Gln
            420                 425                 430

Lys Ser Leu Ser Leu Ser Leu Gly
        435                 440

<210> SEQ ID NO 151
<211> LENGTH: 214
<212> TYPE: PRT
<213> ORGANISM: Artificial
<220> FEATURE:
<223> OTHER INFORMATION: Synthetic

<400> SEQUENCE: 151

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Ile Ser Lys Tyr
```

```
            20                  25                  30
Thr Ala Trp Tyr Gln Gln Lys Pro Gly Lys Ala Pro Lys Leu Leu Ile
        35                  40                  45

Tyr Ala Gly Ser Lys Arg His Trp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asn Glu Tyr Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 152
<211> LENGTH: 440
<212> TYPE: PRT
<213> ORGANISM: Artificial
<220> FEATURE:
<223> OTHER INFORMATION: Synthetic

<400> SEQUENCE: 152

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Ser Phe
            20                  25                  30

Leu Ile Glu Trp Val Arg Gln Ala Pro Gly Gln Gly Leu Glu Trp Met
        35                  40                  45

Gly Thr Ser Asn Pro Arg Thr Gly Gly Arg Lys Tyr Lys Glu Lys Phe
    50                  55                  60

Arg Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Phe Phe Asp Tyr Trp Gly Gln Gly Thr Val Thr Val
            100                 105                 110

Ser Ser Ala Ser Thr Lys Gly Pro Ser Val Phe Pro Leu Ala Pro Cys
        115                 120                 125

Ser Arg Ser Thr Ser Glu Ser Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175
```

```
Tyr Ser Leu Ser Ser Val Val Thr Val Pro Ser Ser Leu Gly Thr
            180                 185                 190

Lys Thr Tyr Thr Cys Asn Val Asp His Lys Pro Ser Asn Thr Lys Val
        195                 200                 205

Asp Lys Arg Val Glu Ser Lys Tyr Gly Pro Pro Cys Pro Pro Cys Pro
210                 215                 220

Ala Pro Glu Ala Ala Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
            245                 250                 255

Val Val Asp Val Ser Gln Glu Asp Pro Glu Val Gln Phe Asn Trp Tyr
            260                 265                 270

Val Asp Gly Val Glu Val His Asn Ala Lys Thr Lys Pro Arg Glu Glu
            275                 280                 285

Gln Phe Asn Ser Thr Tyr Arg Val Val Ser Val Leu Thr Val Leu His
        290                 295                 300

Gln Asp Trp Leu Asn Gly Lys Glu Tyr Lys Cys Lys Val Ser Asn Lys
305                 310                 315                 320

Gly Leu Pro Ser Ser Ile Glu Lys Thr Ile Ser Lys Ala Lys Gly Gln
            325                 330                 335

Pro Arg Glu Pro Gln Val Tyr Thr Leu Pro Pro Ser Gln Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
370                 375                 380

Tyr Lys Thr Thr Pro Pro Val Leu Asp Ser Asp Gly Ser Phe Phe Leu
385                 390                 395                 400

Tyr Ser Arg Leu Thr Val Asp Lys Ser Arg Trp Gln Glu Gly Asn Val
            405                 410                 415

Phe Ser Cys Ser Val Met His Glu Ala Leu His Asn His Tyr Thr Gln
            420                 425                 430

Lys Ser Leu Ser Leu Ser Leu Gly
        435                 440

<210> SEQ ID NO 153
<211> LENGTH: 1320
<212> TYPE: DNA
<213> ORGANISM: Artificial
<220> FEATURE:
<223> OTHER INFORMATION: Synthetic

<400> SEQUENCE: 153
caggtgcagc tggtgcagtc tggggctgag gtgaagaagc ctgggtcctc agtgaaggtt      60
tcctgcaagg catctggcta cgccttcact tcgttcttga tagagtgggt gcgacaggcc     120
cctggacaag ggcttgagtg gatgggaacg agtaatccta ggactggtgg tcggaagtat     180
aaagagaagt tcagggcag agtcaccatt accgcggaca atccacgag cacagcctac       240 atggagctga gcagcctgag atctgaggac acggccgtgt attactgtgc gcgcgagttt     300
tttgactact ggggccaagg aaccacggtc accgtctcct cagcctccac caagggccca     360
tcggtcttcc cgctagcgcc tgctccagg agcacctccg agagcacagc cgccctgggc      420
tgcctggtca aggactactt ccccgaaccg gtgacggtgt cgtggaactc aggcgccctg     480
accagcggcg tgcacacctt cccggctgtc ctacagtcct caggactcta ctccctcagc     540
```

-continued

```
agcgtggtga ccgtgccctc cagcagcttg gcacgaaga cctacacctg caacgtagat    600
cacaagccca gcaacaccaa ggtggacaag agagttgagt ccaaatatgg tcccccatgc    660
ccaccctgcc cagcacctga ggccgccggg ggaccatcag tcttcctgtt ccccccaaaa    720
cccaaggaca ctctcatgat ctcccggacc cctgaggtca cgtgcgtggt ggtggacgtg    780
agccaggaag accccgaggt ccagttcaac tggtacgtgg atggcgtgga ggtgcataat    840
gccaagacaa agccgcggga ggagcagttc aacagcacgt accgtgtggt cagcgtcctc    900
accgtcctgc accaggactg gctgaacggc aaggagtaca agtgcaaggt ctccaacaaa    960
ggcctcccgt cctccatcga gaaaaccatc tccaaagcca agggcagccc cgagagcca   1020
caggtgtaca ccctgccccc atcccaggag gagatgacca agaaccaggt cagcctgacc   1080
tgcctggtca aaggcttcta ccccagcgac atcgccgtgg agtgggaaag caatgggcag   1140
ccggagaaca actacaagac cacgcctccc gtgctggact ccgacggctc cttcttcctc   1200
tacagcaggc taaccgtgga caagagcagg tggcaggagg ggaatgtctt ctcatgctcc   1260
gtgatgcatg aggctctgca caaccactac acacagaaga gcctctccct gtctctgggt   1320
```

<210> SEQ ID NO 154
<211> LENGTH: 214
<212> TYPE: PRT
<213> ORGANISM: Artificial
<220> FEATURE:
<223> OTHER INFORMATION: Synthetic

<400> SEQUENCE: 154

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Ile Ser Lys Tyr
            20                  25                  30

Thr Ala Trp Tyr Gln Gln Lys Pro Gly Lys Ala Pro Lys Leu Leu Ile
        35                  40                  45

Tyr Ala Gly Ser Lys Leu His Trp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asn Glu Tyr Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 155

<211> LENGTH: 642
<212> TYPE: DNA
<213> ORGANISM: Artificial
<220> FEATURE:
<223> OTHER INFORMATION: Synthetic

<400> SEQUENCE: 155

```
gacatccaga tgacccagtc tccatcctcc ctgtctgcat ctgtaggaga cagagtcacc    60
atcacttgca gggcgagtaa gagcattagc aaatatacag cctggtatca gcagaaacca   120
gggaaagccc ctaagctcct gatctatgct gggtccaagc tgcactgggg agtcccatca   180
aggttcagtg gcagtggatc tgggacagat ttcactctca ccatcagcag tctgcaacct   240
gaagattttg caacttacta ttgtcaacaa cataatgaat acccgtacac gttcggcgga   300
gggaccaagg tggagatcaa acggactgtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gc                      642
```

<210> SEQ ID NO 156
<211> LENGTH: 440
<212> TYPE: PRT
<213> ORGANISM: Artificial
<220> FEATURE:
<223> OTHER INFORMATION: Synthetic

<400> SEQUENCE: 156

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Ser Phe
            20                  25                  30

Leu Ile Glu Trp Val Arg Gln Ala Pro Gly Gln Gly Leu Glu Trp Met
        35                  40                  45

Gly Thr Ser Asn Pro Arg Thr Gly Gly Arg Lys Tyr Lys Glu Lys Phe
    50                  55                  60

Arg Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Phe Phe Asp Tyr Trp Gly Gln Gly Thr Thr Val Thr Val
            100                 105                 110

Ser Ser Ala Ser Thr Lys Gly Pro Ser Val Phe Pro Leu Ala Pro Cys
        115                 120                 125

Ser Arg Ser Thr Ser Glu Ser Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Lys Thr Tyr Thr Cys Asn Val Asp His Lys Pro Ser Asn Thr Lys Val
        195                 200                 205

Asp Lys Arg Val Glu Ser Lys Tyr Gly Pro Pro Cys Pro Pro Cys Pro
```

```
        210                 215                 220
Ala Pro Glu Ala Ala Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser Gln Glu Asp Pro Glu Val Gln Phe Asn Trp Tyr
            260                 265                 270

Val Asp Gly Val Glu Val His Asn Ala Lys Thr Lys Pro Arg Glu Glu
        275                 280                 285

Gln Phe Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Gly Leu Pro Ser Ser Ile Glu Lys Thr Ile Ser Lys Ala Lys Gly Gln
                325                 330                 335

Pro Arg Glu Pro Gln Val Tyr Thr Leu Pro Pro Ser Gln Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Arg Leu Thr Val Asp Lys Ser Arg Trp Gln Glu Gly Asn Val
                405                 410                 415

Phe Ser Cys Ser Val Met His Glu Ala Leu His Asn His Tyr Thr Gln
            420                 425                 430

Lys Ser Leu Ser Leu Ser Leu Gly
        435                 440

<210> SEQ ID NO 157
<211> LENGTH: 1320
<212> TYPE: DNA
<213> ORGANISM: Artificial
<220> FEATURE:
<223> OTHER INFORMATION: Synthetic

<400> SEQUENCE: 157
caggtgcagc tggtgcagtc tggggctgag gtgaagaagc ctgggtcctc agtgaaggtt      60
tcctgcaagg catctggcta cgccttcact tcgttcttga tagagtgggt gcgacaggcc     120
cctggacaag gcttgagtg gatgggaacg agtaatccta ggactggggg gaggaagtat      180
aaagagaagt tcaggggag agtcaccatt accgcggaca atccacgag cacagcctac       240 atggagctga gcagcctgag atctgaggac acggccgtgt attactgtgc gcgcgagttt     300
tttgactact ggggccaagg aaccacggtc accgtctcct cagcctccac caagggccca    360
tcggtcttcc cgctagcgcc ctgctccagg agcacctccg agagcacagc cgccctgggc    420
tgcctggtca aggactactt ccccgaaccg gtgacggtgt cgtggaactc aggcgccctg    480
accagcggcg tgcacacctt cccggctgtc ctacagtcct caggactcta ctccctcagc    540
agcgtggtga ccgtgccctc agcagcttg gcacgaaga cctacacctg caacgtagat      600
cacaagccca gcaacaccaa ggtggacaag agagttgagt ccaaatatgg tccccccatgc   660 ccaccctgcc cagcacctga ggccgccggg ggaccatcag tcttcctgtt ccccccaaaa    720
cccaaggaca ctctcatgat ctcccggacc cctgaggtca cgtgcgtggt ggtggacgtg    780
```

```
agccaggaag accccgaggt ccagttcaac tggtacgtgg atggcgtgga ggtgcataat    840
gccaagacaa agccgcggga ggagcagttc aacagcacgt accgtgtggt cagcgtcctc    900
accgtcctgc accaggactg gctgaacggc aaggagtaca agtgcaaggt ctccaacaaa    960
ggcctcccgt cctccatcga gaaaaccatc tccaaagcca aagggcagcc ccgagagcca   1020
caggtgtaca ccctgccccc atcccaggag gagatgacca agaaccaggt cagcctgacc   1080
tgcctggtca aaggcttcta ccccagcgac atcgccgtgg agtgggagag caatgggcag   1140
ccggagaaca actacaagac cacgcctccc gtgctggact ccgacggctc cttcttcctc   1200
tacagcaggc taaccgtgga caagagcagg tggcaggagg ggaatgtctt ctcatgctcc   1260
gtgatgcatg aggctctgca caaccactac acacagaaga gcctctccct gtctctgggt   1320
```

<210> SEQ ID NO 158
<211> LENGTH: 214
<212> TYPE: PRT
<213> ORGANISM: Artificial
<220> FEATURE:
<223> OTHER INFORMATION: Synthetic

<400> SEQUENCE: 158

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Ile Ser Lys Tyr
            20                  25                  30

Thr Ala Trp Tyr Gln Gln Lys Pro Gly Lys Ala Pro Lys Leu Leu Ile
        35                  40                  45

Tyr Ala Gly Ser Lys Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asn Glu Tyr Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 159
<211> LENGTH: 642
<212> TYPE: DNA
<213> ORGANISM: Artificial
<220> FEATURE:
<223> OTHER INFORMATION: Synthetic

<400> SEQUENCE: 159

```
gacatccaga tgacccagtc tccatcctcc ctgtctgcat ctgtaggaga cagagtcacc    60
atcacttgca gggcgagtaa gagcattagc aaatatacag cctggtatca gcagaaacca   120
gggaaagccc ctaagctcct gatctatgct gggtccaagt tgcggtctgg agtcccatca   180
aggttcagtg gcagtggatc tgggacagat ttcactctca ccatcagcag tctgcaacct   240
gaagattttg caacttacta ttgtcaacaa cataatgaat acccgtacac gttcggcgga   300
gggaccaagg tggagatcaa acggactgtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gc                     642
```

<210> SEQ ID NO 160
<211> LENGTH: 440
<212> TYPE: PRT
<213> ORGANISM: Artificial
<220> FEATURE:
<223> OTHER INFORMATION: Synthetic

<400> SEQUENCE: 160

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Arg Phe Thr Ser Phe
            20                  25                  30

Leu Ile Glu Trp Val Arg Gln Ala Pro Gly Gln Gly Leu Glu Trp Met
        35                  40                  45

Gly Thr Ser Asn Pro Arg Thr Gly Gly Thr Lys Tyr Lys Glu Lys Phe
    50                  55                  60

Arg Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Phe Phe Val Tyr Trp Gly Gln Gly Thr Thr Val Thr Val
            100                 105                 110

Ser Ser Ala Ser Thr Lys Gly Pro Ser Val Phe Pro Leu Ala Pro Cys
        115                 120                 125

Ser Arg Ser Thr Ser Glu Ser Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Lys Thr Tyr Thr Cys Asn Val Asp His Lys Pro Ser Asn Thr Lys Val
        195                 200                 205

Asp Lys Arg Val Glu Ser Lys Tyr Gly Pro Pro Cys Pro Pro Cys Pro
    210                 215                 220

Ala Pro Glu Ala Ala Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255
```

Val Val Asp Val Ser Gln Glu Asp Pro Glu Val Gln Phe Asn Trp Tyr
            260                 265                 270

Val Asp Gly Val Glu Val His Asn Ala Lys Thr Lys Pro Arg Glu Glu
        275                 280                 285

Gln Phe Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Gly Leu Pro Ser Ser Ile Glu Lys Thr Ile Ser Lys Ala Lys Gly Gln
                325                 330                 335

Pro Arg Glu Pro Gln Val Tyr Thr Leu Pro Pro Ser Gln Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Arg Leu Thr Val Asp Lys Ser Arg Trp Gln Glu Gly Asn Val
                405                 410                 415

Phe Ser Cys Ser Val Met His Glu Ala Leu His Asn His Tyr Thr Gln
            420                 425                 430

Lys Ser Leu Ser Leu Ser Leu Gly
            435                 440

<210> SEQ ID NO 161
<211> LENGTH: 1320
<212> TYPE: DNA
<213> ORGANISM: Artificial
<220> FEATURE:
<223> OTHER INFORMATION: Synthetic

<400> SEQUENCE: 161
caggtgcagc tggtgcagtc tggggctgag gtgaagaagc ctgggtcctc agtgaaggtt     60
tcctgcaagg catctggcta ccgcttcact tcgttcttga tagagtgggt gcgacaggcc    120
cctggacaag ggcttgagtg gatgggaacg agtaatccta ggactggtgg acaaagtat    180 aaagagaagt tcaggggcag agtcaccatt accgcggaca atccacgag cacagcctac    240 atggagctga gcagcctgag atctgaggac acggccgtgt attactgtgc gcgcgagttt    300
tttgtctact ggggccaagg aaccacggtc accgtctcct cagcctccac caagggccca    360
tcggtcttcc cgctagcgcc ctgctccagg agcacctccg agagcacagc cgccctgggc    420
tgcctggtca aggactactt ccccgaaccg gtgacggtgt cgtggaactc aggcgccctg    480
accagcggcg tgcacacctt cccggctgtc ctacagtcct caggactcta ctccctcagc    540
agcgtggtga ccgtgccctc agcagcttg gcacgaaga cctacacctg caacgtagat    600
cacaagccca gcaacaccaa ggtggacaag agagttgagt ccaaatatgg tcccccatgc    660
ccaccctgcc cagcacctga gccgccggg ggaccatcag tcttcctgtt ccccccaaaa    720
cccaaggaca ctctcatgat ctcccggacc cctgaggtca cgtgcgtggt ggtggacgtg    780
agccaggaag accccgaggt ccagttcaac tggtacgtgg atggcgtgga ggtgcataat    840
gccaagacaa agccgcggga ggagcagttc aacagcacgt accgtgtggt cagcgtcctc    900
accgtcctgc accaggactg gctgaacggc aaggagtaca agtgcaaggt ctccaacaaa    960
ggcctcccgt cctccatcga gaaaaccatc tccaaagcca aagggcagcc ccgagagcca   1020

```
caggtgtaca ccctgcccc atcccaggag gagatgacca agaaccaggt cagcctgacc    1080
tgcctggtca aaggcttcta ccccagcgac atcgccgtgg agtgggaaag caatgggcag    1140
ccggagaaca actacaagac cacgcctccc gtgctggact ccgacggctc cttcttcctc    1200
tacagcaggc taaccgtgga caagagcagg tggcaggagg ggaatgtctt ctcatgctcc    1260
gtgatgcatg aggctctgca caaccactac acacagaaga gcctctccct gtctctgggt    1320
```

<210> SEQ ID NO 162
<211> LENGTH: 214
<212> TYPE: PRT
<213> ORGANISM: Artificial
<220> FEATURE:
<223> OTHER INFORMATION: Synthetic

<400> SEQUENCE: 162

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Lys Ser Ile Ser Lys Tyr
             20                  25                  30

Thr Ala Trp Tyr Gln Gln Lys Pro Gly Lys Ala Pro Lys Leu Leu Ile
         35                  40                  45

Tyr Ala Gly Ser Lys Arg Tyr Tyr Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln His Asn Glu Tyr Pro Tyr
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 163
<211> LENGTH: 642
<212> TYPE: DNA
<213> ORGANISM: Artificial
<220> FEATURE:
<223> OTHER INFORMATION: Synthetic

<400> SEQUENCE: 163

```
gacatccaga tgacccagtc tccatcctcc ctgtctgcat ctgtaggaga cagagtcacc      60
atcacttgca gggcgagtaa gagcattagc aaatatacag cctggtatca gcagaaacca     120
gggaaagccc ctaagctcct gatctatgct gggtccaagc ggtactacgg agtcccatca     180
aggttcagtg gcagtggatc tgggacagat ttcactctca ccatcagcag tctgcaacct     240
```

```
gaagattttg caacttacta ttgtcaacaa cataatgaat acccgtacac gttcggcgga    300
gggaccaagg tggagatcaa acggactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gc                      642
```

<210> SEQ ID NO 164  
<211> LENGTH: 440  
<212> TYPE: PRT  
<213> ORGANISM: Artificial  
<220> FEATURE:  
<223> OTHER INFORMATION: Synthetic

<400> SEQUENCE: 164

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Arg Phe Thr Ser Phe
            20                  25                  30

Leu Ile Glu Trp Val Arg Gln Ala Pro Gly Gln Gly Leu Glu Trp Met
        35                  40                  45

Gly Thr Ser Asn Pro Arg Thr Gly Arg Thr Lys Tyr Lys Thr Lys Phe
    50                  55                  60

Arg Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Phe Phe Asp Tyr Trp Gly Gln Gly Thr Thr Val Thr Val
            100                 105                 110

Ser Ser Ala Ser Thr Lys Gly Pro Ser Val Phe Pro Leu Ala Pro Cys
        115                 120                 125

Ser Arg Ser Thr Ser Glu Ser Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Lys Thr Tyr Thr Cys Asn Val Asp His Lys Pro Ser Asn Thr Lys Val
        195                 200                 205

Asp Lys Arg Val Glu Ser Lys Tyr Gly Pro Pro Cys Pro Pro Cys Pro
    210                 215                 220

Ala Pro Glu Ala Ala Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser Gln Glu Asp Pro Glu Val Gln Phe Asn Trp Tyr
            260                 265                 270

Val Asp Gly Val Glu Val His Asn Ala Lys Thr Lys Pro Arg Glu Glu
        275                 280                 285

Gln Phe Asn Ser Thr Tyr Arg Val Val Ser Val Leu Thr Val Leu His
    290                 295                 300
```

```
Gln Asp Trp Leu Asn Gly Lys Glu Tyr Lys Cys Lys Val Ser Asn Lys
305                 310                 315                 320

Gly Leu Pro Ser Ser Ile Glu Lys Thr Ile Ser Lys Ala Lys Gly Gln
                325                 330                 335

Pro Arg Glu Pro Gln Val Tyr Thr Leu Pro Pro Ser Gln Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Arg Leu Thr Val Asp Lys Ser Arg Trp Gln Glu Gly Asn Val
                405                 410                 415

Phe Ser Cys Ser Val Met His Glu Ala Leu His Asn His Tyr Thr Gln
            420                 425                 430

Lys Ser Leu Ser Leu Ser Leu Gly
        435                 440
```

<210> SEQ ID NO 165
<211> LENGTH: 1320
<212> TYPE: DNA
<213> ORGANISM: Artificial
<220> FEATURE:
<223> OTHER INFORMATION: Synthetic

<400> SEQUENCE: 165

| | | |
|---|---|---|
| caggtgcagc tggtgcagtc tggggctgag gtgaagaagc ctgggtcctc agtgaaggtt | 60 |
| tcctgcaagg catctggcta ccgcttcact tcgttcttga tagagtgggt gcgacaggcc | 120 |
| cctggacaag ggcttgagtg gatgggaacg agtaatccta ggactggtag acaaagtat | 180 |
| aaaaccaagt tcaggggcag agtcaccatt accgcggaca aatccacgag cacagcctac | 240 |
| atggagctga gcagcctgag atctgaggac acggccgtgt attactgtgc gcgcgagttt | 300 |
| tttgactact ggggccaagg aaccacggtc accgtctcct cagcctccac caagggccca | 360 |
| tcggtcttcc cgctagcgcc ctgctccagg agcacctccg agagcacagc cgccctgggc | 420 |
| tgcctggtca aggactactt ccccgaaccg gtgacggtgt cgtggaactc aggcgccctg | 480 |
| accagcggcg tgcacacctt cccggctgtc ctacagtcct caggactcta ctccctcagc | 540 |
| agcgtggtga ccgtgccctc agcagcttg gcacgaaga cctacacctg caacgtagat | 600 |
| cacaagccca gcaacaccaa ggtggacaag agagttgagt ccaaatatgg tccccatgc | 660 |
| ccaccctgcc cagcacctga gccgccggg ggaccatcag tcttcctgtt cccccaaaa | 720 |
| cccaaggaca ctctcatgat ctcccggacc cctgaggtca cgtgcgtggt ggtggacgtg | 780 |
| agccaggaag accccgaggt ccagttcaac tggtacgtgg atggcgtgga ggtgcataat | 840 |
| gccaagacaa agccgcggga ggagcagttc aacagcacgt accgtgtggt cagcgtcctc | 900 |
| accgtcctgc accaggactg gctgaacggc aaggagtaca agtgcaaggt ctccaacaaa | 960 |
| ggcctcccgt cctccatcga gaaaaccatc tccaaagcca agggcagcc cgagagcca | 1020 |
| caggtgtaca ccctgccccc atcccaggag gagatgacca gaaccaggt cagcctgacc | 1080 |
| tgcctggtca aaggcttcta ccccagcgac atcgccgtgg agtgggaaag caatgggcag | 1140 |
| ccggagaaca actacaagac cacgcctccc gtgctggact ccgacggctc cttcttcctc | 1200 |
| tacagcaggc taaccgtgga caagagcagg tggcaggagg ggaatgtctt ctcatgctcc | 1260 | gtgatgcatg aggctctgca caaccactac acacagaaga gcctctccct gtctctgggt    1320

<210> SEQ ID NO 166
<211> LENGTH: 214
<212> TYPE: PRT
<213> ORGANISM: Artificial
<220> FEATURE:
<223> OTHER INFORMATION: Synthetic

<400> SEQUENCE: 166

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Ile Ser Lys Tyr
            20                  25                  30

Thr Ala Trp Tyr Gln Gln Lys Pro Gly Lys Ala Pro Lys Leu Leu Ile
        35                  40                  45

Tyr Ala Gly Ser Lys Arg Tyr Tyr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asn Glu Tyr Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 167
<211> LENGTH: 642
<212> TYPE: DNA
<213> ORGANISM: Artificial
<220> FEATURE:
<223> OTHER INFORMATION: Synthetic

<400> SEQUENCE: 167
gacatccaga tgacccagtc tccatcctcc ctgtctgcat ctgtaggaga cagagtcacc      60
atcacttgca gggcgagtaa gagcattagc aaatatacag cctggtatca gcagaaacca     120
gggaaagccc ctaagctcct gatctatgct ggtccaagc ggtactacgg agtcccatca      180
aggttcagtg gcagtggatc tgggacagat ttcactctca ccatcagcag tctgcaacct    240
gaagattttg caacttacta ttgtcaacaa cataatgaat acccgtacac gttcggcgga    300
gggaccaagg tggagatcaa acggactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480

```
gagagtgtca cagagcagga cagcaaggac agcacctaca gcctcagcag caccctgacg      540
ctgagcaaag cagactacga gaaacacaaa gtctacgcct gcgaagtcac ccatcagggc      600
ctgagctcgc ccgtcacaaa gagcttcaac aggggagagt gc                        642
```

```
<210> SEQ ID NO 168
<211> LENGTH: 14
<212> TYPE: PRT
<213> ORGANISM: Homo sapiens

<400> SEQUENCE: 168

Trp Phe Gln Gln Lys Pro Gly Lys Ala Pro Lys Ser Leu Ile
1               5                   10

<210> SEQ ID NO 169
<211> LENGTH: 10
<212> TYPE: PRT
<213> ORGANISM: Homo sapiens

<400> SEQUENCE: 169

Phe Gly Gln Gly Thr Lys Leu Glu Ile Lys
1               5                   10

<210> SEQ ID NO 170
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: Xaa is Leu or Thr

<400> SEQUENCE: 170

Arg Ala Ser Lys Ser Ile Ser Lys Tyr Xaa Ala
1               5                   10

<210> SEQ ID NO 171
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Xaa is Leu or Arg
<220> FEATURE:
<221> NAME/KEY: MISC_FEATURE
<222> LOCATION: (7)..(7)
<223> OTHER INFORMATION: Xaa is Ser, Tyr or Trp

<400> SEQUENCE: 171

Ala Gly Ser Lys Xaa His Xaa
1               5

<210> SEQ ID NO 172
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is Gln or Phe

<400> SEQUENCE: 172
```

```
Xaa Gln His Asn Glu Tyr Pro Tyr Thr
1               5
```

```
<210> SEQ ID NO 173
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa is Ser or Ile
<220> FEATURE:
<221> NAME/KEY: MISC_FEATURE
<222> LOCATION: (8)..(8)
<223> OTHER INFORMATION: Xaa is Arg or Gly
<220> FEATURE:
<221> NAME/KEY: MISC_FEATURE
<222> LOCATION: (12)..(12)
<223> OTHER INFORMATION: Xaa is Lys or Asn
<220> FEATURE:
<221> NAME/KEY: MISC_FEATURE
<222> LOCATION: (13)..(13)
<223> OTHER INFORMATION: Xaa is Ser or Glu

<400> SEQUENCE: 173

Thr Xaa Asn Pro Arg Thr Gly Xaa Thr Lys Tyr Xaa Xaa Lys Phe Arg
1               5                   10                  15

Gly
```

```
<210> SEQ ID NO 174
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Xaa is Leu or Arg
<220> FEATURE:
<221> NAME/KEY: MISC_FEATURE
<222> LOCATION: (6)..(6)
<223> OTHER INFORMATION: Xaa is His, Arg, or Tyr
<220> FEATURE:
<221> NAME/KEY: MISC_FEATURE
<222> LOCATION: (7)..(7)
<223> OTHER INFORMATION: Xaa is Ser, Trp, or Tyr

<400> SEQUENCE: 174

Ala Gly Ser Lys Xaa Xaa Xaa
1               5
```

```
<210> SEQ ID NO 175
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is Ala or Arg

<400> SEQUENCE: 175

Gly Tyr Xaa Phe Thr Ser Phe Leu Ile Glu
1               5                   10
```

```
<210> SEQ ID NO 176
<211> LENGTH: 17
<212> TYPE: PRT
```

<213> ORGANISM: Artificial
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Xaa is Gly or Arg
<220> FEATURE:
<221> NAME/KEY: MISC_FEATURE
<222> LOCATION: (9)..(9)
<223> OTHER INFORMATION: Xaa is Thr or Arg
<220> FEATURE:
<221> NAME/KEY: MISC_FEATURE
<222> LOCATION: (13)..(13)
<223> OTHER INFORMATION: Xaa is Glu, Thr or Ser

<400> SEQUENCE: 176

```
Thr Ser Asn Pro Arg Thr Gly Xaa Xaa Lys Tyr Lys Xaa Lys Phe Arg
1               5                   10                  15

Gly
```

<210> SEQ ID NO 177
<211> LENGTH: 7
<212> TYPE: PRT
<213> ORGANISM: Artificial
<220> FEATURE:
<223> OTHER INFORMATION: Synthetic

<400> SEQUENCE: 177

```
Ala Gly Ser Lys Arg His Tyr
1               5
```

<210> SEQ ID NO 178
<211> LENGTH: 114
<212> TYPE: PRT
<213> ORGANISM: Artificial
<220> FEATURE:
<223> OTHER INFORMATION: Synthetic

<400> SEQUENCE: 178

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Ser Phe
            20                  25                  30

Leu Ile Glu Trp Val Arg Gln Ala Pro Gly Gln Gly Leu Glu Trp Met
        35                  40                  45

Gly Thr Ser Asn Pro Arg Thr Gly Gly Thr Lys Tyr Lys Ser Lys Phe
    50                  55                  60

Arg Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Phe Phe Asp Tyr Trp Gly Gln Gly Thr Thr Val Thr Val
            100                 105                 110

Ser Ser
```

<210> SEQ ID NO 179
<211> LENGTH: 440
<212> TYPE: PRT
<213> ORGANISM: Artificial
<220> FEATURE:
<223> OTHER INFORMATION: Synthetic

<400> SEQUENCE: 179

```
Gln Val Gln Leu Val Gln Ser Gly Ala Glu Val Lys Lys Pro Gly Ser
```

-continued

```
             1               5                  10                 15
        Ser Val Lys Val Ser Cys Lys Ala Ser Gly Tyr Ala Phe Thr Ser Phe
                         20                 25                 30

Leu Ile Glu Trp Val Arg Gln Ala Pro Gly Gln Gly Leu Glu Trp Met
                         35                 40                 45

Gly Thr Ser Asn Pro Arg Thr Gly Thr Lys Tyr Lys Ser Lys Phe
                         50                 55                 60

Arg Gly Arg Val Thr Ile Thr Ala Asp Lys Ser Thr Ser Thr Ala Tyr
         65                  70                 75                  80

Met Glu Leu Ser Ser Leu Arg Ser Glu Asp Thr Ala Val Tyr Tyr Cys
                         85                 90                 95

Ala Arg Glu Phe Phe Asp Tyr Trp Gly Gln Gly Thr Thr Val Thr Val
                        100                105                110

Ser Ser Ala Ser Thr Lys Gly Pro Ser Val Phe Pro Leu Ala Pro Cys
                        115                120                125

Ser Arg Ser Thr Ser Glu Ser Thr Ala Ala Leu Gly Cys Leu Val Lys
                        130                135                140

Asp Tyr Phe Pro Glu Pro Val Thr Val Ser Trp Asn Ser Gly Ala Leu
        145                 150                155                 160

Thr Ser Gly Val His Thr Phe Pro Ala Val Leu Gln Ser Ser Gly Leu
                        165                170                175

Tyr Ser Leu Ser Ser Val Val Thr Val Pro Ser Ser Ser Leu Gly Thr
                        180                185                190

Lys Thr Tyr Thr Cys Asn Val Asp His Lys Pro Ser Asn Thr Lys Val
                        195                200                205

Asp Lys Arg Val Glu Ser Lys Tyr Gly Pro Pro Cys Pro Pro Cys Pro
                        210                215                220

Ala Pro Glu Ala Ala Gly Gly Pro Ser Val Phe Leu Phe Pro Pro Lys
        225                 230                235                 240

Pro Lys Asp Thr Leu Met Ile Ser Arg Thr Pro Glu Val Thr Cys Val
                        245                250                255

Val Val Asp Val Ser Gln Glu Asp Pro Glu Val Gln Phe Asn Trp Tyr
                        260                265                270

Val Asp Gly Val Glu Val His Asn Ala Lys Thr Lys Pro Arg Glu Glu
                        275                280                285

Gln Phe Asn Ser Thr Tyr Arg Val Val Ser Val Leu Thr Val Leu His
                        290                295                300

Gln Asp Trp Leu Asn Gly Lys Glu Tyr Lys Cys Lys Val Ser Asn Lys
        305                 310                315                 320

Gly Leu Pro Ser Ser Ile Glu Lys Thr Ile Ser Lys Ala Lys Gly Gln
                        325                330                335

Pro Arg Glu Pro Gln Val Tyr Thr Leu Pro Pro Ser Gln Glu Glu Met
                        340                345                350

Thr Lys Asn Gln Val Ser Leu Thr Cys Leu Val Lys Gly Phe Tyr Pro
                        355                360                365

Ser Asp Ile Ala Val Glu Trp Glu Ser Asn Gly Gln Pro Glu Asn Asn
        370                 375                380

Tyr Lys Thr Thr Pro Pro Val Leu Asp Ser Asp Gly Ser Phe Phe Leu
        385                 390                395                 400

Tyr Ser Arg Leu Thr Val Asp Lys Ser Arg Trp Gln Glu Gly Asn Val
                        405                410                415

Phe Ser Cys Ser Val Met His Glu Ala Leu His Asn His Tyr Thr Gln
                        420                425                430
```

```
Lys Ser Leu Ser Leu Ser Leu Gly
        435                 440

<210> SEQ ID NO 180
<211> LENGTH: 107
<212> TYPE: PRT
<213> ORGANISM: Artificial
<220> FEATURE:
<223> OTHER INFORMATION: Synthetic

<400> SEQUENCE: 180

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Ile Ser Lys Tyr
            20                  25                  30

Thr Ala Trp Tyr Gln Gln Lys Pro Gly Lys Ala Pro Lys Leu Leu Ile
        35                  40                  45

Tyr Ala Gly Ser Lys Arg His Tyr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asn Glu Tyr Pro Tyr
                85                  90                  95

Thr Phe Gly Gly Gly Thr Lys Val Glu Ile Lys
            100                 105

<210> SEQ ID NO 181
<211> LENGTH: 214
<212> TYPE: PRT
<213> ORGANISM: Artificial
<220> FEATURE:
<223> OTHER INFORMATION: Synthetic

<400> SEQUENCE: 181

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Ile Ser Lys Tyr
            20                  25                  30

Thr Ala Trp Tyr Gln Gln Lys Pro Gly Lys Ala Pro Lys Leu Leu Ile
        35                  40                  45

Tyr Ala Gly Ser Lys Arg His Tyr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asn Glu Tyr Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

Ala Cys Glu Val Thr His Gln Gly Leu Ser Ser Pro Val Thr Lys Ser
            195                 200                 205

Phe Asn Arg Gly Glu Cys
        210

<210> SEQ ID NO 182
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is Ala or Arg

<400> SEQUENCE: 182

Gly Tyr Xaa Phe Thr Ser Phe Leu Ile Glu
1               5                   10

<210> SEQ ID NO 183
<211> LENGTH: 11
<212> TYPE: PRT
<213> ORGANISM: Homo sapiens

<400> SEQUENCE: 183

Ala Asn Ile Val Pro Glu Thr Ser Pro Glu Ser
1               5                   10

<210> SEQ ID NO 184
<211> LENGTH: 10
<212> TYPE: PRT
<213> ORGANISM: Homo sapiens

<400> SEQUENCE: 184

Ile Val Pro Glu Thr Ser Pro Glu Ser Val
1               5                   10

<210> SEQ ID NO 185
<211> LENGTH: 10
<212> TYPE: PRT
<213> ORGANISM: Homo sapiens

<400> SEQUENCE: 185

Asn Ile Val Pro Glu Thr Ser Pro Glu Ser
1               5                   10

<210> SEQ ID NO 186
<211> LENGTH: 8
<212> TYPE: PRT
<213> ORGANISM: Homo sapiens

<400> SEQUENCE: 186

Val Pro Glu Thr Ser Pro Ser Val
1               5

<210> SEQ ID NO 187
<211> LENGTH: 10
<212> TYPE: PRT
<213> ORGANISM: Homo sapiens

<400> SEQUENCE: 187

Pro Glu Thr Ser Pro Glu Ser Val Pro Ile
1               5                   10

<210> SEQ ID NO 188

```
<211> LENGTH: 10
<212> TYPE: PRT
<213> ORGANISM: Homo sapiens

<400> SEQUENCE: 188

Thr Ser Pro Glu Ser Val Pro Ile Ile Ser
1               5                   10

<210> SEQ ID NO 189
<211> LENGTH: 9
<212> TYPE: PRT
<213> ORGANISM: Homo sapiens

<400> SEQUENCE: 189

Ala Asn Ile Val Pro Glu Thr Ser Pro
1               5

<210> SEQ ID NO 190
<211> LENGTH: 9
<212> TYPE: PRT
<213> ORGANISM: Homo sapiens

<400> SEQUENCE: 190

Ile Val Pro Glu Thr Ser Pro Glu Ser
1               5

<210> SEQ ID NO 191
<211> LENGTH: 8
<212> TYPE: PRT
<213> ORGANISM: Homo sapiens

<400> SEQUENCE: 191

Ala Asn Ile Val Pro Glu Thr Ser
1               5

<210> SEQ ID NO 192
<211> LENGTH: 8
<212> TYPE: PRT
<213> ORGANISM: Homo sapiens

<400> SEQUENCE: 192

Ile Val Pro Glu Thr Ser Pro Glu
1               5

<210> SEQ ID NO 193
<211> LENGTH: 7
<212> TYPE: PRT
<213> ORGANISM: Homo sapiens

<400> SEQUENCE: 193

Ile Val Pro Glu Thr Ser Pro
1               5

<210> SEQ ID NO 194
<211> LENGTH: 5
<212> TYPE: PRT
<213> ORGANISM: Homo sapiens

<400> SEQUENCE: 194

Ile Gln Gly Glu Ser
1               5

<210> SEQ ID NO 195
<211> LENGTH: 10
<212> TYPE: PRT
<213> ORGANISM: Homo sapiens
```

```
<400> SEQUENCE: 195

Ile Thr Pro Thr Lys Ile Pro Glu Ile Thr
1               5                   10

<210> SEQ ID NO 196
<211> LENGTH: 10
<212> TYPE: PRT
<213> ORGANISM: Homo sapiens

<400> SEQUENCE: 196

Ile Gln Gly Glu Ser Ile Thr Pro Thr Lys
1               5                   10

<210> SEQ ID NO 197
<211> LENGTH: 10
<212> TYPE: PRT
<213> ORGANISM: Homo sapiens

<400> SEQUENCE: 197

Gln Gly Glu Ser Ile Thr Pro Thr Lys Ile
1               5                   10

<210> SEQ ID NO 198
<211> LENGTH: 10
<212> TYPE: PRT
<213> ORGANISM: Homo sapiens

<400> SEQUENCE: 198

Gly Glu Ser Ile Thr Pro Thr Lys Ile Pro
1               5                   10

<210> SEQ ID NO 199
<211> LENGTH: 10
<212> TYPE: PRT
<213> ORGANISM: Homo sapiens

<400> SEQUENCE: 199

Glu Ser Ile Thr Pro Thr Lys Ile Pro Glu
1               5                   10

<210> SEQ ID NO 200
<211> LENGTH: 10
<212> TYPE: PRT
<213> ORGANISM: Homo sapiens

<400> SEQUENCE: 200

Ser Ile Thr Pro Thr Lys Ile Pro Glu Ile
1               5                   10

<210> SEQ ID NO 201
<211> LENGTH: 10
<212> TYPE: PRT
<213> ORGANISM: Homo sapiens

<400> SEQUENCE: 201

Ile Thr Pro Thr Lys Ile Pro Glu Ile Thr
1               5                   10

<210> SEQ ID NO 202
<211> LENGTH: 13
<212> TYPE: PRT
<213> ORGANISM: Homo sapiens
```

<400> SEQUENCE: 202

Ile Thr Thr Glu Ile Tyr Met Ser Asn Gly Ser Asn Ser
1               5                   10

<210> SEQ ID NO 203
<211> LENGTH: 12
<212> TYPE: PRT
<213> ORGANISM: Homo sapiens

<400> SEQUENCE: 203

Thr Glu Ile Tyr Met Ser Asn Gly Ser Asn Ser Ala
1               5                   10

<210> SEQ ID NO 204
<211> LENGTH: 10
<212> TYPE: PRT
<213> ORGANISM: Homo sapiens

<400> SEQUENCE: 204

Ile Thr Thr Glu Ile Tyr Met Ser Asn Gly
1               5                   10

<210> SEQ ID NO 205
<211> LENGTH: 10
<212> TYPE: PRT
<213> ORGANISM: Homo sapiens

<400> SEQUENCE: 205

Thr Thr Glu Ile Tyr Met Ser Asn Gly Ser
1               5                   10

<210> SEQ ID NO 206
<211> LENGTH: 10
<212> TYPE: PRT
<213> ORGANISM: Homo sapiens

<400> SEQUENCE: 206

Thr Glu Ile Tyr Met Ser Asn Gly Ser Asn
1               5                   10

<210> SEQ ID NO 207
<211> LENGTH: 10
<212> TYPE: PRT
<213> ORGANISM: Homo sapiens

<400> SEQUENCE: 207

Glu Ile Tyr Met Ser Asn Gly Ser Asn Ser
1               5                   10

<210> SEQ ID NO 208
<211> LENGTH: 10
<212> TYPE: PRT
<213> ORGANISM: Homo sapiens

<400> SEQUENCE: 208

Ile Tyr Met Ser Asn Gly Ser Asn Ser Ala
1               5                   10

<210> SEQ ID NO 209
<211> LENGTH: 10
<212> TYPE: PRT
<213> ORGANISM: Homo sapiens -continued

```
<400> SEQUENCE: 209

Arg Asp Gly Trp Val Ser Tyr Tyr Asn Gln
1               5                   10

<210> SEQ ID NO 210
<211> LENGTH: 7
<212> TYPE: PRT
<213> ORGANISM: Homo sapiens

<400> SEQUENCE: 210

Glu Ile Tyr Met Ser Asn Gly
1               5

<210> SEQ ID NO 211
<211> LENGTH: 8
<212> TYPE: PRT
<213> ORGANISM: Homo sapiens

<400> SEQUENCE: 211

Ile Tyr Met Ser Asn Gly Ser Asn
1               5

<210> SEQ ID NO 212
<211> LENGTH: 5
<212> TYPE: PRT
<213> ORGANISM: Homo sapiens

<400> SEQUENCE: 212

Ile Thr Pro Thr Lys
1               5

<210> SEQ ID NO 213
<211> LENGTH: 10
<212> TYPE: PRT
<213> ORGANISM: Homo sapiens

<400> SEQUENCE: 213

Ser Ile Thr Pro Thr Lys Ile Pro Glu Ile
1               5                   10

<210> SEQ ID NO 214
<211> LENGTH: 10
<212> TYPE: PRT
<213> ORGANISM: Homo sapiens

<400> SEQUENCE: 214

Glu Ile Tyr Met Ser Asn Gly Ser Asn Ser
1               5                   10
```

ANTI-FERROPORTIN 1 MONOCLONAL ANTIBODIES AND USES THEREOF

This application claims priority to U.S. provisional patent application Ser. No. 61/120,076, filed Dec. 5, 2008, and U.S. provisional patent application Ser. No. 61/239,818, filed Sep. 4, 2009.

The present invention relates to antibodies that bind ferroportin 1 (FPN1) and their use in treating anemia.

Iron is an essential trace element that is required for numerous cellular functions. In mammals, the supply of iron to the body is regulated to match the body's iron requirements at the level of iron absorption by duodenal enterocytes. Iron transport across the basolateral membrane of the enterocyte is thought to be mediated by ferroportin 1 (also known as iron-regulated transporter 1 (IREG-1), metal transporter protein 1 (MTP1) and SLC40A1), hereafter referred to as FPN1.

FPN1 is now known to be a receptor for hepcidin, a polypeptide hormone made by the liver in response to iron stores and inflammation. Binding of mature hepcidin to FPN1 leads to the internalization and degradation of FPN1, preventing cellular iron export, and it is a major controlling factor of systemic iron homeostasis.

U.S. Pat. No. 7,166,448 discloses, inter alia, nucleotide sequences encoding human FPN1 proteins, human FPN1 proteins having iron transport function, and a rabbit polyclonal antiserum generated to a peptide consisting of the C-terminal 19 amino acids of the human FPN1. PCT International Patent Application Publication No. WO2009/094551 describes ferroportin Mabs and methods of using them for treating disorders of iron homeostasis. More specifically, WO2009/094551 describes rodent and fully human monoclonal antibodies to various epitopes of human FPN1 proteins.

In view of the involvement of FPN1 in iron transport and the association of FPN1 mutations with diseases of iron homeostasis, there exists a need for therapeutically useful FPN1 antagonists that bind with high affinity to an extracellular epitope of FPN1 and, upon binding, inhibit mature hepcidin-mediated FPN1 internalization, thereby maintaining or enhancing export of iron from intracellular stores. Additionally, targeting FPN1 therapeutically with a Mab, or antigen-binding fragment thereof, with the goal of inhibiting the binding of mature hepcidin to an extracellular epitope of FPN1 must be accomplished precisely enough so that the antibody doesn't significantly perturb the efflux of cellular iron and/or induce internalization upon binding to its target. Additionally, an anti-FPN antibody intended for use in human medical therapy must exhibit sufficient pharmacokinetic and pharmacodynamic characteristics, including in vivo stability and/or elimination half life to allow for their therapeutic use. One or more of the anti-human FPN1 antibodies disclosed herein specifically bind human FPN1, including at least one peptide fragment thereof selected from the group consisting of:

a) $_{403}$SPFEDIRSRFIQGESITPTK$_{422}$;    (SEQ ID NO: 12)

b) $_{406}$EDIRSRFIQGESIT$_{419}$;    (SEQ ID NO: 13)

c) $_{409}$RSRFIQGESITPTK$_{422}$;    (SEQ ID NO: 14)

d) $_{403}$SPFEDIRSRFIQG$_{415}$;    (SEQ ID NO: 15)

e) $_{409}$RSRFIQGESIT$_{419}$;    (SEQ ID NO: 16)
and f) $_{409}$RSRFIQG$_{415}$,    (SEQ ID NO: 95)

block the binding of hepcidin to ferroportin, potently inhibit hepcidin activity in vitro, elevate serum iron levels in a dose-dependent manner in vivo, and have acceptable solubility, in vivo stability, and elimination half life characteristics, making them useful agents for treating and/or preventing anemia in a subject in need of such treatment by administration via intravenous infusion or, even perhaps, via subcutaneous injection.

Thus, among its various aspects, the present invention provides:

Monoclonal antibodies, or antigen-binding fragments thereof, which specifically bind to human ferroportin 1 consisting of the amino acid sequence shown in SEQ ID NO: 1 at an epitope comprising amino acids localized to one or more amino acid sequences selected from the group consisting of:

a. $_{403}$SPFEDIRSRFIQGESITPTK$_{422}$;    (SEQ ID NO: 12)

b. $_{406}$EDIRSRFIQGESIT$_{419}$;    (SEQ ID NO: 13)

c. $_{409}$RSRFIQGESITPTK$_{422}$;    (SEQ ID NO: 14)

d. $_{403}$SPFEDIRSRFIQG$_{415}$;    (SEQ ID NO: 15)

e. $_{409}$RSRFIQGESIT$_{419}$;    (SEQ ID NO: 16)
and f. $_{409}$RSRFIQG$_{415}$.    (SEQ ID NO: 95)

In some embodiments, the present invention provides Mabs, or antigen-binding fragments thereof, comprising a LCDR1, LCDR2, LCDR3, HCDR1, HCDR2, and HCDR3 comprising the amino acid sequence shown in SEQ ID NOs: 37, 129, 22, 107, 118, and 120, respectively, and the Mab, or antigen-binding fragment, binds human FPN 1 consisting of the amino acid sequence shown in SEQ ID NO: 1 at an epitope comprising an amino acid or amino acids localized to an amino acid sequence as shown in SEQ ID NO: 12 with a $K_D$ of about 100 nM or less as determined by surface plasmon resonance (SPR), preferably, at 25° C. for Mabs and 37° C. for Fabs.

In some embodiments, the Mab, or antigen-binding fragment thereof, comprises six CDRs selected from the group consisting of:

(i) LCDR1, LCDR2, LCDR3, HCDR1, HCDR2, and HCDR3 comprising the amino acid sequences shown in SEQ ID NOs: 20, 32, 33, 30, 31, and 19, respectively;

(ii) LCDR1, LCDR2, LCDR3, HCDR1, HCDR2, and HCDR3 comprising the amino acid sequences shown in SEQ ID NOs: 42, 32, 33, 30, 43, and 19, respectively;

(iii) LCDR1, LCDR2, LCDR3, HCDR1, HCDR2, and HCDR3 comprising the amino acid sequences shown in SEQ ID NOs: 42, 27, 22, 23, 41, and 19, respectively;

(iv) LCDR1, LCDR2, LCDR3, HCDR1, HCDR2, and HCDR3 comprising the amino acid sequences shown in SEQ ID NOs: 42, 32, 33, 23, 41, and 19, respectively;

(v) LCDR1, LCDR2, LCDR3, HCDR1, HCDR2, and HCDR3 comprising the amino acid sequences shown in SEQ ID NOs: 20, 21, 22, 17, 18, and 19, respectively;

(vi) LCDR1, LCDR2, LCDR3, HCDR1, HCDR2, and HCDR3 comprising the amino acid sequences shown in SEQ ID NOs: 20, 27, 29, 23, 24, and 19, respectively;

(vii) LCDR1, LCDR2, LCDR3, HCDR1, HCDR2, and HCDR3 comprising the amino acid sequences shown in SEQ ID NOs: 37, 27, 22, 23, 41, and 19, respectively;

(viii) LCDR1, LCDR2, LCDR3, HCDR1, HCDR2, and HCDR3 comprising the amino acid sequences shown in SEQ ID NOs: 170, 171, 172, 182, 173, and 19, respectively;

(ix) LCDR1, LCDR2, LCDR3, HCDR1, HCDR2, and HCDR3 comprising the amino acid sequences shown in SEQ ID NOs: 37, 127, 22, 23, 116, and 19, respectively;
(x) LCDR1, LCDR2, LCDR3, HCDR1, HCDR2, and HCDR3 comprising the amino acid sequences shown in SEQ ID NOs: 37, 125, 22, 23, 110, and 19, respectively;
(xi) LCDR1, LCDR2, LCDR3, HCDR1, HCDR2, and HCDR3 comprising the amino acid sequences shown in SEQ ID NOs: 37, 122, 22, 23, 110, and 19, respectively;
(xii) LCDR1, LCDR2, LCDR3, HCDR1, HCDR2, and HCDR3 comprising the amino acid sequences shown in SEQ ID NOs: 37, 129, 22, 107, 118, and 120, respectively;
(xiii) LCDR1, LCDR2, LCDR3, HCDR1, HCDR2, and HCDR3 comprising the amino acid sequences shown in SEQ ID NOs: 37, 128, 22, 105, 41, and 119, respectively;
(xiv) LCDR1, LCDR2, LCDR3, HCDR1, HCDR2, and HCDR3 comprising the amino acid sequences shown in SEQ ID NOs: 37, 174, 22, 175, 176, and 120, respectively;
(xvi) LCDR1, LCDR2, LCDR3, HCDR1, HCDR2, and HCDR3 comprising the amino acid sequences shown in SEQ ID NOs: 37, 128, 22, 105, 117, and 19, respectively; and
(xvii) LCDR1, LCDR2, LCDR3, HCDR1, HCDR2, and HCDR3 comprising the amino acid sequences shown in SEQ ID NOs: 37, 177, 22, 23, 112, and 19, respectively, and binds human FPN1 consisting of the amino acid sequence shown in SEQ ID NO: 1 at an epitope consisting of or consisting essentially of an amino acid or amino acids localized to an amino acid sequence selected from the group consisting of:

| | | |
|---|---|---|
| a) | $_{403}$SPFEDIRSRFIQGESITPTK$_{422}$ | (SEQ ID NO: 12) |
| b) | $_{406}$EDIRSRFIQGESIT$_{419}$; | (SEQ ID NO: 13) |
| c) | $_{409}$RSRFIQGESITPTK$_{422}$; | (SEQ ID NO: 14) |
| d) | $_{403}$SPFEDIRSRFIQG$_{415}$; | (SEQ ID NO: 15) |
| e) and | $_{409}$RSRFIQGESIT$_{419}$; | (SEQ ID NO: 16) |
| f) | $_{409}$RSRFIQG$_{415}$ | (SEQ ID NO: 95) | with a $K_D$ of less than about 100 nM as determined by SPR, preferably, at 25° C. for Mabs and 37° C. for Fabs.

In particular embodiments, the Mabs, or antigen-binding fragment thereof, of the present invention, inhibit hepcidin-induced internalization and/or degradation of human FPN1, thereby maintaining or increasing 1) the transport of iron out of cells, 2) the level of serum iron, 3) reticulocyte count, 4) red blood cell count, 5) hemoglobin, and/or 6) hematocrit in a subject, preferably, a human subject, by at least about 10% compared to that of said subject in the absence of said Mab, or antigen-binding fragment thereof.

In another aspect, polynucleotides comprising a nucleotide sequence encoding anti-human FPN1 Mabs, or antigen-binding fragments thereof, of the present invention are provided.

In another aspect, pharmaceutical compositions are provided comprising any of the Mabs, or antigen-binding fragments thereof, described herein and a pharmaceutically acceptable carrier, diluent, or excipient. Also provided is 1) the use of the Mabs, or antigen-binding fragments thereof, disclosed herein in therapy, preferably, a therapy for treating or preventing anemia, 2) the use of the Mabs, or antigen-binding fragments thereof, disclosed herein in combination therapy, preferably, a combination therapy for treating or preventing anemia, 3) the use of the Mabs, or antigen-binding fragments thereof, disclosed herein for treating or preventing anemia, maintaining or increasing serum iron levels, reticulocyte count, red blood cell count, hemoglobin, and/or hematocrit in a subject, preferably, a human, 4) the use of the Mabs, or antigen-binding fragments thereof, disclosed herein for the manufacture of a medicament for treating or preventing anemia, maintaining or increasing serum iron levels, reticulocyte count, red blood cell count, hemoglobin, and/or hematocrit in a subject, preferably, a human, and 5) the use of the Mabs, or antigen-binding fragments thereof, disclosed herein in the manufacture of a medicament for use in combination therapy for treating or preventing anemia, increasing serum iron levels, reticulocyte count, red blood cell count, hemoglobin, and/or hematocrit in a human, wherein said medicament is to be administered in combination with one or more ESA or other therapeutic agent or therapeutic treatment conventionally employed to treat anemia, maintain or increase serum iron levels, reticulocyte count, red blood cell count, hemoglobin, and/or hematocrit in a human.

In yet another aspect, methods are provided for 1) maintaining or increasing serum iron levels, reticulocyte count, red blood cell count, hemoglobin, and/or hematocrit in a subject, preferably, a human, comprising administering to a subject in need thereof an effective amount of a Mab, or antigen-binding fragment thereof, disclosed herein, 2) treating or preventing anemia, including, but not limited to anemia of chronic disease, anemia of cancer, and anemia of inflammation, comprising administering to a subject, preferably, a human, in need thereof an effective amount of a Mab, or antigen-binding fragment thereof, disclosed herein, 3) a method of treating or preventing anemia, including, but not limited to anemia of chronic disease, anemia of cancer, and anemia of inflammation, comprising administering to a subject, preferably, a human patient in need thereof an effective amount of a combination of Mabs, or antigen-binding fragments thereof, disclosed herein, or a mixture of at least one Mab and at least one antigen-binding fragment disclosed herein, and 4) any one of the foregoing methods 1-3, further comprising administering to said human patient an ESA, or other therapeutic agent or therapeutic treatment administered to maintain or increase serum iron levels, reticulocyte count, red blood cell count, hemoglobin, and/or hematocrit in a human.

In yet another aspect, methods are provided for inhibiting mature hepcidin-induced internalization and degradation of FPN1, comprising contacting said FPN1 and an effective amount of at least one Mab, or antigen-binding fragment thereof, disclosed herein.

Also provided is a method of decreasing the binding of mature human hepcidin to human FPN1 comprising contacting said human FPN1 and an effective amount of at least one Mab, and/or antigen-binding fragment thereof, disclosed herein.

Also provided is a method of decreasing the amount of FPN1 proteins that are internalized by a cell expressing FPN1 proteins, comprising administering to a human patient in need thereof an effective amount of at least one of the Mabs, and/or antigen-binding fragments thereof, disclosed herein.

FIG. 1 depicts sequences of various peptides (SEQ ID NOs: 96-102) comprising fragments of the immunogen used to generate anti-FPN1 antibodies and the results of peptide-antibody binding experiments using the peptides to define the epitope of anti-FPN1 Mab 34A9. Underlined amino acids denote actual ferroportin sequences. Mab 34A9 binds to peptides FpnE3a (SEQ ID NO: 96), 060719Z (SEQ ID NO: 97), 0708L4C (SEQ ID NO: 101), and 0708L4D (SEQ ID NO: 102), which all contain the common amino acid sequence of RSRFIQG (SEQ ID NO:95)

FIG. 2A shows the amino acid sequences of fully human light chain framework O2 with interspersed CDRs. The four framework regions are labeled as FRL1, 2, 3, and 4 (SEQ ID NOs: 74, 75, 76, and 77, respectively).

FIG. 2B shows the amino acid sequence of the human heavy chain framework VH1-69 with interspersed CDRs. The four framework regions are labeled FRH1-4 (SEQ ID NOs: 78-81, respectively).

FIG. 3A shows the amino acid sequences of the human light chain framework O18 with interspersed CDRs The four framework regions are labeled as FRL1, 2, 3, and 4 (SEQ ID NOs: 74, 75, 82, and 77, respectively). Residues different from O2 residues are in bold and underlined FIG. 3B shows the amino acid sequence of the human heavy chain framework VH1-18 with interspersed CDRs. The four framework regions are labeled FRH1, 2, 3, and 4 (SEQ ID NOs: 83, 79, 84, and 81, respectively). Residues different from VH1-69 residues are in bold and underlined FIG. 4A shows the amino acid sequences of the human light chain framework L12 with interspersed CDRs The four framework regions are labeled as FRL1, 2, 3, and 4 (SEQ ID NOs: 85, 75, 86, and 77, respectively). Residues different from O2 residues are in bold and underlined FIG. 4B shows the amino acid sequence of the human heavy chain framework VH1-46 with interspersed CDRs. The four framework regions are labeled FRH1, 2, 3, and 4 (SEQ ID NOs: 83, 79, 87, and 81, respectively). Residues different from VH1-69 residues are in bold and underlined.

FIG. 5 shows the amino acid sequences of the human light chain framework L1 with interspersed CDRs The four framework regions are labeled as FRL1, 2, 3, and 4 (SEQ ID NOs: 74, 168, 76, and 169, respectively). Residues different from O2 residues are in bold and underlined. The germline sequence for FR1 region of human light chain framework L12 is as shown in SEQ ID NO:85; a variation wherein the amino acid sequence of the FR1 region of the human light chain framework L1 is as shown in SEQ ID NO:74 is contemplated in certain embodiments of the present invention.

Figure 6:
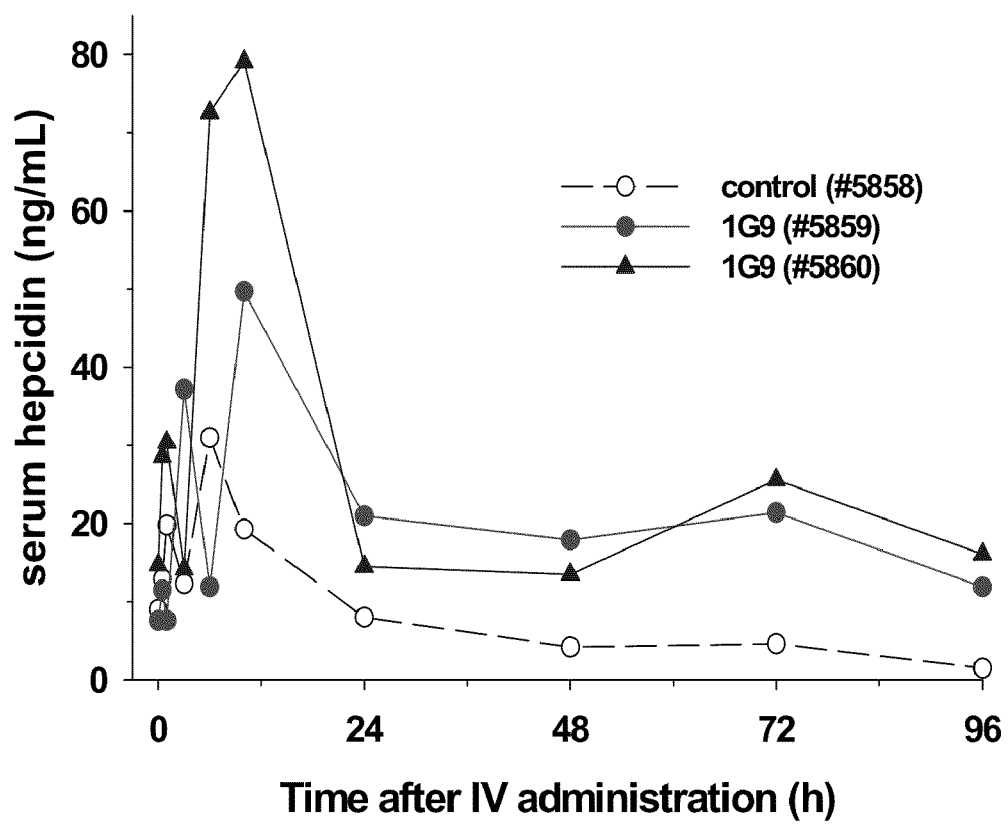

FIG. 6 shows a graph of serum hepcidin levels in male Cynomolgus monkeys after administration of control murine IgG1 or murine Mab 1G9 as a single I.V. dose of 30 mg/kg. Data are from individual animals.

Figure 7:
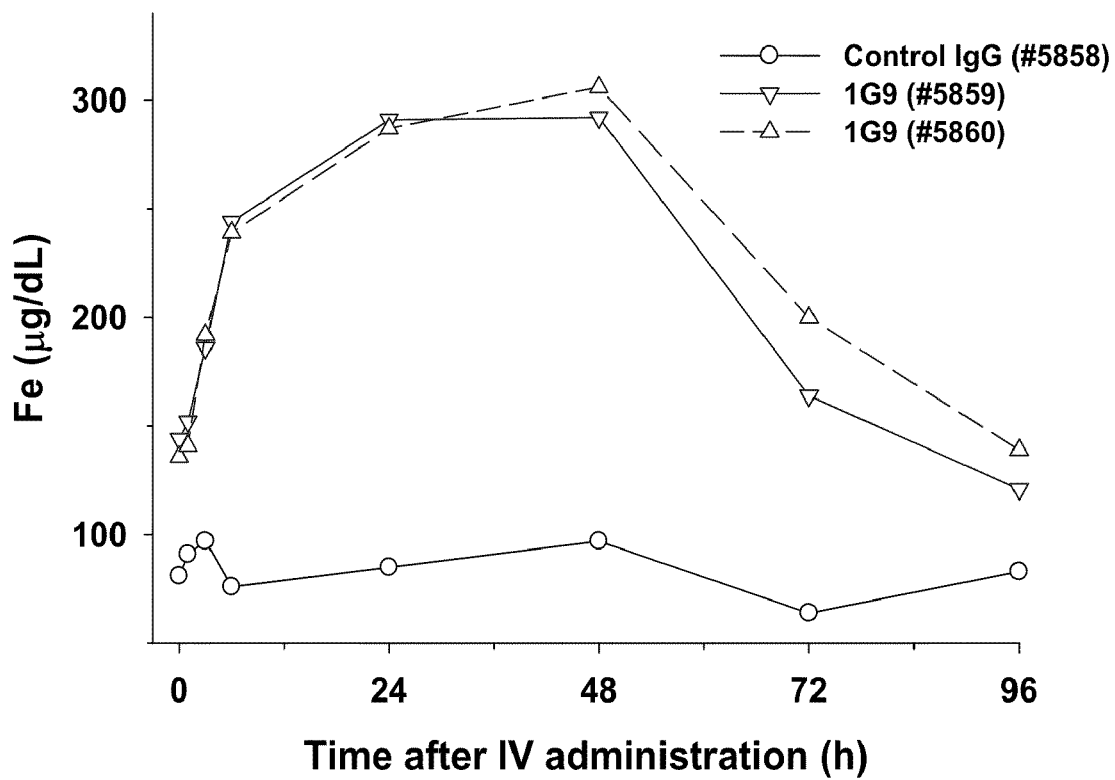

FIG. 7 shows a graph of serum iron levels in male Cynomolgus monkeys after administration of control murine IgG1 or murine Mab 1G9 administered as a single I.V. dose of 30 mg/kg. Data are from individual animals.

FIG. 8 shows the amino acid sequences and consensus amino acid sequence of preferred heavy chain variable regions for the antibodies, and antigen-binding fragments thereof, of the present invention. A period (.) indicates the amino acid in that position is identical to the corresponding amino acid of sequence number 1. CDRs are underlined and in bold for sequence number 1.

FIG. 9 shows the amino acid sequences and consensus amino acid sequence of preferred light chain variable regions for the antibodies, and antigen-binding fragments thereof, of the present invention. A period (.) indicates the amino acid in that position is identical to the corresponding amino acid of sequence number 1. CDRs are underlined and in bold for sequence number 1.

Figure 10:
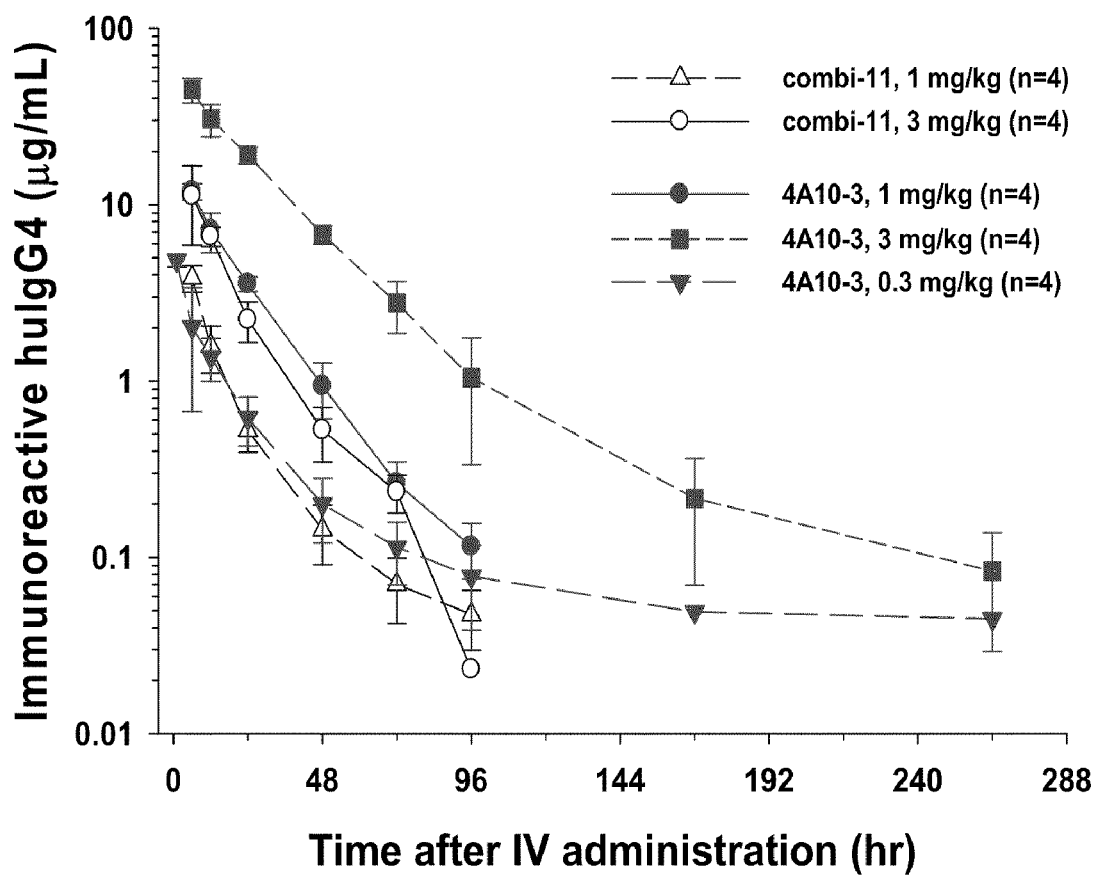

FIG. 10 depicts serum concentrations of Mab 4A10-3 and Mab Combi11 in Cynomolgus monkeys following a single i.v. bolus dose of 0.3, 1.0, or 3.0 mg/kg. Serum concentrations of Mab Combi11 at the 0.3 mg/kg dose were below detection limit of the assay (<20 ng/mL). Data are the mean±SD.

Figure 11:
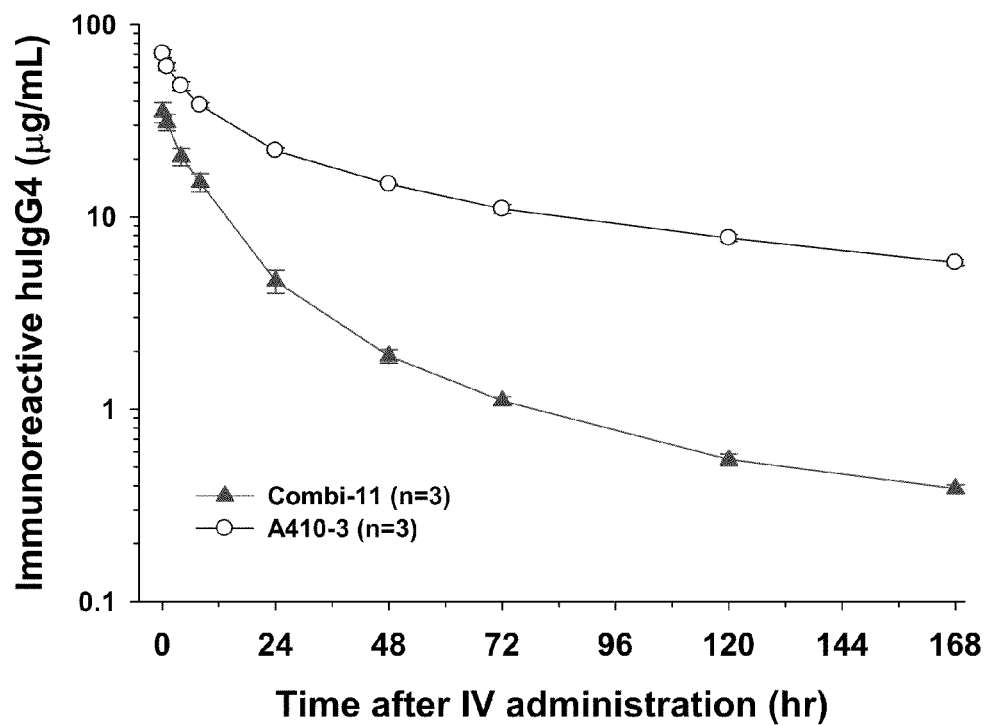

FIG. 11 depicts serum concentrations of Mab 4A10-3 and Mab Combi11 in Sprague Dawley rats following a single i.v. bolus dose of 3.0 mg/kg. Data are the mean±SD.

The following abbreviations are used herein: BCA: bicinchoninic acid, BSA: bovine serum albumin, CDR: complementarity determining region, DTT: dithiothreitol, DMEM: Dulbecco's Modified Eagle's medium, D-PBS: Dulbecco's phosphate-buffered saline, EDTA: ethylenediamine tetraacetic acid, ELISA: enzyme linked immunosorbent assay, ESA: erythropoiesis-stimulating agent, FAC: ferric ammonium citrate, FBS: fetal bovine serum, Fe:NTA: ferric nitrilotriacetate, FLU: fluorescence units, GFP: green fluorescent protein, I.V.: intravenous, IPTG: Isopropyl β-D-1-thiogalactopyranoside, IMAC: Immobilized Metal Ion Affinity Chromatography, Mab: monoclonal antibody, Mabs: monoclonal antibodies, OPD: o-phenylenediamine dihydrochloride, PBS: phosphate-buffered saline, PBST: phosphate-buffered saline Tween-20, SDS: sodium dodecyl sulfate, TBS: Tris-buffered saline, Tris: tris(hydroxymethyl) aminomethane, Triton-X: 4-(1,1,3,3-tetramethylbutyl)phenyl-polyethylene glycol t-octylphenoxypolyethoxyethanol polyethylene glycol tert-octylphenyl ether, Tween-20: polysorbate 20.

The Mabs, or antigen-binding fragments thereof, of the present invention bind an epitope comprising or consisting essentially of or consisting of an amino acid or amino acids localized to amino acids 403-422 (SEQ ID NO: 12) of the human FPN1 polypeptide having the amino acid sequence as shown in SEQ ID NO: 1. In preferred embodiments, these antibodies, or antigen-binding fragments thereof, inhibit the mature human hepcidin induced-internalization and/or degradation of human FPN1, thereby increasing transport of iron out of cells in vitro and in vivo and elevating serum iron levels in vivo. For example, in preferred embodiments, the antibodies of the present invention significantly decrease mature hepcidin-induced accumulation of ferritin within Caco-2 cells, a human enterocyte cell line that endogenously expresses FPN1, in vitro (see, Example 5).

A full-length antibody as it exists naturally is an immunoglobulin molecule comprising 2 heavy chains and 2 light chains interconnected by disulfide bonds. The amino terminal portion of each chain includes a variable region of about 100-110 or more amino acids primarily responsible for antigen recognition via the CDRs contained therein. The carboxy-terminal portion of each chain defines a constant region primarily responsible for effector function.

The term "CDR" as used herein is intended to mean the non-contiguous antigen combining sites found within the variable region of both heavy and light chain polypeptides. These particular regions have been described by Kabat, et al., J. Biol. Chem. 252, 6609-6616 (1977), Kabat, et al., Sequences of protein of immunological interest, (1991), and by Chothia, et al., J. Mol. Biol. 196:901-917 (1987) and by MacCallum, et al., J. Mol. Biol., 262:732-745 (1996) where the definitions include overlapping or subsets of amino acid residues when compared against each other.

The CDRs are interspersed with regions that are more conserved, termed framework regions ("FR"). Each light chain variable region (LCVR) and heavy chain variable region (HCVR) is composed of three CDRs and four FRs, arranged from amino-terminus to carboxy-terminus in the following order: FR1, CDR1, FR2, CDR2, FR3, CDR3, FR4. The three CDRs of the light chain are referred to as "LCDR1, LCDR2, and LCDR3" and the three CDRs of the heavy chain are referred to as "HCDR1, HCDR2, and HCDR3." The CDRs contain most of the residues which form specific interactions with the antigen. The numbering and positioning of CDR amino acid residues within the LCVR and HCVR regions is in accordance with well-known conventions (e.g., Kabat, (1991) and/or Chothia (1987)).

The phrase "Kabat numbering" as used herein is recognized in the art and refers to a system of numbering amino acid residues which are more variable (i.e., hypervariable) than other amino acid residues in the heavy and light chain regions of an antibody (Kabat, et al., Ann. NY Acad. Sci., 190:382-93 (1971); Kabat, et al., Sequences of Proteins of Immunological Interest, Fifth Edition, U.S. Department of Health and Human Services, NIH Publication No. 91-3242 (1991)).

As used herein, the term "monoclonal antibody" (Mab) refers to an antibody that is derived from a single copy or clone including, for example, any eukaryotic, prokaryotic, or phage clone, and not the method by which it is produced. Mabs of the present invention preferably exist in a homogeneous or substantially homogeneous population. Complete Mabs contain 2 heavy chains and 2 light chains. Monoclonal antibodies, or antigen-binding fragments thereof, of the present invention can be produced, for example, by recombinant technologies, phage display technologies, synthetic technologies, e.g., CDR-grafting, or combinations of such technologies, or other technologies known in the art.

As used herein, the phrase "antigen-binding fragments" of Mabs include, for example, Fab fragments, Fab' fragments, F(ab')$_2$ fragments, and single chain Fv fragments.

The term "antibody", or grammatical versions thereof, unless indicated otherwise, refers to Mabs, antigen-binding fragments thereof, as well as combinations thereof, including, for example, combinations of Fabs, and combinations of Mabs and Fabs. Additional antibodies exhibiting similar functional properties as the antibodies according to the present invention can be generated by conventional methods. For example, mice can be immunized with, for example, FPN1 expressing cells, FPN1 or fragments thereof, the resulting antibodies can be recovered and purified, and determination of whether they possess binding, pharmacokinetic, and functional properties similar to or the same as the antibodies disclosed herein can be assessed by the methods disclosed in Examples 3-14 herein below. Antigen-binding fragments can also be prepared by conventional methods well-known in the art. Methods for producing and purifying antibodies and antigen-binding fragments are also well known in the art.

As used herein, the phrase "specifically binds" refers to the ability of an antibody of the present invention to bind to a specified polypeptide or peptide, preferably, human ferroportin 1 consisting of the amino acid sequence shown in SEQ ID NO: 1, or a specified peptide fragment thereof, with a $K_D$ less than about 1000 nM, less than about 100 nM, less than about 10 nM, less than about 1 nM, less than about 100 µM, or less than about 10 µM, as determined by affinity ELISA or SPR assays as described herein, for example, or similar assays known in the art.

Additionally, or alternatively, the phrase "specifically binds" in reference to an antibody of the present invention indicates that the ability of the antibody to bind to or detect human ferroportin 1 consisting of the amino acid sequence shown in SEQ ID NO: 1, or a peptide fragment thereof, is at least about 5 times greater, at least about 10 times greater, at least about 20 times greater, at least about 50 times greater, at least about 100 times greater, at least about 200 times greater, at least about 500 times greater, or at least about 1000 times greater than its ability to bind to or detect another polypeptide (e.g., heparin) or, optionally, another specified peptide fragment of human ferroportin 1.

The present invention also provides an isolated polynucleotide comprising a nucleotide sequence that encodes a Mab, or antigen-binding fragment thereof. In particular embodiments, the present invention also provides an isolated polynucleotide comprising a nucleotide sequence that encodes i) a heavy chain polypeptide having the amino acid sequence as shown in SEQ ID NOs: 50, 51, 52, 150, 152, 156, 160, and 164, and/or ii) a light chain polypeptide having the amino acid sequence as shown in SEQ ID NOs: 53, 54, 55, 151, 154, 158, 162, and 166.

In another embodiment, the present invention provides a recombinant expression vector comprising a polynucleotide that encodes a Mab, or antigen-binding fragment thereof. In particular embodiments, the present invention also provides a recombinant expression vector comprising a polynucleotide that encodes (i) a heavy chain polypeptide having the amino acid sequence as shown in SEQ ID NOs: 50, 51, 52, 150, 152, 156, 160, and 164, and/or ii) a light chain polypeptide having the amino acid sequence as shown in SEQ ID NOs: 53, 54, 55, 151, 154, 158, 162, and 166.

When used herein, the term "hepcidin" refers to any form of the hepcidin protein known to be present in mammals. When used herein, the term "mature hepcidin" refers to any mature, bioactive form of the hepcidin protein expressed in mammals. When used herein, the phrase "human hepcidin" refers to any form of the hepcidin protein present in humans. When used herein, the phrase "mature human hepcidin" any mature, bioactive form of the hepcidin protein known to be present in humans. Preferably, "mature human hepcidin" refers to "human hepcidin-25", a mature form of human hepcidin having the amino acid sequence as shown in SEQ ID NO: 91.

The term "bioactivity" in reference to mature hepcidin polypeptides such as hepcidin-25 includes, but is not limited to, specific binding of mature hepcidin to its receptor FPN1, one or more FPN1-mediated functions of mature hepcidin, such as a) mature hepcidin-induced internalization and/or degradation of FPN1 (see, e.g., Nemeth, E., et al., Science, 306:2090-2093, (2004)), b) mature hepcidin regulation of FPN1-mediated i) iron efflux, ii) serum iron levels, iii) reticulocyte count, iv) red blood cell count, v) hemoglobin levels, vi) hematocrit, vii) expression levels of hepcidin polypeptides, and/or viii) tissue distribution of hepcidin polypeptides.

The phrase "human engineered antibodies" refers to certain antibodies disclosed herein as well as antibodies that have binding and functional properties according to the invention similar to the antibodies disclosed herein, and that have framework regions that are substantially human or fully human surrounding CDRs derived from a non-human antibody, or antigen-binding fragment thereof, disclosed herein. "Framework region" or "framework sequence" refers to any one of framework regions 1 to 4. Human engineered antibodies and antigen-binding fragments thereof encompassed by the present invention include molecules wherein any one or more of framework regions 1 to 4 is substantially or fully human, i.e., wherein any of the possible combinations of individual substantially or fully human framework regions 1 to 4, is present. For example, this includes molecules in which framework region 1 and framework region 2, framework region 1 and framework region 3, framework region 1, 2, and 3, etc., are substantially or fully human. Substantially human frameworks are those that have at least about 80% sequence identity to a known human germline framework sequence. Preferably, the substantially human frameworks have at least about 85%, about 90%, or about 95% sequence identity to a known human germline framework sequence.

Fully human frameworks are those that are identical to a known human germline framework sequence. Human framework germline sequences can be obtained from ImMunoGeneTics (IMGT) via their website http://imgt.cines.fr, or from *The Immunoglobulin Facts Book* by Marie-Paule Lefranc and Gerard Lefranc, Academic Press, 2001, ISBN 012441351. For example, germline light chain frameworks can be selected from the group consisting of: A11, A17, A18, A19, A20, A27, A30, L1, L11, L12, L2, L5, L15, L6, L8, O12, O2, and O8, and germline heavy chain framework regions can be selected from the group consisting of: VH2-5, VH2-26, VH2-70, VH3-20, VH3-72, VH1-46, VH3-9, VH3-66, VH3-74, VH4-31, VH1-18, VH1-69, VI-13-7, VH3-11, VH3-15, VH3-21, VH3-23, VH3-30, VH3-48, VH4-39, VH4-59, and VH5-51. Preferably, germline light chain frameworks are selected from the group consisting of O2, O18, and L12, L1 and germline heavy chain framework regions are selected from the group consisting of VH1-69, VH1-18, or VH1-46. More preferably, germline light chain frameworks are selected from the group consisting of O2 and L1, and germline heavy chain frameworks are selected from the group consisting of VH1-69 and VH1-18. Most preferably, the germline light chain framework is O2 and the germline heavy chain framework region is VH1-69.

In addition to the human engineered antibodies disclosed herein, human engineered antibodies exhibiting similar functional properties as the antibodies according to the present invention can be generated using several different methods. The antibodies specifically disclosed herein can be used as templates or parent antibodies to prepare additional antibodies. In one approach, the CDRs of a parent antibody are grafted into a human framework that has a high sequence identity with the parent antibody framework. The sequence identity of the new framework will generally be at least about 80%, at least about 85%, at least about 90%, at least about 95%, or at least about 99% identical to the sequence of the corresponding framework in the parent antibody. This grafting may result in a reduction in binding affinity compared to that of the parent antibody. If this is the case, the framework can be back-mutated to the parent framework at certain positions based on specific criteria disclosed by Queen, et al., Proc. Natl. Acad. Sci. USA., 88:2869 (1991). Additional references describing methods useful in humanizing mouse antibodies include U.S. Pat. Nos. 4,816,397; 5,225,539; and 5,693,761; computer programs ABMOD and ENCAD as described in Levitt, J., Mol. Biol. 168:595-620 (1983); and the method of Winter and co-workers (Jones, et al., Nature 321:522-525 (1986); Riechmann, et al., Nature, 332:323-327 (1988); and Verhoeyen, et al., Science, 239:1534-1536 (1988).

The identification of residues to consider for back-mutation can be carried out as follows:

When an amino acid falls under the following category, the framework amino acid of the human germ-line sequence that is being used (the "acceptor framework") is replaced by a framework amino acid from a framework of the parent antibody (the "donor framework"):

(a) the amino acid in the human framework region of the acceptor framework is unusual for human frameworks at that position, whereas the corresponding amino acid in the donor immunoglobulin is typical for human frameworks at that position;

(b) the position of the amino acid is immediately adjacent to one of the CDRs; or (c) any side chain atom of a framework amino acid is within about 5-6 angstroms (center-to-center) of any atom of a CDR amino acid in a three dimensional immunoglobulin model.

When each of the amino acids in the human framework region of the acceptor framework and a corresponding amino acid in the donor framework is generally unusual for human frameworks at that position, such amino acid can be replaced by an amino acid typical for human frameworks at that position. This back-mutation criterion enables one to recover the activity of the parent antibody.

Another approach to generating human engineered antibodies exhibiting similar functional properties to the antibodies disclosed herein involves randomly mutating amino acids within the grafted CDRs without changing the framework, and screening the resultant molecules for binding affinity and other functional properties that are as good as or better than those of the parent antibodies. Single mutations can also be introduced at each amino acid position within each CDR, followed by assessing the effects of such mutations on binding affinity and other functional properties. Single mutations producing improved properties can be combined to assess their effects in combination with one another.

Further, a combination of both of the foregoing approaches is possible. After CDR grafting, one can back-mutate specific framework regions in addition to introducing amino acid changes in the CDRs. This methodology is described in Wu, et al., *J. Mol. Biol.* 294:151-162 (1999). Preferably, amino acid substitution within the frameworks is restricted to one, two, or three positions within any one or more of the light chain and/or heavy chain framework regions disclosed herein (i.e., framework regions shown in FIGS. 2-5). Preferably, amino acid substitution within the CDRs is restricted to one, two, or three positions within any one or more of the three light chain and/or heavy chain CDRs. Combinations of the various changes described within the framework regions and the CDRs are also contemplated herein. In particular embodiments of this aspect of the invention, all light and heavy chain variable region framework regions of such human engineered Mabs, or antigen-binding fragments thereof, are fully human.

Tables 1A and 1B below depict the CDR amino acid sequences and consensus amino acid sequences of preferred antibodies, or antigen-binding fragments thereof, of the present invention. Tables 2A and 2B below depict the CDR amino acid sequences and consensus amino acid sequences of more preferred antibodies, or antigen-binding fragments thereof, of the present invention.

TABLE 1A

| Fab | HCDR1 | HCDR2 | HCDR3 |
|---|---|---|---|
| 34A9 | GYAFTNFLIE (SEQ ID NO: 17) | TINPETGGTKYNEKFRG (SEQ ID NO: 18) | EFFDY (SEQ ID NO: 19) |
| 1B1 | GYAFTSFLIE (SEQ ID NO: 23) | (SEQ ID NO: 18) | (SEQ ID NO: 19) |

TABLE 1A-continued

| Fab | HCDR1 | HCDR2 | HCDR3 |
|---|---|---|---|
| 1D2 | (SEQ ID NO: 17) | TINPRTGGTKYNEKFRG (SEQ ID NO: 24) | (SEQ ID NO: 19) |
| 1E3 | (SEQ ID NO: 17) | TINPKTGGTKYNEKFRG (SEQ ID NO: 25) | (SEQ ID NO: 19) |
| 2A6 | (SEQ ID NO: 17) | TINPETGGTKYNAKFRG (SEQ ID NO: 26) | (SEQ ID NO: 19) |
| 2H10 | (SEQ ID NO: 17) | (SEQ ID NO: 18) | (SEQ ID NO: 19) |
| 3A8 | (SEQ ID NO: 17) | (SEQ ID NO: 18) | (SEQ ID NO: 19) |
| 2G9 | (SEQ ID NO: 17) | (SEQ ID NO: 18) | (SEQ ID NO: 19) |
| 1A3 | (SEQ ID NO: 23) | (SEQ ID NO: 25) | (SEQ ID NO: 19) |
| 2E2 | (SEQ ID NO: 23) | (SEQ ID NO: 24) | (SEQ ID NO: 19) |
| 2A5 | (SEQ ID NO: 23) | (SEQ ID NO: 25) | (SEQ ID NO: 19) |
| 2B2 | (SEQ ID NO: 23) | (SEQ ID NO: 25) | (SEQ ID NO: 19) |
| 1D1 | (SEQ ID NO: 23) | TINPKTGGTKYNAKFRG (SEQ ID NO: 34) | (SEQ ID NO: 19) |
| 1E2 | (SEQ ID NO: 23) | (SEQ ID NO: 24) | (SEQ ID NO: 19) |
| hu-1 | (SEQ ID NO: 23) | (SEQ ID NO: 24) | (SEQ ID NO: 19) |
| 1G9 | (SEQ ID NO: 23) | (SEQ ID NO: 24) | (SEQ ID NO: 19) |
| huG1 | (SEQ ID NO: 23) | TSNPRTGGTKYNEKFRG (SEQ ID NO: 35) | (SEQ ID NO: 19) |
| huA2 | (SEQ ID NO: 23) | TINPRTGGTKYKEKFRG (SEQ ID NO: 36) | (SEQ ID NO: 19) |
| huA3 | (SEQ ID NO: 23) | (SEQ ID NO: 24) | (SEQ ID NO: 19) |
| huB3 | (SEQ ID NO: 23) | (SEQ ID NO: 24) | (SEQ ID NO: 19) |
| huD3 | (SEQ ID NO: 23) | (SEQ ID NO: 24) | (SEQ ID NO: 19) |
| huH5 | (SEQ ID NO: 23) | (SEQ ID NO: 24) | (SEQ ID NO: 19) |
| huH6 | (SEQ ID NO: 23) | (SEQ ID NO: 24) | (SEQ ID NO: 19) |
| 1D5 | (SEQ ID NO: 23) | TSNPRTGGTKYKEKFRG (SEQ ID NO: 41) | (SEQ ID NO: 19) |
| 2G5 | (SEQ ID NO: 23) | (SEQ ID NO: 41) | (SEQ ID NO: 19) |
| 3D8 | (SEQ ID NO: 23) | (SEQ ID NO: 41) | (SEQ ID NO: 19) |
| *C1 | GYAFTX$_1$FLIE (SEQ ID NO: 30) | TINPX$_2$TGGTKYNX$_3$KFRG (SEQ ID NO: 31) | (SEQ ID NO: 19) |
| *C2 | (SEQ ID NO: 30) | TX$_6$NPX$_2$TGGTKY X$_7$X$_3$KFRG (SEQ ID NO: 43) | (SEQ ID NO: 19) |
| *C3 | (SEQ ID NO: 23) | (SEQ ID NO: 41) | (SEQ ID NO: 19) |
| *C4 | (SEQ ID NO: 23) | (SEQ ID NO: 41) | (SEQ ID NO: 19) |
| *C5 | (SEQ ID NO: 30) | (SEQ ID NO: 43) | (SEQ ID NO: 19) |

TABLE 1B

| Fab | LCDR1 | LCDR2 | LCDR3 |
|---|---|---|---|
| 34A9 | RASKSISKYLA (SEQ ID NO: 20) | AGSTLHS (SEQ ID NO: 21) | QQHNEYPYT (SEQ ID NO: 22) |
| 1B1 | (SEQ ID NO: 20) | (SEQ ID NO: 21) | (SEQ ID NO: 22) |
| 1D2 | (SEQ ID NO: 20) | (SEQ ID NO: 21) | (SEQ ID NO: 22) |
| 1E3 | (SEQ ID NO: 20) | (SEQ ID NO: 21) | (SEQ ID NO: 22) |
| 2A6 | (SEQ ID NO: 20) | (SEQ ID NO: 21) | (SEQ ID NO: 22) |
| 2H10 | (SEQ ID NO: 20) | AGSKLHS (SEQ ID NO: 27) | (SEQ ID NO: 22) |
| 3A8 | (SEQ ID NO: 20) | AGSRLHS (SEQ ID NO: 28) | (SEQ ID NO: 22) |
| 2G9 | (SEQ ID NO: 20) | AGSTLHS (SEQ ID NO: 21) | FQHNEYPYT (SEQ ID NO: 29) |
| 1A3 | (SEQ ID NO: 20) | (SEQ ID NO: 21) | (SEQ ID NO: 22) |
| 2E2 | (SEQ ID NO: 20) | (SEQ ID NO: 21) | (SEQ ID NO: 22) |
| 2A5 | (SEQ ID NO: 20) | (SEQ ID NO: 27) | (SEQ ID NO: 22) |
| 2B2 | (SEQ ID NO: 20) | (SEQ ID NO: 27) | (SEQ ID NO: 29) |
| 1D1 | (SEQ ID NO: 20) | (SEQ ID NO: 21) | (SEQ ID NO: 29) |
| 1E2 | (SEQ ID NO: 20) | (SEQ ID NO: 21) | (SEQ ID NO: 29) |
| 1G9 | (SEQ ID NO: 20) | (SEQ ID NO: 27) | (SEQ ID NO: 29) |
| hu-1 | (SEQ ID NO: 20) | (SEQ ID NO: 27) | (SEQ ID NO: 29) |
| huG1 | (SEQ ID NO: 20) | (SEQ ID NO: 27) | (SEQ ID NO: 29) |
| huA2 | (SEQ ID NO: 20) | (SEQ ID NO: 27) | (SEQ ID NO: 29) |
| huA3 | RASKSISKYTA (SEQ ID NO: 37) | (SEQ ID NO: 27) | (SEQ ID NO: 29) |
| huB3 | RASKSISKYSA (SEQ ID NO: 38) | (SEQ ID NO: 27) | (SEQ ID NO: 29) |
| huD3 | RASKSISKYAA (SEQ ID NO: 39) | (SEQ ID NO: 27) | (SEQ ID NO: 29) |
| huH5 | (SEQ ID NO: 20) | (SEQ ID NO: 27) | (SEQ ID NO: 22) |
| huH6 | (SEQ ID NO: 20) | (SEQ ID NO: 27) | HQHNEYPYT (SEQ ID NO: 40) |
| 1D5 | (SEQ ID NO: 39) | (SEQ ID NO: 27) | (SEQ ID NO: 22) |
| 2G5 | (SEQ ID NO: 38) | (SEQ ID NO: 27) | (SEQ ID NO: 22) |
| 3D8 | (SEQ ID NO: 37) | (SEQ ID NO: 27) | (SEQ ID NO: 22) |
| *C1 | (SEQ ID NO: 20) | AGSX₄LHS (SEQ ID NO: 32) | X₅QHNEYPYT (SEQ ID NO: 33) |
| *C2 | RASKSISKY X₈A (SEQ ID NO: 42) | (SEQ ID NO: 32) | (SEQ ID NO: 33) |
| *C3 | (SEQ ID NO: 42) | (SEQ ID NO: 27) | (SEQ ID NO: 22) |
| *C4 | (SEQ ID NO: 42) | (SEQ ID NO: 32) | (SEQ ID NO: 33) |
| *C5 | (SEQ ID NO: 42) | (SEQ ID NO: 32) | (SEQ ID NO: 33) |

*Tables 1A and 1B, consensus sequences 1-5 (C1-C5), wherein $X_1$ is N or S; $X_2$ is E, K, or R; $X_3$ is E or A; $X_6$ is S or I; $X_7$ is N or K; $X_4$ is T, K, or R; $X_5$ is F, H, Q; $X_8$ is L, T, S, or A.

TABLE 2A

| Fab | HCDR1 | HCDR2 | HCDR3 |
|---|---|---|---|
| 3D8 | GYAFTSFLIE (SEQ ID NO: 23) | TSNPRTGGTKYKEKFRG (SEQ ID NO: 41) | EFFDY (SEQ ID NO: 19) |
| 1G9 | (SEQ ID NO: 23) | (SEQ ID NO: 24) | (SEQ ID NO: 19) |
| 2G2 | GRAFTSFLIE (SEQ ID NO: 103) | (SEQ ID NO: 41) | (SEQ ID NO: 19) |
| 2A1 | GKAFTSFLIE (SEQ ID NO: 104) | (SEQ ID NO: 41) | (SEQ ID NO: 19) |
| 4H2 | GYRFTSFLIE (SEQ ID NO: 105) | (SEQ ID NO: 41) | (SEQ ID NO: 19) |
| 4C2 | GYAFRSFLIE (SEQ ID NO: 106) | (SEQ ID NO: 41) | (SEQ ID NO: 19) |
| 4A11 | (SEQ ID NO: 23) | TSNPRTRGTKYKEKFRG (SEQ ID NO: 108) | (SEQ ID NO: 19) |
| 5A2 | (SEQ ID NO: 23) | TSNPRTGRTKYKEKFRG (SEQ ID NO: 109) | (SEQ ID NO: 19) |
| 4A10 | (SEQ ID NO: 23) | TSNPRTGGRKYKEKFRG (SEQ ID NO: 110) | (SEQ ID NO: 19) |
| 1E3 | (SEQ ID NO: 23) | TSNPRTGGTKYKTKFRG (SEQ ID NO: 111) | (SEQ ID NO: 19) |
| 1F10 | (SEQ ID NO: 23) | TSNPRTGGTKYKSKFRG (SEQ ID NO: 112) | (SEQ ID NO: 19) |
| 3D1 | (SEQ ID NO: 23) | TSNPRTGGTKYKWKFRG (SEQ ID NO: 113) | (SEQ ID NO: 19) |

TABLE 2A-continued

| Fab | HCDR1 | HCDR2 | HCDR3 |
|---|---|---|---|
| 1E4 | (SEQ ID NO: 23) | TSNPRTGGTKYKEVFRG (SEQ ID NO: 114) | (SEQ ID NO: 19) |
| 4H6 | (SEQ ID NO: 23) | TSNPRTGGTKYKEKFRR (SEQ ID NO: 115) | (SEQ ID NO: 19) |
| 1G3 | (SEQ ID NO: 23) | (SEQ ID NO: 41) | EFFVY (SEQ ID NO: 119) |
| 1B5 | (SEQ ID NO: 23) | (SEQ ID NO: 41) | (SEQ ID NO: 19) |
| L2.2 | (SEQ ID NO: 23) | (SEQ ID NO: 41) | (SEQ ID NO: 19) |
| L2.6 | (SEQ ID NO: 23) | (SEQ ID NO: 41) | (SEQ ID NO: 19) |
| 7C8 | (SEQ ID NO: 23) | (SEQ ID NO: 41) | (SEQ ID NO: 19) |
| 6H4 | (SEQ ID NO: 23) | (SEQ ID NO: 41) | (SEQ ID NO: 19) |
| 7E4 | (SEQ ID NO: 23) | (SEQ ID NO: 41) | (SEQ ID NO: 19) |
| Combi-11 | (SEQ ID NO: 23) | TSNPRTGRTKYKSKFRG (SEQ ID NO: 116) | (SEQ ID NO: 19) |
| 4A10-3 | (SEQ ID NO: 23) | (SEQ ID NO: 110) | (SEQ ID NO: 19) |
| L2.2-4 | (SEQ ID NO: 23) | (SEQ ID NO: 110) | (SEQ ID NO: 19) |
| 1F8 | GYRFTSFLIE (SEQ ID NO: 105) | TSNPRTGRTKYKTKFRG (SEQ ID NO: 117) | (SEQ ID NO: 19) |
| 1B7 | GYRFTSFLIE (SEQ ID NO: 105) | (SEQ ID NO: 41) | (SEQ ID NO: 119) |
| Com11GY | (SEQ ID NO: 23) | (SEQ ID NO: 112) | (SEQ ID NO: 19) |
| Consensus 6* | $GX_1X_2FX_3SFLIE$ (SEQ ID NO: 107) | $TSNPRTX_4X_5X_6KYKX_7X_8FRX_9$ (SEQ ID NO: 118) | $EFFX_{10}Y$ (SEQ ID NO: 120) |

TABLE 2B

| Fab | LCDR1 | LCDR2 | LCDR3 |
|---|---|---|---|
| 3D8 | RASKSISKYTA (SEQ ID NO: 37) | AGSKLHS (SEQ ID NO: 27) | QQHNEYPYT (SEQ ID NO: 22) |
| 1G9 | (SEQ ID NO: 20) | (SEQ ID NO: 27) | (SEQ ID NO: 29) |
| 2G2 | (SEQ ID NO: 37) | (SEQ ID NO: 27) | (SEQ ID NO: 22) |
| 2A1 | (SEQ ID NO: 37) | (SEQ ID NO: 27) | (SEQ ID NO: 22) |
| 4H2 | (SEQ ID NO: 37) | (SEQ ID NO: 27) | (SEQ ID NO: 22) |
| 4C2 | (SEQ ID NO: 37) | (SEQ ID NO: 27) | (SEQ ID NO: 22) |
| 4A11 | (SEQ ID NO: 37) | (SEQ ID NO: 27) | (SEQ ID NO: 22) |
| 5A2 | (SEQ ID NO: 37) | (SEQ ID NO: 27) | (SEQ ID NO: 22) |
| 4A10 | (SEQ ID NO: 37) | (SEQ ID NO: 27) | (SEQ ID NO: 22) |
| 1E3 | (SEQ ID NO: 37) | (SEQ ID NO: 27) | (SEQ ID NO: 22) |
| 1F10 | (SEQ ID NO: 37) | (SEQ ID NO: 27) | (SEQ ID NO: 22) |
| 3D1 | (SEQ ID NO: 37) | (SEQ ID NO: 27) | (SEQ ID NO: 22) |
| 1E4 | (SEQ ID NO: 37) | (SEQ ID NO: 27) | (SEQ ID NO: 22) |
| 4H6 | (SEQ ID NO: 37) | (SEQ ID NO: 27) | (SEQ ID NO: 22) |

TABLE 2B-continued

| Fab | LCDR1 | LCDR2 | LCDR3 |
|---|---|---|---|
| 1G3 | (SEQ ID NO: 37) | (SEQ ID NO: 27) | (SEQ ID NO: 22) |
| 1B5 | (SEQ ID NO: 37) | AGSKRHS (SEQ ID NO: 121) | (SEQ ID NO: 22) |
| L2.2 | (SEQ ID NO: 37) | AGSKLRS (SEQ ID NO: 122) | (SEQ ID NO: 22) |
| L2.6 | (SEQ ID NO: 37) | AGSKLVS (SEQ ID NO: 123) | (SEQ ID NO: 22) |
| 7C8 | (SEQ ID NO: 37) | AGSKLYS (SEQ ID NO: 124) | (SEQ ID NO: 22) |
| 6H4 | (SEQ ID NO: 37) | AGSKLHW (SEQ ID NO: 125) | (SEQ ID NO: 22) |
| 7E4 | (SEQ ID NO: 37) | AGSKLHY (SEQ ID NO: 126) | (SEQ ID NO: 22) |
| Combi-11 | (SEQ ID NO: 37) | AGSKRHW (SEQ ID NO: 127) | (SEQ ID NO: 22) |
| 4A10-3 | (SEQ ID NO: 37) | (SEQ ID NO: 125) | (SEQ ID NO: 22) |
| L2.2-4 | (SEQ ID NO: 37) | (SEQ ID NO: 122) | (SEQ ID NO: 22) |
| 1F8 | (SEQ ID NO: 37) | AGSKRYY (SEQ ID NO: 128) | (SEQ ID NO: 22) |
| 1B7 | (SEQ ID NO: 37) | (SEQ ID NO:128) | (SEQ ID NO: 22) |
| Com11GY | (SEQ ID NO: 37) | AGSKRHY (SEQ ID NO: 177) | (SEQ ID NO: 22) |
| Consensus 6* | RASKSISKYTA (SEQ ID NO: 37) | AGSKX$_{11}$X$_{12}$X$_{13}$ (SEQ ID NO: 129) | QQHNEYPYT (SEQ ID NO: 22) |

*Tables 2A and 2B, consensus sequence 6, wherein X$_1$ is Y, R, or K; X$_2$ is A, or R; X$_3$ is T or R; X$_4$ is G or R; X$_5$ is G or R; X$_6$ is T, or R; X$_7$ is E, T, S, or W; X$_8$ is K or V; X$_9$ is G or R; X$_{10}$ is D or V; X$_{11}$ is L or R; X$_{12}$ is H, R, V, or Y; X$_{13}$ is S, W, or Y.

Even more preferred antibodies, or antigen-binding fragments, of the invention comprise a LCDR1, LCDR2, LCDR3, HCDR1, HCDR2, and HCDR3 comprising the amino acid sequences shown in SEQ ID NOs: 170, 171, 172, 23, 173, and 19, respectively, or SEQ ID NOs: 170, 171, 172, 182, 173, and 19, respectively. Even more preferred antibodies, or antigen-binding fragments, of the invention comprise a LCDR1, LCDR2, LCDR3, HCDR1, HCDR2, and HCDR3 comprising the amino acid sequences shown in SEQ ID NOs: 37, 174, 22, 175, 176, and 120, respectively. Based upon pharmacokinetic (e.g., see, Example 11) and pharmacodynamic (e.g., see Examples 10 and 12) characteristics as well as the functional properties of exemplary anti-FPN1 Mabs, or antigen-binding fragments thereof, (e.g., see, Examples 3 (epitope mapping), 4 (affinity), 5 (effect on ferritin concentration in cells in vitro), 6 (effect on binding of mature hepcidin by cells engineered to express a FPN1-GFP fusion in vitro), 7 and 9 (effect on hepcidin-induced internalization and degradation of FPN1 in vitro), and 8 (effect on serum iron levels in vivo)), the most preferred Mabs, or antigen-binding fragments thereof, of the present invention are Mabs 4A10-3, L2.2-4, and Com11GY, or antigen-binding fragments thereof. The amino acid sequences encoding the heavy chains, the light chains, the heavy and light chain variable regions, and the CDRs for Mabs 34A9, 1G9, 3D8, Combi11, 4A10-3, L2.2-4, 1B7, 1F8, and Com11GY are indicated below in Table 3(a) and Table 3(b) by reference to SEQ ID NOs.

TABLE 3(a)

| Mab | Heavy Chain | HCVR | HC CDR1 | HC CDR2 | HC CDR3 |
|---|---|---|---|---|---|
| 34A9 | 50 | 44 | 17 | 18 | 19 |
| 1G9 | 51 | 45 | 23 | 24 | 19 |
| 3D8 | 52 | 46 | 23 | 41 | 19 |
| Combi11 | 150 | 130 | 23 | 116 | 19 |
| 4A10-3 | 152 | 134 | 23 | 110 | 19 |
| L2.2-4 | 156 | 138 | 23 | 110 | 19 |
| 1B7 | 160 | 146 | 105 | 41 | 119 |
| 1F8 | 164 | 142 | 105 | 117 | 19 |
| Com11GY | 179 | 178 | 23 | 112 | 19 |

TABLE 3(b)

| Mab | Light Chain | LCVR | LC CDR1 | LC CDR2 | LC CDR3 |
|---|---|---|---|---|---|
| 34A9 | 53 | 47 | 20 | 21 | 22 |
| 1G9 | 54 | 48 | 20 | 27 | 29 |
| 3D8 | 55 | 49 | 37 | 27 | 22 |
| Combi-11 | 151 | 132 | 37 | 127 | 22 |
| 4A10-3 | 154 | 136 | 37 | 125 | 22 |
| L2.2-4 | 158 | 140 | 37 | 122 | 22 |
| 1B7 | 162 | 148 | 37 | 128 | 22 |
| 1F8 | 166 | 144 | 37 | 128 | 22 |
| Com11GY | 181 | 180 | 37 | 177 | 22 |

In some embodiments, the anti-FPN1 Mabs, or antigen-binding fragments thereof, disclosed herein may be used in combination with one or more ESAs in order to provide additional benefits with respect to increasing serum iron levels, increasing hematocrits, increasing hemoglobin levels, reducing the need for transfusion, and/or improving the functional status, productivity, and quality of life of anemic patients as compared to the administration of the ESA therapy alone. By the phrase "combination therapy" or "in combination with" it is meant an anti-FPN1 Mab, or antigen-binding fragment thereof, of the present invention is administered separately, simultaneously, or sequentially with another agent intended to increase serum iron levels, increase hematocrits, increase hemoglobin levels, reducing the need for transfusions, and/or improving the functional status, productivity, and quality of life of anemic patients as compared to the administration of the anti-FPN1 Mab, or antigen-binding fragment thereof, alone.

In some embodiments, an anti-FPN1 Mab, or antigen-binding fragment thereof, disclosed herein may be administered in lieu of ESA therapy in patients intolerant or unresponsive to ESA therapy.

The phrase "erythropoiesis stimulating agent" or "erythropoiesis stimulator" means a compound that directly or indirectly causes activation of the erythropoietin receptor, for example, by binding to and causing dimerization of the receptor or by stimulating endogenous erythropoietin expression. ESAs include erythropoietin and variants, analogs, or derivatives thereof that bind to and activate erythropoietin receptor; antibodies that bind to erythropoietin receptor and activate the receptor; or peptides that bind to and activate erythropoietin receptor; or small organic chemical compounds, optionally less than about 1000 Daltons in molecular weight, that bind to and activate erythropoietin receptor. ESAs include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), mimetic antibodies and HIF inhibitors (see U.S. Patent Publication No. 2005/0020487). Exemplary ESAs include erythropoietin, darbepoetin, erythropoietin agonist variants, and peptides or antibodies that bind and activate erythropoietin receptor including compounds reported in U.S. Patent Application Publication Nos. 2003/0215444 and 2006/0040858 as well as erythropoietin molecules or variants or analogs thereof also known in the art. Erythropoietin includes, but is not limited to, a polypeptide comprising the amino acid sequence as set forth in SEQ ID NO: 88. The term "epoetin", includes, but is not limited to, epoetin alfa, epoetin beta, epoetin delta, epoetin omega, epoetin iota, epoetin gamma, epoetin zeta, and the like. Additionally, an epoetin also includes any of the aforementioned epoetins which are chemically modified, e.g., with one or more water-soluble polymers such as, e.g., polyethylene glycol (including PEG-EPO-beta). Exemplary sequences, manufacture, purification and use of recombinant human erythropoietin are described in a number of patent publications, including, but not limited to, U.S. Pat. Nos. 4,703,008 and 4,667,016. Exemplary sequences, manufacture, purification and use of darbepoetin and other erythropoietin analogs are described in a number of patent publications, including Strickland et al., 91/05867, and PCT International Patent Application Publications Nos. WO 95/05465, WO 00/24893, and WO 01/81405. Derivatives of naturally occurring or analog polypeptides include those which have been chemically modified, for example, to attach water soluble polymers (e.g., pegylated), radionuclides, or other diagnostic or targeting or therapeutic moieties.

The term "erythropoietic activity" means activity to stimulate erythropoiesis as demonstrated in an in vivo assay, for example, the exhypoxic, polycythemic mouse assay (see, e.g., Cotes and Bangham, Nature, 191:1065 (1961)).

The term "epitope" refers to that portion of any molecule capable of being recognized by and bound by an antibody at one or more of the antibody's antigen-binding regions. Epitopes often consist of a chemically active surface grouping of molecules such as amino acids or sugar side chains, and have specific three dimensional structural characteristics as well as specific charge characteristics. The human FPN1 epitopes disclosed herein are presented in the context of the primary amino acid structure of FPN1 (SEQ ID NO: 1). However, some of the epitopes may be discontinuous rather than continuous as the amino acid residues, rather than being in continuous peptide linkage, may be in spatial proximity to each other as a consequence of the tertiary or quaternary structure of FPN1 and their resultant presentation on the surface of this molecule. Preferably, an anti-FPN1 Mab, or antigen-binding fragment thereof, of the present invention binds human FPN1 consisting of the amino acid sequence shown in SEQ ID NO:1 at an epitope comprising or consisting essentially of or consisting of an amino acid or amino acids localized to the amino acid sequence as shown in SEQ ID NO: 9. More preferably, an anti-FPN1 Mab, or antigen-binding fragment thereof, of the present invention binds human FPN1 consisting of the amino acid sequence shown in SEQ ID NO:1 at an epitope comprising or consisting essentially of or consisting of an amino acid or amino acids localized to an amino acid sequence selected from the group consisting of SEQ ID NOs: 12, 13, 14, 15, 16, and 95. Even more preferably, an anti-FPN1 Mab, or antigen-binding fragment thereof, of the present invention binds human FPN1 consisting of the amino acid sequence shown in SEQ ID NO: 1 at an epitope comprising or consisting essentially of or consisting of an amino acid or amino acids localized to an amino acid sequence selected from the group consisting of SEQ ID NOs: 12, 13, 14, 15, 16, and 95 but does not bind one or more peptides selected from the group consisting of SEQ ID NOS: 98, 183-214.

Antibodies of the present invention also bind Cynomolgus monkey FPN1 (SEQ ID NO: 3), facilitating obligatory preclinical safety and efficacy therapeutic drug development studies in one or more primate models.

The phrase "human ferroportin 1" or, alternatively, "human FPN1" refers to an iron transporting protein expressed in humans that has the amino acid sequence as shown in SEQ ID NO: 1, as well as to variants which retain the ability to export cellular iron in response to interaction with mature human hepcidin.

Preferably, an anti-FPN1 Mab, or antigen-binding fragment thereof, of the present invention comprises:
1) a light chain variable region and a heavy chain variable region as shown in SEQ ID NO: 136 and SEQ ID NO: 134, respectively;
2) a light chain variable region and a heavy chain variable region as shown in SEQ ID NO: 180 and SEQ ID NO: 178, respectively; or
3) a light chain variable region and a heavy chain variable region as shown in SEQ ID NO: 140 and SEQ ID NO: 138, respectively. Even more preferably, an anti-FPN1 Mab, or antigen-binding fragment thereof, of the present invention comprises:
1) a light chain and a heavy chain as shown in SEQ ID NO: 154 and SEQ ID NO: 152, respectively;
2) a light chain and a heavy chain as shown in SEQ ID NO: 181 and SEQ ID NO: 179, respectively; or
3) a light chain and a heavy chain as shown in SEQ ID NO: 158 and SEQ ID NO: 156, respectively. Even more preferably, the monoclonal antibody or antigen binding fragment of the invention comprises:

1) two light chain polypeptides and two heavy chain polypeptides, and wherein each of the light chain polypeptides have the amino acid sequence as shown in SEQ ID NO: 154 and each of the heavy chain polypeptides have the amino acid sequence as shown in SEQ ID NO: 152;

2) two light chain polypeptides and two heavy chain polypeptides, and wherein each of the light chain polypeptides have the amino acid sequence as shown in SEQ ID NO: 181 and each of the heavy chain polypeptides have the amino acid sequence as shown in SEQ ID NO: 179; or 3) two light chain polypeptides and two heavy chain polypeptides, and wherein each of the light chain polypeptides have the amino acid sequence as shown in SEQ ID NO: 158 and each of the heavy chain polypeptides have the amino acid sequence as shown in SEQ ID NO: 156. Even more preferably, the monoclonal antibody or antigen binding fragment of the invention binds human ferroportin 1 with a $K_D$ less than about 10 nM as determined by surface plasmon resonance at 25° C. Even more preferably, the monoclonal antibody or antigen binding fragment of the invention comprises a Fab, wherein the Fab binds human ferroportin 1 with a $K_D$ less than about 100 nM as determined by surface plasmon resonance at 37° C. Even more preferably, the Fab has a dissociation rate ($k_{off}$) between about $7.5 \times 10^{-3}$ s$^{-1}$ and about $9 \times 10^{-4}$ s$^{-1}$ as determined by SPR at 37° C. for human ferroportin 1. Even more preferably, the Fab binds human ferroportin 1 with a $K_D$ of between about 100 nM to about 1 nM. Even more preferably, the Fab binds human ferroportin 1 with a $K_D$ of between about 10 nM to about 0.5 nM. Even more preferably, the monoclonal antibody or antigen-binding fragment has an $IC_{50}$ between about 100 nM and about 1 nM in an in vitro assay of hepcidin-25 bioactivity. Even more preferably, the monoclonal antibody or antigen-binding fragment thereof has an $IC_{50}$ between about 100 nM and about 10 nM in an in vitro assay of hepcidin-25 bioactivity. Even more preferably, the hepcidin-25 bioactivity is ferroportin 1 internalization and/or degradation. Even more preferably, the monoclonal antibody or antigen-binding fragment thereof has an $IC_{50}$ between about 100 nM and about 1 nM in an in vivo assay of hepcidin-25 bioactivity. Even more preferably, the in vivo assay of hepcidin-25 bioactivity measures an IL-6-induced decrease in serum iron levels in a primate. Most preferably, the anti-FPN1 Mabs, or antigen-binding fragments thereof, do not bind one or more peptides selected from the group consisting of SEQ ID NOS: 98, 183-214.

In particular embodiments, the anti-FPN1 Mabs, or antigen-binding fragments thereof, of the present invention are characterized by binding human FPN1 consisting of the amino acid sequence shown in SEQ ID NO:1 at an epitope comprising or consisting essentially of or consisting of an amino acid or amino acids localized to an amino acid sequence selected from the group consisting of SEQ ID NOs: 12, 13, 14, 15, 16, and 95 with a $K_D$ less than about 100 nM, less than about 75 nM, less than about 50 nM, less than about 25 nM, or less than about 10 nM as determined by SPR, preferably, at 25° C. for Mabs and 37° C. for Fabs. Preferably, the anti-FPN1 Mabs, or antigen-binding fragments thereof, do not bind one or more peptides selected from the group consisting of SEQ ID NOS: 98, 183-214.

In particular embodiments, the anti-FPN1 Mabs, or antigen-binding fragments thereof, of the present invention are characterized by binding human FPN1 consisting of the amino acid sequence shown in SEQ ID NO:1 at an epitope comprising or consisting essentially of or consisting of an amino acid or amino acids localized to an amino acid sequence selected from the group consisting of SEQ ID NOs: 12, 13, 14, 15, 16, and 95 with a $K_D$ between about 100 nM to about 0.5 nM, preferably, between about 100 nM to about 0.5 nM, more preferably, between about 75 nM to about 5 nM, even more preferably, between about 50 nM to about 10 nM, even more preferably, between about 15 nM to about 10 nM, even more preferably, between about 10 nM to about 0.5 nM, even more preferably, between about 5 nM to about 0.5 nM, even more preferably, between about 5 nM to about 0.7 nM, even more preferably, between about 3 nM to about 0.7 nM, or most preferably, from about 3 nM to about 1 nM, as determined by SPR, preferably, at 25° C. for Mabs and 37° C. for Fabs. Preferably, the anti-FPN1 Mabs, or antigen-binding fragments thereof, do not bind one or more peptides selected from the group consisting of SEQ ID NOS: 98, 183-214.

In particular embodiments, the anti-FPN1 Mabs, or antigen-binding fragments thereof, of the present invention are characterized by binding human FPN1 consisting of the amino acid sequence shown in SEQ ID NO:1 at an epitope comprising or consisting essentially of or consisting of an amino acid or amino acids localized to an amino acid sequence selected from the group consisting of SEQ ID NOs: 12, 13, 14, 15, 16, and 95 with a dissociation rate ($k_{off}$) for human ferroportin 1 between about $7.5 \times 10^{-3}$ s$^{-1}$ and about $1 \times 10^{-4}$ s$^{-1}$, preferably between about $2.5 \times 10^{-3}$ s$^{-1}$ and about $1 \times 10^{-4}$ s$^{-1}$, more preferably between about $1 \times 10^{-3}$ s$^{-1}$ and about $1 \times 10^{-4}$ s$^{-1}$, and even more preferably between about $5 \times 10^{-4}$ s$^{-1}$ and about $1 \times 10^{-4}$ s$^{-1}$, as determined by SPR, preferably, at 25° C. for Mabs and 37° C. for Fabs. Preferably, the anti-FPN1 Mabs, or antigen-binding fragments thereof, do not bind one or more peptides selected from the group consisting of SEQ ID NOS: 98, 183-214.

In particular embodiments, the anti-FPN1 Mabs, or antigen-binding fragments thereof, of the present invention are characterized by binding human FPN1 consisting of the amino acid sequence shown in SEQ ID NO:1 at an epitope comprising or consisting essentially of or consisting of an amino acid or amino acids localized to an amino acid sequence selected from the group consisting of SEQ ID NOs: 12, 13, 14, 15, 16, and 95 with a $K_D$ less than about 100 nM, less than about 75 nM, less than about 50 nM, less than about 25 nM, or less than about 10 nM and a dissociation rate ($k_{off}$) for human ferroportin 1 between about $7.5 \times 10^{-3}$ s$^{-1}$ and about $1 \times 10^{-4}$ s$^{-1}$, preferably between about $2.5 \times 10^{-3}$ s$^{-1}$ and about $1 \times 10^{-4}$ s$^{-1}$, more preferably between about $1 \times 10^{-3}$ s$^{-1}$ and about $1 \times 10^{-4}$ s$^{-1}$, and even more preferably between about $5 \times 10^{-4}$ s$^{-1}$ and about $1 \times 10^{-4}$ s$^{-1}$, as determined by SPR, preferably, at 25° C. for Mabs and 37° C. for Fabs. Preferably, the anti-FPN1 Mabs, or antigen-binding fragments thereof, do not bind one or more peptides selected from the group consisting of SEQ ID NOS: 98, 183-214.

In particular embodiments, the anti-FPN1 Mabs, or antigen-binding fragments thereof, of the present invention are characterized by binding human FPN1 consisting of the amino acid sequence shown in SEQ ID NO:1 at an epitope comprising or consisting essentially of or consisting of an amino acid or amino acids localized to an amino acid sequence selected from the group consisting of SEQ ID NOs: 12, 13, 14, 15, 16, and 95 with a $K_D$ between about 100 nM to about 0.5 nM, preferably, between about 100 nM to about 1 nM, more preferably, between about 75 nM to about 5 nM, even more preferably, between about 50 nM to about 10 nM, even more preferably, between about 15 nM to about 10 nM, even more preferably, between about 10 nM to about 0.5 nM, even more preferably, between about 5 nM to about 0.5 nM, even more preferably, between about 5 nM to about 0.7 nM, even more preferably, between about 3 nM to about 0.7 nM, or most preferably, from about 3 nM to about 1 nM, and a dissociation rate ($k_{off}$) for human ferroportin 1 between about $7.5\times10^{-3}$ $s^{-1}$ and about $1\times10^{-4}$ $s^{-1}$, preferably between about $2.5\times10^{-3}$ $s^{-1}$ and about $1\times10^{-4}$ $s^{-1}$, more preferably between about $1\times10^{-3}$ $s^{-1}$ and about $1\times10^{-4}$ $s^{-1}$, and even more preferably between about $5\times10^{-4}$ $s^{-1}$ and about $1\times10^{-4}$ $s^{-1}$, as determined by SPR, preferably, at 25° C. for Mabs and 37° C. for Fabs. Preferably, the anti-FPN1 Mabs, or antigen-binding fragments thereof, do not bind one or more peptides selected from the group consisting of SEQ ID NOS: 98, 183-214.

In particular embodiments, the anti-FPN1 Mabs, or antigen-binding fragments thereof, of the present invention comprise a LCDR1, LCDR2, LCDR3, HCDR1, HCDR2, and HCDR3 comprising the amino acid sequence shown in SEQ ID NOs: 37, 129, 22, 107, 118, and 120, respectively, and bind human FPN1 consisting of the amino acid sequence shown in SEQ ID NO:1 at an epitope comprising or consisting essentially of or consisting of an amino acid or amino acids localized to an amino acid sequence selected from the group consisting of SEQ ID NOs: 12, 13, 14, 15, 16, and 95 with a $K_D$ less than about 100 nM, less than about 75 nM, less than about 50 nM, less than about 25 nM, or less than about 10 nM as determined by SPR, preferably, at 25° C. for Mabs and 37° C. for Fabs. Preferably, the anti-FPN1 Mabs, or antigen-binding fragments thereof, do not bind one or more peptides selected from the group consisting of SEQ ID NOS: 98, 183-214.

In some embodiments, the anti-FPN1 Mabs, or antigen-binding fragments thereof, of the present invention comprise a LCDR1, LCDR2, LCDR3, HCDR1, HCDR2, and HCDR3 comprising the amino acid sequence shown in SEQ ID NOs: 37, 129, 22, 107, 118, and 120, respectively, and bind human FPN1 consisting of the amino acid sequence shown in SEQ ID NO:1 at an epitope comprising or consisting essentially of or consisting of an amino acid or amino acids localized to an amino acid sequence selected from the group consisting of SEQ ID NOs: 12, 13, 14, 15, 16, and 95 with a $K_D$ between about 100 nM to about 0.5 nM, preferably, between about 100 nM to about 1 nM, more preferably, between about 75 nM to about 5 nM, even more preferably, between about 50 nM to about 10 nM, even more preferably, between about 15 nM to about 10 nM, even more preferably, between about 10 nM to about 0.5 nM, even more preferably, between about 5 nM to about 0.5 nM, even more preferably, between about 5 nM to about 0.7 nM, even more preferably, between about 3 nM to about 0.7 nM, or most preferably, from about 3 nM to about 1 nM as determined by SPR, preferably, at 25° C. for Mabs and 37° C. for Fabs. Preferably, the anti-FPN1 Mabs, or antigen-binding fragments thereof, do not bind one or more peptides selected from the group consisting of SEQ ID NOS: 98, 183-214.

In other embodiments, the present invention provides Mabs, or antigen-binding fragments thereof, comprising a LCDR1, LCDR2, LCDR3, HCDR1, HCDR2, and HCDR3 comprising the amino acid sequence shown in SEQ ID NOs: 37, 129, 22, 107, 118, and 120, respectively, that bind human FPN1 consisting of the amino acid sequence shown in SEQ ID NO:1 at an epitope comprising or consisting essentially of or consisting of an amino acid or amino acids localized to an amino acid sequence selected from the group consisting of SEQ ID NOs: 12, 13, 14, 15, 16, and 95 with a dissociation rate ($k_{off}$) for human ferroportin 1 between about $7.5\times10^{-3}$ $s^{-1}$ and about $1\times10^{-4}$ $s^{-1}$, preferably between about $2.5\times10^{-3}$ $s^{-1}$ and about $1\times10^{-4}$ $s^{-1}$, more preferably between about $1\times10^{-3}$ $s^{-1}$ and about $1\times10^{-4}$ $s^{-1}$, and even more preferably between about $5\times10^{-4}$ $s^{-1}$ and about $1\times10^{-4}$ $s^{-1}$, as determined by SPR, preferably, at 25° C. for Mabs and 37° C. for Fabs. Preferably, the anti-FPN1 Mabs, or antigen-binding fragments thereof, do not bind one or more peptides selected from the group consisting of SEQ ID NOS: 98, 183-214.

In particular embodiments, the anti-FPN1 Mabs, or antigen-binding fragments thereof, of the present invention comprise a LCDR1, LCDR2, LCDR3, HCDR1, HCDR2, and HCDR3 comprising the amino acid sequence shown in SEQ ID NOs: 37, 129, 22, 107, 118, and 120, respectively, and bind human FPN1 consisting of the amino acid sequence shown in SEQ ID NO:1 at an epitope comprising or consisting essentially of or consisting of an amino acid or amino acids localized to an amino acid sequence selected from the group consisting of SEQ ID NOs: 12, 13, 14, 15, 16, and 95 with a $K_D$ less than about 100 nM, less than about 75 nM, less than about 50 nM, less than about 25 nM, or less than about 10 nM and a dissociation rate ($k_{off}$) for human ferroportin 1 between about $7.5\times10^{-3}$ $s^{-1}$ and about $1\times10^{-4}$ $s^{-1}$, preferably between about $2.5\times10^{-3}$ $s^{-1}$ and about $1\times10^{-4}$ $s^{-1}$, more preferably between about $1\times10^{-3}$ $s^{-1}$ and about $1\times10^{-4}$ $s^{-1}$, and even more preferably between about $5\times10^{-4}$ $s^{-1}$ and about $1\times10^{-4}$ $s^{-1}$, as determined by SPR, preferably, at 25° C. for Mabs and 37° C. for Fabs. Preferably, the anti-FPN1 Mabs, or antigen-binding fragments thereof, do not bind one or more peptides selected from the group consisting of SEQ ID NOS: 98, 183-214.

In some embodiments, the anti-FPN1 Mabs, or antigen-binding fragments thereof, of the present invention comprise a LCDR1, LCDR2, LCDR3, HCDR1, HCDR2, and HCDR3 comprising the amino acid sequence shown in SEQ ID NOs: 37, 129, 22, 107, 118, and 120, respectively, and bind human FPN1 consisting of the amino acid sequence shown in SEQ ID NO:1 at an epitope comprising or consisting essentially of or consisting of an amino acid or amino acids localized to an amino acid sequence selected from the group consisting of SEQ ID NOs: 12, 13, 14, 15, 16, and 95 with a $K_D$ between about 100 nM to about 0.5 nM, preferably, between about 100 nM to about 1 nM, more preferably, between about 75 nM to about 5 nM, even more preferably, between about 50 nM to about 10 nM, even more preferably, between about 15 nM to about 10 nM, even more preferably, between about 10 nM to about 0.5 nM, even more preferably, between about 5 nM to about 0.5 nM, even more preferably, between about 5 nM to about 0.7 nM, even more preferably, between about 3 nM to about 0.7 nM, or most preferably, from about 3 nM to about 1 nM and a dissociation rate ($k_{off}$) for human ferroportin 1 between about $7.5\times10^{-3}$ $s^{-1}$ and about $1\times10^{-4}$ $s^{-1}$, preferably between about $2.5\times10^{-3}$ $s^{-1}$ and about $1\times10^{-4}$ $s^{-1}$, more preferably between about $1\times10^{-3}$ $s^{-1}$ and about $1\times10^{-4}$ $s^{-1}$, and even more preferably between about $5\times10^{-4}$ $s^{-1}$ and about $1\times10^{-4}$ $s^{-1}$, as determined by SPR, preferably, at 25° C. for Mabs and 37° C. for Fabs. Preferably, the anti-FPN1 Mabs, or antigen-binding fragments thereof, do not bind one or more peptides selected from the group consisting of SEQ ID NOS: 98, 183-214.

The term "inhibit" means the ability to antagonize, prohibit, prevent, restrain, slow, disrupt, eliminate, stop, reduce, or reverse the biological effects of FPN1 and/or bioactivity of mature hepcidin including, but not limited to, a mature human hepcidin bioactivity as measured herein in Examples 5-11, 13, or 14, for example.

In particular embodiments, the anti-FPN1 Mabs, or antigen-binding fragments thereof, of the present invention are characterized by having an $IC_{50}$ between about 250 nM and about 25 nM, preferably between 100 nM and about 25 nM, or more preferably between 50 nM and about 25 nM in an in vivo assay of hepcidin-25 bioactivity. Preferably, the in vivo assay measures an IL-6-induced decrease in serum iron levels.

Additionally, or alternatively, the anti-FPN1 Mabs, or antigen-binding fragments thereof, of the present invention are characterized by having an $IC_{50}$ between about 100 nM and about 1 nM, preferably, between about 75 nM and about 1 nM, more preferably, between about 50 nM and about 1 nM, even more preferably, between about 25 nM and about 1 nM in an in vitro assay of hepcidin-25 bioactivity. Preferably, the in vitro assay of hepcidin-25 bioactivity assay measures hepcidin-induced internalization and/or degradation of ferroportin 1. Even more preferably, the anti-FPN1 Mabs, or antigen-binding fragments thereof, do not bind one or more peptides selected from the group consisting of SEQ ID NOS: 98, 183-214.

In particular embodiments, the anti-FPN1 Mabs, or antigen-binding fragments thereof, of the present invention are characterized by binding human FPN1 consisting of the amino acid sequence shown in SEQ ID NO:1 at an epitope comprising or consisting essentially of or consisting of an amino acid or amino acids localized to an amino acid sequence selected from the group consisting of SEQ ID NOs: 12, 13, 14, 15, 16, and 95 with a $K_D$ less than about 100 nM, less than about 75 nM, less than about 50 nM, less than about 25 nM, or less than about 10 nM as determined by SPR, preferably, at 25° C. for Mabs and 37° C. for Fabs and an $IC_{50}$ between about 250 nM and about 25 nM, preferably between 100 nM and about 25 nM, or more preferably between 50 nM and about 25 nM in an in vivo assay of hepcidin-25 bioactivity. Preferably, the in vivo assay measures an IL-6-induced decrease in serum iron levels. Even more preferably, the anti-FPN1 Mabs, or antigen-binding fragments thereof, do not bind one or more peptides selected from the group consisting of SEQ ID NOS: 98, 183-214.

In particular embodiments, the anti-FPN1 Mabs, or antigen-binding fragments thereof, of the present invention are characterized by binding human FPN1 consisting of the amino acid sequence shown in SEQ ID NO:1 at an epitope comprising or consisting essentially of or consisting of an amino acid or amino acids localized to an amino acid sequence selected from the group consisting of SEQ ID NOs: 12, 13, 14, 15, 16, and 95 with a $K_D$ between about 100 nM to about 0.5 nM, preferably, between about 100 nM to about 1 nM, more preferably, between about 75 nM to about 5 nM, even more preferably, between about 50 nM to about 10 nM, even more preferably, between about 15 nM to about 10 nM, even more preferably, between about 10 nM to about 0.5 nM, even more preferably, between about 5 nM to about 0.5 nM, even more preferably, between about 5 nM to about 0.7 nM, even more preferably, between about 3 nM to about 0.7 nM, or most preferably, from about 3 nM to about 1 nM, as determined by SPR, preferably, at 25° C. for Mabs and 37° C. for Fabs and further characterized by having an $IC_{50}$ between about 250 nM and about 25 nM, preferably between 100 nM and about 25 nM, or more preferably between 50 nM and about 25 nM in an in vivo assay of hepcidin-25 bioactivity. Preferably, the in vivo assay measures an IL-6-induced decrease in serum iron levels. Even more preferably, the anti-FPN1 Mabs, or antigen-binding fragment, do not bind one or more peptides selected from the group consisting of SEQ ID NOS: 98, 183-214.

In particular embodiments, the anti-FPN1 Mabs, or antigen-binding fragments thereof, of the present invention are characterized by binding human FPN1 consisting of the amino acid sequence shown in SEQ ID NO:1 at an epitope comprising or consisting essentially of or consisting of an amino acid or amino acids localized to an amino acid sequence selected from the group consisting of SEQ ID NOs: 12, 13, 14, 15, 16, and 95 with a $K_D$ between about 100 nM to about 0.5 nM, preferably, between about 100 nM to about 1 nM, more preferably, between about 75 nM to about 5 nM, even more preferably, between about 50 nM to about 10 nM, even more preferably, between about 15 nM to about 10 nM, even more preferably, between about 10 nM to about 0.5 nM, even more preferably, between about 5 nM to about 0.5 nM, even more preferably, between about 5 nM to about 0.7 nM, even more preferably, between about 3 nM to about 0.7 nM, or most preferably, from about 3 nM to about 1 nM, as determined by SPR, preferably, at 25° C. for Mabs and 37° C. for Fabs, have a dissociation rate ($k_{off}$) for human ferroportin 1 between about $7.5\times10^{-3}$ s$^{-1}$ and about $1\times10^{-4}$ s$^{-1}$, preferably between about $2.5\times10^{-3}$ s$^{-1}$ and about $1\times10^{-4}$ s$^{-1}$, more preferably between about $1\times10^{-3}$ s$^{-1}$ and about $1\times10^{-4}$ s$^{-1}$, and even more preferably between about $5\times10^{-4}$ s$^{-1}$ and about $1\times10^{-4}$ s$^{-1}$, as determined by SPR, preferably, at 25° C. for Mabs and 37° C. for Fabs and are further characterized by having an $IC_{50}$ between about 250 nM and about 25 nM, preferably between 100 nM and about 25 nM, or more preferably between 50 nM and about 25 nM in an in vivo assay of hepcidin-25 bioactivity. Preferably, the in vivo assay measures an IL-6-induced decrease in serum iron levels. Even more preferably, the anti-FPN1 Mabs, or antigen-binding fragments thereof, do not bind one or more peptides selected from the group consisting of SEQ ID NOS: 98, 183-214.

In particular embodiments, the anti-FPN1 Mabs, or antigen-binding fragments thereof, of the present invention comprise a LCDR1, LCDR2, LCDR3, HCDR1, HCDR2, and HCDR3 comprising the amino acid sequence shown in SEQ ID NOs: 37, 129, 22, 107, 118, and 120, respectively, and bind human FPN1 consisting of the amino acid sequence shown in SEQ ID NO:1 at an epitope comprising or consisting essentially of or consisting of an amino acid or amino acids localized to an amino acid sequence selected from the group consisting of SEQ ID NOs: 12, 13, 14, 15, 16, and 95 with a $K_D$ less than about 100 nM, less than about 75 nM, less than about 50 nM, less than about 25 nM, or less than about 10 nM as determined by SPR, preferably, at 25° C. for Mabs and 37° C. for Fabs and a dissociation rate ($k_{off}$) for human ferroportin 1 between about $7.5\times10^{-3}$ s$^{-1}$ and about $1\times10^{-4}$ s$^{-1}$, preferably between about $2.5\times10^{-3}$ s$^{-1}$ and about $1\times10^{-4}$ s$^{-1}$, more preferably between about $1\times10^{-3}$ s$^{-1}$ and about $1\times10^{-4}$ s$^{-1}$, and even more preferably between about $5\times10^{-4}$ s$^{-1}$ and about $1\times10^{-4}$ s$^{-1}$, as determined by SPR, preferably, at 25° C. for Mabs and 37° C. for Fabs and are further characterized by having an $IC_{50}$ between about 250 nM and about 25 nM, preferably between 100 nM and about 25 nM, or more preferably between 50 nM and about 25 nM in an in vivo assay of hepcidin-25 bioactivity. Preferably, the in vivo assay measures an IL-6-induced decrease in serum iron levels. Even more preferably, the anti-FPN1 Mabs, or antigen-binding fragments thereof, do not bind one or more peptides selected from the group consisting of SEQ ID NOS: 98, 183-214.

In some embodiments, the anti-FPN1 Mabs, or antigen-binding fragments thereof, of the present invention comprise a LCDR1, LCDR2, LCDR3, HCDR1, HCDR2, and HCDR3 comprising the amino acid sequence shown in SEQ ID NOs: 37, 129, 22, 107, 118, and 120, respectively, and bind human FPN1 consisting of the amino acid sequence shown in SEQ ID NO:1 at an epitope comprising or consisting essentially of or consisting of an amino acid or amino acids localized to an amino acid sequence selected from the group consisting of SEQ ID NOs: 12, 13, 14, 15, 16, and 95 with a $K_D$ between about 100 nM to about 0.5 nM, preferably, between about 100 nM to about 1 nM, more preferably, between about 75 nM to about 5 nM, even more preferably, between about 50 nM to about 10 nM, even more preferably, between about 15 nM to about 10 nM, even more preferably, between about 10 nM to about 0.5 nM, even more preferably, between about 5 nM to about 0.5 nM, even more preferably, between about 5 nM to about 0.7 nM, even more preferably, between about 3 nM to about 0.7 nM, or most preferably, from about 3 nM to about 1 nM, as determined by SPR, preferably, at 25° C. for Mabs and 37° C. for Fabs and a dissociation rate ($k_{off}$) for human ferroportin 1 between about $7.5 \times 10^{-3}$ s$^{-1}$ and about $1 \times 10^{-4}$ s$^{-1}$, preferably between about $2.5 \times 10^{-3}$ s$^{-1}$ and about $1 \times 10^{-4}$ s$^{-1}$, more preferably between about $1 \times 10^{-3}$ s$^{-1}$ and about $1 \times 10^{-4}$ s$^{-1}$, and even more preferably between about $5 \times 10^{-4}$ s$^{-1}$ and about $1 \times 10^{-4}$ s$^{-1}$, as determined by SPR, preferably, at 25° C. for Mabs and 37° C. for Fabs and are further characterized by having an $IC_{50}$ between about 250 nM and about 25 nM, preferably between 100 nM and about 25 nM, or more preferably between 50 nM and about 25 nM in an in vivo assay of hepcidin-25 bioactivity. Preferably, the in vivo assay measures an IL-6-induced decrease in serum iron levels. Even more preferably, the anti-FPN1 Mabs, or antigen-binding fragments thereof, do not bind one or more peptides selected from the group consisting of SEQ ID NOS: 98, 183-214.

In some embodiments of the present invention, the anti-FPN1 Mabs, or antigen-binding fragments thereof, are characterized by binding human FPN1 consisting of the amino acid sequence shown in SEQ ID NO:1 at an epitope comprising or consisting essentially of or consisting of an amino acid or amino acids localized to an amino acid sequence selected from the group consisting of SEQ ID NOs: 12, 13, 14, 15, 16, and 95 with a $K_D$ less than about 75 nM, less than about 50 nM, less than about 25 nM, or less than about 10 nM as determined by SPR, preferably, at 25° C. for Mabs and 37° C. for Fabs and have an $IC_{50}$ between about 250 nM and about 25 nM, preferably between 100 nM and about 25 nM, or more preferably between 50 nM and about 25 nM in an in vivo assay of hepcidin-25 bioactivity and are further characterized by having an $IC_{50}$ between about 100 nM and about 1 nM, preferably, between about 75 nM and about 1 nM, more preferably, between about 50 nM and about 1 nM, even more preferably, between about 25 nM and about 1 nM in an in vitro assay of hepcidin-25 bioactivity. Preferably, the in vivo assay measures an IL-6-induced decrease in serum iron levels. Preferably, the in vitro assay of hepcidin-25 bioactivity assay measures hepcidin-induced internalization and/or degradation of ferroportin 1. Even more preferably, the anti-FPN1 Mabs, or antigen-binding fragments thereof, do not bind one or more peptides selected from the group consisting of SEQ ID NOS: 98, 183-214.

In particular embodiments, the anti-FPN1 Mabs, or antigen-binding fragments thereof, of the present invention are characterized by binding human FPN1 consisting of the amino acid sequence shown in SEQ ID NO:1 at an epitope comprising or consisting essentially of or consisting of an amino acid or amino acids localized to an amino acid sequence selected from the group consisting of SEQ ID NOs: 12, 13, 14, 15, 16, and 95 with a $K_D$ between about 100 nM to about 0.5 nM, preferably, between about 100 nM to about 1 nM, more preferably, between about 75 nM to about 5 nM, even more preferably, between about 50 nM to about 10 nM, even more preferably, between about 15 nM to about 10 nM, even more preferably, between about 10 nM to about 0.5 nM, even more preferably, between about 5 nM to about 0.5 nM, even more preferably, between about 5 nM to about 0.7 nM, even more preferably, between about 3 nM to about 0.7 nM, or most preferably, from about 3 nM to about 1 nM, as determined by SPR, preferably, at 25° C. for Mabs and 37° C. for Fabs and have an $IC_{50}$ between about 250 nM and about 25 nM, preferably, between 100 nM and about 25 nM, or more preferably, between 50 nM and about 25 nM in an in vivo assay of hepcidin-25 bioactivity and are further characterized by having an $IC_{50}$ between about 100 nM and about 1 nM, preferably, between about 75 nM and about 1 nM, more preferably, between about 50 nM and about 1 nM, even more preferably, between about 25 nM and about 1 nM in an in vitro assay of hepcidin-25 bioactivity. Preferably, the in vivo assay measures an IL-6-induced decrease in serum iron levels. Preferably, the in vitro assay of hepcidin-25 bioactivity assay measures hepcidin-induced internalization and/or degradation of ferroportin 1. Even more preferably, the anti-FPN1 Mabs, or antigen-binding fragments thereof, do not bind one or more peptides selected from the group consisting of SEQ ID NOS: 98, 183-214.

In some embodiments, the present invention provides Mabs, or antigen-binding fragments thereof, which bind human FPN1 consisting of the amino acid sequence shown in SEQ ID NO: 1 at an epitope comprising or consisting essentially of or consisting of an amino acid or amino acids localized to an amino acid sequence selected from the group consisting of SEQ ID NOs: 12, 13, 14, 15, 16, and 95 and 1) a $K_D$ between about 100 nM to about 0.5 nM, preferably, between about 100 nM to about 1 nM, more preferably, between about 75 nM to about 5 nM, even more preferably, between about 50 nM to about 10 nM, even more preferably, between about 15 nM to about 10 nM, even more preferably, between about 10 nM to about 0.5 nM, even more preferably, between about 5 nM to about 0.5 nM, even more preferably, between about 5 nM to about 0.7 nM, even more preferably, between about 3 nM to about 0.7 nM, or most preferably, from about 3 nM to about 1 nM, as determined by SPR, preferably, at 25° C. for Mabs and 37° C. for Fabs, 2) an $IC_{50}$ between about 250 nM and about 25 nM, preferably between 100 nM and about 25 nM, or more preferably between 50 nM and about 25 nM in an in vivo assay of hepcidin-25 bioactivity, 3) an $IC_{50}$ between about 100 nM and about 1 nM, preferably, between about 75 nM and about 1 nM, more preferably, between about 50 nM and about 1 nM, even more preferably, between about 25 nM and about 1 nM in an in vitro assay of hepcidin-25 bioactivity, and 4) a dissociation rate ($k_{off}$) for human ferroportin 1 between about $7.5 \times 10^{-3}$ s$^{-1}$ and about $1 \times 10^{-4}$ s$^{-1}$, preferably between about $2.5 \times 10^{-3}$ s$^{-1}$ and about $1 \times 10^{-4}$ s$^{-1}$, more preferably between about $1 \times 10^{-3}$ s$^{-1}$ and about $1 \times 10^{-4}$ s$^{-1}$, and even more preferably between about $5 \times 10^{-4}$ s$^{-1}$ and about $1 \times 10^{-4}$ s$^{-1}$, as determined by SPR, preferably, at 25° C. for Mabs and 37° C. for Fabs. Preferably, the in vivo assay measures an IL-6-induced decrease in serum iron levels. Preferably, the in vitro assay of hepcidin-25 bioactivity assay measures hepcidin-induced internalization and/or degradation of ferroportin 1. Even more preferably, the anti-FPN1 Mabs, or antigen-binding fragments thereof, do not bind one or more peptides selected from the group consisting of SEQ ID NOS: 98, 183-214.

In particular embodiments, the anti-FPN1 Mabs, or antigen-binding fragments thereof, of the present invention comprise a LCDR1, LCDR2, LCDR3, HCDR1, HCDR2, and HCDR3 comprising the amino acid sequence shown in SEQ ID NOs: 37, 129, 22, 107, 118, and 120, respectively, and are characterized by having an $IC_{50}$ between about 250 nM and about 25 nM, preferably between 100 nM and about 25 nM, or more preferably between 50 nM and about 25 nM in an in vivo assay of hepcidin-25 bioactivity. Preferably, the in vivo assay measures an IL-6-induced decrease in serum iron levels. Even more preferably, the anti-FPN1 Mabs, or antigen-binding fragments thereof, do not bind one or more peptides selected from the group consisting of SEQ ID NOS: 98, 183-214.

In particular embodiments, the anti-FPN1 Mabs, or antigen-binding fragments thereof, of the present invention comprise a LCDR1, LCDR2, LCDR3, HCDR1, HCDR2, and HCDR3 comprising the amino acid sequence shown in SEQ ID NOs: 37, 129, 22, 107, 118, and 120, respectively, and are characterized by having an $IC_{50}$ between about 250 nM and about 25 nM, preferably between 100 nM and about 25 nM, or more preferably between 50 nM and about 25 nM in an in vivo assay of hepcidin-25 bioactivity and an $IC_{50}$ between about 100 nM and about 1 nM, preferably, between about 75 nM and about 1 nM, more preferably, between about 50 nM and about 1 nM, even more preferably, between about 25 nM and about 1 nM in an in vitro assay of hepcidin-25 bioactivity. Preferably, the in vivo assay measures an IL-6-induced decrease in serum iron levels. Preferably, the in vitro assay of hepcidin-25 bioactivity assay measures hepcidin-induced internalization and/or degradation of ferroportin 1. Even more preferably, the anti-FPN1 Mabs, or antigen-binding fragments thereof, do not bind one or more peptides selected from the group consisting of SEQ ID NOS: 98, 183-214.

In particular embodiments, the anti-FPN1 Mabs, or antigen-binding fragments thereof, of the present invention comprise a LCDR1, LCDR2, LCDR3, HCDR1, HCDR2, and HCDR3 comprising the amino acid sequence shown in SEQ ID NOs: 37, 129, 22, 107, 118, and 120, respectively, and bind human FPN1 consisting of the amino acid sequence shown in SEQ ID NO:1 at an epitope comprising or consisting essentially of or consisting of an amino acid or amino acids localized to an amino acid sequence selected from the group consisting of SEQ ID NOs: 12, 13, 14, 15, 16, and 95 with a $K_D$ less than about 100 nM, less than about 75 nM, less than about 50 nM, less than about 25 nM, or less than about 10 nM as determined by SPR, preferably, at 25° C. for Mabs and 37° C. for Fabs and an $IC_{50}$ between about 250 nM and about 25 nM, preferably between 100 nM and about 25 nM, or more preferably between 50 nM and about 25 nM in an in vivo assay of hepcidin-25 bioactivity. Preferably, the in vivo assay measures an IL-6-induced decrease in serum iron levels. Even more preferably, the anti-FPN1 Mabs, or antigen-binding fragments thereof, do not bind one or more peptides selected from the group consisting of SEQ ID NOS: 98, 183-214.

In particular embodiments, the anti-FPN1 Mabs, or antigen-binding fragments thereof, of the present invention comprise a LCDR1, LCDR2, LCDR3, HCDR1, HCDR2, and HCDR3 comprising the amino acid sequence shown in SEQ ID NOs: 37, 129, 22, 107, 118, and 120, respectively, and bind human FPN1 consisting of the amino acid sequence shown in SEQ ID NO:1 at an epitope comprising or consisting essentially of or consisting of an amino acid or amino acids localized to an amino acid sequence selected from the group consisting of SEQ ID NOs: 12, 13, 14, 15, 16, and 95 with a $K_D$ between about 100 nM to about 0.5 nM, preferably, between about 100 nM to about 1 nM, more preferably, between about 75 nM to about 5 nM, even more preferably, between about 50 nM to about 10 nM, even more preferably, between about 15 nM to about 10 nM, even more preferably, between about 10 nM to about 0.5 nM, even more preferably, between about 5 nM to about 0.5 nM, even more preferably, between about 5 nM to about 0.7 nM, even more preferably, between about 3 nM to about 0.7 nM, or most preferably, from about 3 nM to about 1 nM, as determined by SPR, preferably, at 25° C. for Mabs and 37° C. for Fabs and further characterized by having an $IC_{50}$ between about 250 nM and about 25 nM, preferably between 100 nM and about 25 nM, or more preferably between 50 nM and about 25 nM in an in vivo assay of hepcidin-25 bioactivity. Preferably, the in vivo assay measures an IL-6-induced decrease in serum iron levels. Even more preferably, the anti-FPN1 Mabs, or antigen-binding fragments thereof, do not bind one or more peptides selected from the group consisting of SEQ ID NOS: 98, 183-214.

In particular embodiments, the anti-FPN1 Mabs, or antigen-binding fragments thereof, of the present invention comprise a LCDR1, LCDR2, LCDR3, HCDR1, HCDR2, and HCDR3 comprising the amino acid sequence shown in SEQ ID NOs: 37, 129, 22, 107, 118, and 120, respectively, and bind human FPN1 consisting of the amino acid sequence shown in SEQ ID NO:1 at an epitope comprising or consisting essentially of or consisting of an amino acid or amino acids localized to an amino acid sequence selected from the group consisting of SEQ ID NOs: 12, 13, 14, 15, 16, and 95 with a $K_D$ between about 100 nM to about 0.5 nM, preferably, between about 100 nM to about 1 nM, more preferably, between about 75 nM to about 5 nM, even more preferably, between about 50 nM to about 10 nM, even more preferably, between about 15 nM to about 10 nM, even more preferably, between about 10 nM to about 0.5 nM, even more preferably, between about 5 nM to about 0.5 nM, even more preferably, between about 5 nM to about 0.7 nM, even more preferably, between about 3 nM to about 0.7 nM, or most preferably, from about 3 nM to about 1 nM, as determined by SPR, preferably, at 25° C. for Mabs and 37° C. for Fabs, have a dissociation rate ($k_{off}$) for human ferroportin 1 between about $7.5 \times 10^{-3}$ s$^{-1}$ and about $1 \times 10^{-4}$ s$^{-1}$, preferably between about $2.5 \times 10^{-3}$ s$^{-1}$ and about $1 \times 10^{-4}$ s$^{-1}$, more preferably between about $1 \times 10^{-3}$ s$^{-1}$ and about $1 \times 10^{-4}$ s$^{-1}$, and even more preferably between about $5 \times 10^{-4}$ s$^{-1}$ and about $1 \times 10^{-4}$ s$^{-1}$, as determined by SPR, preferably, at 25° C. for Mabs and 37° C. for Fabs and are further characterized by having an $IC_{50}$ between about 250 nM and about 25 nM, preferably between 100 nM and about 25 nM, or more preferably between 50 nM and about 25 nM in an in vivo assay of hepcidin-25 bioactivity. Preferably, the in vivo assay measures an IL-6-induced decrease in serum iron levels. Even more preferably, the anti-FPN1 Mabs, or antigen-binding fragments thereof, do not bind one or more peptides selected from the group consisting of SEQ ID NOS: 98, 183-214.

In particular embodiments, the anti-FPN1 Mabs, or antigen-binding fragments thereof, of the present invention comprise a LCDR1, LCDR2, LCDR3, HCDR1, HCDR2, and HCDR3 comprising the amino acid sequence shown in SEQ ID NOs: 37, 129, 22, 107, 118, and 120, respectively, and bind human FPN1 consisting of the amino acid sequence shown in SEQ ID NO:1 at an epitope comprising or consisting essentially of or consisting of an amino acid or amino acids localized to an amino acid sequence selected from the group consisting of SEQ ID NOs: 12, 13, 14, 15, 16, and 95 with a $K_D$ less than about 100 nM, less than about 75 nM, less than about 50 nM, less than about 25 nM, or less than about 10 nM as determined by SPR, preferably, at 25° C. for Mabs and 37° C. for Fabs and a dissociation rate ($k_{off}$) for human ferroportin 1 between about $7.5 \times 10^{-3}$ s$^{-1}$ and about $1 \times 10^{-4}$ s$^{-1}$, preferably between about $2.5 \times 10^{-3}$ s$^{-1}$ and about $1 \times 10^{-4}$ s$^{-1}$, more preferably between about $1 \times 10^{-3}$ s$^{-1}$ and about $1 \times 10^{-4}$ s$^{-1}$, and even more preferably between about $5 \times 10^{-4}$ s$^{-1}$ and about $1 \times 10^{-4}$ s$^{-1}$, as determined by SPR, preferably, at 25° C. for Mabs and 37° C. for Fabs and are further characterized by having an $IC_{50}$ between about 250 nM and about 25 nM, preferably between 100 nM and about 25 nM, or more preferably between 50 nM and about 25 nM in an in vivo assay of hepcidin-25 bioactivity. Preferably, the in vivo assay measures an IL-6-induced decrease in serum iron levels. Even more preferably, the anti-FPN1 Mabs, or antigen-binding fragments thereof, do not bind one or more peptides selected from the group consisting of SEQ ID NOS: 98, 183-214.

In some embodiments of the present invention, the anti-FPN1 Mabs, or antigen-binding fragments thereof, comprise a LCDR1, LCDR2, LCDR3, HCDR1, HCDR2, and HCDR3 comprising the amino acid sequence shown in SEQ ID NOs: 37, 129, 22, 107, 118, and 120, respectively, and bind human FPN1 consisting of the amino acid sequence shown in SEQ ID NO:1 at an epitope comprising or consisting essentially of or consisting of an amino acid or amino acids localized to an amino acid sequence selected from the group consisting of SEQ ID NOs: 12, 13, 14, 15, 16, and 95 with a $K_D$ less than about 75 nM, less than about 50 nM, less than about 25 nM, or less than about 10 nM as determined by SPR, preferably, at 25° C. for Mabs and 37° C. for Fabs and have an $IC_{50}$ between about 250 nM and about 25 nM, preferably between 100 nM and about 25 nM, or more preferably between 50 nM and about 25 nM in an in vivo assay of hepcidin-25 bioactivity and are further characterized by having an $IC_{50}$ between about 100 nM and about 1 nM, preferably, between about 75 nM and about 1 nM, more preferably, between about 50 nM and about 1 nM, even more preferably, between about 25 nM and about 1 nM in an in vitro assay of hepcidin-25 bioactivity. Preferably, the in vivo assay measures an IL-6-induced decrease in serum iron levels. Preferably, the in vitro assay of hepcidin-25 bioactivity assay measures hepcidin-induced internalization and/or degradation of ferroportin 1. Even more preferably, the anti-FPN1 Mabs, or antigen-binding fragments thereof, do not bind one or more peptides selected from the group consisting of SEQ ID NOS: 98, 183-214.

In particular embodiments, the anti-FPN1 Mabs, or antigen-binding fragments thereof, of the present invention comprise a LCDR1, LCDR2, LCDR3, HCDR1, HCDR2, and HCDR3 comprising the amino acid sequence shown in SEQ ID NOs: 37, 129, 22, 107, 118, and 120, respectively, and bind human FPN1 consisting of the amino acid sequence shown in SEQ ID NO:1 at an epitope comprising or consisting essentially of or consisting of an amino acid or amino acids localized to an amino acid sequence selected from the group consisting of SEQ ID NOs: 12, 13, 14, 15, 16, and 95 with a $K_D$ between about 100 nM to about 0.5 nM, preferably, between about 100 nM to about 1 nM, more preferably, between about 75 nM to about 5 nM, even more preferably, between about 50 nM to about 10 nM, even more preferably, between about 15 nM to about 10 nM, even more preferably, between about 10 nM to about 0.5 nM, even more preferably, between about 5 nM to about 0.5 nM, even more preferably, between about 5 nM to about 0.7 nM, even more preferably, between about 3 nM to about 0.7 nM, or most preferably, from about 3 nM to about 1 nM, as determined by SPR, preferably, at 25° C. for Mabs and 37° C. for Fabs and have an $IC_{50}$ between about 250 nM and about 25 nM, preferably, between 100 nM and about 25 nM, or more preferably, between 50 nM and about 25 nM in an in vivo assay of hepcidin-25 bioactivity and are further characterized by having an $IC_{50}$ between about 100 nM and about 1 nM, preferably, between about 75 nM and about 1 nM, more preferably, between about 50 nM and about 1 nM, even more preferably, between about 25 nM and about 1 nM, more preferably, between about 50 nM and about 1 nM, even more preferably, between about 25 nM and about 1 nM in an in vitro assay of hepcidin-25 bioactivity. Preferably, the in vivo assay measures an IL-6-induced decrease in serum iron levels. Preferably, the in vitro assay of hepcidin-25 bioactivity assay measures hepcidin-induced internalization and/or degradation of ferroportin 1. Even more preferably, the anti-FPN1 Mabs, or antigen-binding fragments thereof, do not bind one or more peptides selected from the group consisting of SEQ ID NOS: 98, 183-214.

In particular embodiments, the anti-FPN1 Mabs, or antigen-binding fragments thereof, of the present invention comprise a LCDR1, LCDR2, LCDR3, HCDR1, HCDR2, and HCDR3 comprising the amino acid sequence shown in SEQ ID NOs: 37, 129, 22, 107, 118, and 120, respectively, and bind human FPN1 consisting of the amino acid sequence shown in SEQ ID NO: 1 at an epitope comprising or consisting essentially of or consisting of an amino acid or amino acids localized to an amino acid sequence selected from the group consisting of SEQ ID NOs: 12, 13, 14, 15, 16, and 95 and 1) a $K_D$ between about 100 nM to about 0.5 nM, preferably, between about 100 nM to about 1 nM, more preferably, between about 75 nM to about 5 nM, even more preferably, between about 50 nM to about 10 nM, even more preferably, between about 15 nM to about 10 nM, even more preferably, between about 10 nM to about 0.5 nM, even more preferably, between about 5 nM to about 0.5 nM, even more preferably, between about 5 nM to about 0.7 nM, even more preferably, between about 3 nM to about 0.7 nM, or most preferably, from about 3 nM to about 1 nM, as determined by SPR, preferably, at 25° C. for Mabs and 37° C. for Fabs, 2) an $IC_{50}$ between about 250 nM and about 25 nM, preferably between 100 nM and about 25 nM, or more preferably between 50 nM and about 25 nM in an in vivo assay of hepcidin-25 bioactivity, 3) an $IC_{50}$ between about 100 nM and about 1 nM, preferably, between about 75 nM and about 1 nM, more preferably, between about 50 nM and about 1 nM, even more preferably, between about 25 nM and about 1 nM in an in vitro assay of hepcidin-25 bioactivity, and 4) a dissociation rate ($k_{off}$) for human ferroportin 1 between about $7.5 \times 10^{-3}$ s$^{-1}$ and about $1 \times 10^{-4}$ s$^{-1}$, preferably between about $2.5 \times 10^{-3}$ s$^{-1}$ and about $1 \times 10^{-4}$ s$^{-1}$, more preferably between about $1 \times 10^{-3}$ s$^{-1}$ and about $1 \times 10^{-4}$ s$^{-1}$, and even more preferably between about $5 \times 10^{-4}$ s$^{-1}$ and about $1 \times 10^{-4}$ s$^{-1}$, as determined by SPR, preferably, at 25° C. for Mabs and 37° C. for Fabs. Preferably, the in vivo assay measures an IL-6-induced decrease in serum iron levels. Preferably, the in vitro assay of hepcidin-25 bioactivity assay measures hepcidin-induced internalization and/or degradation of ferroportin 1. Even more preferably, the anti-FPN1 Mabs, or antigen-binding fragments thereof, do not bind one or more peptides selected from the group consisting of SEQ ID NOS: 98, 183-214.

In particular embodiments, the anti-FPN1 Mabs, or antigen-binding fragments thereof, of the present invention comprise a LCDR1, LCDR2, LCDR3, HCDR1, HCDR2, and HCDR3 comprising the amino acid sequences shown in SEQ ID NOs: 37, 125, 22, 23, 110, and 19, respectively, and bind human FPN1 consisting of the amino acid sequence shown in SEQ ID NO: 1 at an epitope comprising or consisting essentially of or consisting of an amino acid or amino acids localized to an amino acid sequence selected from the group consisting of SEQ ID NOs: 12, 13, 14, 15, 16, and 95 and are characterized by having a $K_D$ between about 100 nM to about 0.5 nM, preferably, between about 100 nM to about 1 nM, more preferably, between about 75 nM to about 5 nM, even more preferably, between about 50 nM to about 10 nM, even more preferably, between about 15 nM to about 10 nM, even more preferably, between about 10 nM to about 0.5 nM, even more preferably, between about 5 nM to about 0.5 nM, even more preferably, between about 5 nM to about 0.7 nM, even more preferably, between about 3 nM to about 0.7 nM, or most preferably, from about 3 nM to about 1 nM, as determined by SPR, preferably, at 25° C. for Mabs and 37° C. for Fabs, 2) an $IC_{50}$ between about 250 nM and about 25 nM, preferably between 100 nM and about 25 nM, or more preferably between 50 nM and about 25 nM in an in vivo assay of hepcidin-25 bioactivity, 3) an $IC_{50}$ between about 100 nM and about 1 nM, preferably, between about 75 nM and about 1 nM, more preferably, between about 50 nM and about 1 nM, even more preferably, between about 25 nM and about 1 nM in an in vitro assay of hepcidin-25 bioactivity, and 4) a dissociation rate ($k_{off}$) for human ferroportin 1 between about $7.5 \times 10^{-3}$ $s^{-1}$ and about $1 \times 10^{-4}$ $s^{-1}$, preferably between about $2.5 \times 10^{-3}$ $s^{-1}$ and about $1 \times 10^{-4}$ $s^{-1}$, more preferably between about $1 \times 10^{-3}$ $s^{-1}$ and about $1 \times 10^{-4}$ $s^{-1}$, and even more preferably between about $5 \times 10^{-4}$ $s^{-1}$ and about $1 \times 10^{-4}$ $s^{-1}$, as determined by SPR, preferably, at 25° C. for Mabs and 37° C. for Fabs. Preferably, the in vivo assay measures an IL-6-induced decrease in serum iron levels. Preferably, the in vitro assay of hepcidin-25 bioactivity assay measures hepcidin-induced internalization and/or degradation of ferroportin 1. Even more preferably, the anti-FPN1 Mabs, or antigen-binding fragments thereof, do not bind one or more peptides selected from the group consisting of SEQ ID NOS: 98, 183-214. Even more preferably, the anti-FPN1 Mabs, or antigen-binding fragments thereof, do not bind one or more peptides selected from the group consisting of SEQ ID NOS: 98, 183-214.

In particular embodiments, the anti-FPN1 Mabs, or antigen-binding fragments thereof, of the present invention comprise a LCDR1, LCDR2, LCDR3, HCDR1, HCDR2, and HCDR3 comprising the amino acid sequences shown in SEQ ID NOs: 37, 177, 22, 23, 112, and 19, respectively, and bind human FPN1 consisting of the amino acid sequence shown in SEQ ID NO: 1 at an epitope comprising or consisting essentially of or consisting of an amino acid or amino acids localized to an amino acid sequence selected from the group consisting of SEQ ID NOs: 12, 13, 14, 15, 16, and 95 and are characterized by having 1) a $K_D$ between about 100 nM to about 0.5 nM, preferably, between about 100 nM to about 1 nM, more preferably, between about 75 nM to about 5 nM, even more preferably, between about 50 nM to about 10 nM, even more preferably, between about 15 nM to about 10 nM, even more preferably, between about 10 nM to about 0.5 nM, even more preferably, between about 5 nM to about 0.5 nM, even more preferably, between about 5 nM to about 0.7 nM, even more preferably, between about 3 nM to about 0.7 nM, or most preferably, from about 3 nM to about 1 nM, as determined by SPR, preferably, at 25° C. for Mabs and 37° C. for Fabs, 2) an $IC_{50}$ between about 250 nM and about 25 nM, preferably between 100 nM and about 25 nM, or more preferably between 50 nM and about 25 nM in an in vivo assay of hepcidin-25 bioactivity, 3) an $IC_{50}$ between about 100 nM and about 1 nM, preferably, between about 75 nM and about 1 nM, more preferably, between about 50 nM and about 1 nM, even more preferably, between about 25 nM and about 1 nM in an in vitro assay of hepcidin-25 bioactivity, and 4) a dissociation rate ($k_{off}$) for human ferroportin 1 between about $7.5 \times 10^{-3}$ $s^{-1}$ and about $1 \times 10^{-4}$ $s^{-1}$, preferably between about $2.5 \times 10^{-3}$ $s^{-1}$ and about $1 \times 10^{-4}$ $s^{-1}$, more preferably between about $1 \times 10^{-3}$ $s^{-1}$ and about $1 \times 10^{-4}$ $s^{-1}$, and even more preferably between about $5 \times 10^{-4}$ $s^{-1}$ and about $1 \times 10^{-4}$ $s^{-1}$, as determined by SPR, preferably, at 25° C. for Mabs and 37° C. for Fabs. Preferably, the in vivo assay measures an IL-6-induced decrease in serum iron levels. Preferably, the in vitro assay of hepcidin-25 bioactivity assay measures hepcidin-induced internalization and/or degradation of ferroportin 1. Even more preferably, the anti-FPN1 Mabs, or antigen-binding fragments thereof, do not bind one or more peptides selected from the group consisting of SEQ ID NOS: 98, 183-214.

In particular embodiments, the anti-FPN1 Mabs, or antigen-binding fragments thereof, of the present invention comprise a LCDR1, LCDR2, LCDR3, HCDR1, HCDR2, and HCDR3 comprising the amino acid sequences shown in SEQ ID NOs: 37, 122, 22, 23, 110, and 19, respectively, and bind human FPN1 consisting of the amino acid sequence shown in SEQ ID NO: 1 at an epitope comprising or consisting essentially of or consisting of an amino acid or amino acids localized to an amino acid sequence selected from the group consisting of SEQ ID NOs: 12, 13, 14, 15, 16, and 95 and are characterized by having 1) a $K_D$ between about 100 nM to about 0.5 nM, preferably, between about 100 nM to about 1 nM, more preferably, between about 75 nM to about 5 nM, even more preferably, between about 50 nM to about 10 nM, even more preferably, between about 15 nM to about 10 nM, even more preferably, between about 10 nM to about 0.5 nM, even more preferably, between about 5 nM to about 0.5 nM, even more preferably, between about 5 nM to about 0.7 nM, even more preferably, between about 3 nM to about 0.7 nM, or most preferably, from about 3 nM to about 1 nM, as determined by SPR, preferably, at 25° C. for Mabs and 37° C. for Fabs, 2) an $IC_{50}$ between about 250 nM and about 25 nM, preferably between 100 nM and about 25 nM, or more preferably between 50 nM and about 25 nM in an in vivo assay of hepcidin-25 bioactivity, 3) an $IC_{50}$ between about 100 nM and about 1 nM, preferably, between about 75 nM and about 1 nM, more preferably, between about 50 nM and about 1 nM, even more preferably, between about 25 nM and about 1 nM in an in vitro assay of hepcidin-25 bioactivity, and 4) a dissociation rate ($k_{off}$) for human ferroportin 1 between about $7.5 \times 10^{-3}$ $s^{-1}$ and about $1 \times 10^{-4}$ $s^{-1}$, preferably between about $2.5 \times 10^{-3}$ $s^{-1}$ and about $1 \times 10^{-4}$ $s^{-1}$, more preferably between about $1 \times 10^{-3}$ $s^{-1}$ and about $1 \times 10^{-4}$ $s^{-1}$, and even more preferably between about $1 \times 10^{-4}$ $s^{-1}$ and about $1 \times 10^{-4}$ $s^{-1}$, as determined by SPR, preferably, at 25° C. for Mabs and 37° C. for Fabs. Preferably, the in vivo assay measures an IL-6-induced decrease in serum iron levels. Preferably, the in vitro assay of hepcidin-25 bioactivity assay measures hepcidin-induced internalization and/or degradation of ferroportin 1. Even more preferably, the anti-FPN1 Mabs, or antigen-binding fragments thereof, do not bind one or more peptides selected from the group consisting of SEQ ID NOS: 98, 183-214.

In particular embodiments, the anti-FPN1 Mabs, or antigen-binding fragments thereof, of the present invention comprise:
  a. a light chain and a heavy chain as shown in SEQ ID NO: 154 and SEQ ID NO: 152, respectively;
  b. a light chain and a heavy chain as shown in SEQ ID NO: 181 and SEQ ID NO: 179, respectively; or
  c. a light chain and a heavy chain as shown in SEQ ID NO: 158 and SEQ ID NO: 156, respectively,
and bind human FPN1 consisting of the amino acid sequence shown in SEQ ID NO: 1 at an epitope comprising or consisting essentially of or consisting of an amino acid or amino acids localized to an amino acid sequence selected from the group consisting of SEQ ID NOs: 12, 13, 14, 15, 16, and 95 and are characterized by having 1) a $K_D$ between about 100 nM to about 0.5 nM, preferably, between about 100 nM to about 1 nM, more preferably, between about 75 nM to about 5 nM, even more preferably, between about 50 nM to about 10 nM, even more preferably, between about 15 nM to about 10 nM, even more preferably, between about 10 nM to about 0.5 nM, even more preferably, between about 5 nM to about 0.5 nM, even more preferably, between about 5 nM to about 0.7 nM, even more preferably, between about 3 nM to about 0.7 nM, or most preferably, from about 3 nM to about 1 nM, as determined by SPR, preferably, at 25° C. for Mabs and 37° C. for Fabs, 2) an $IC_{50}$ between about 250 nM and about 25 nM, preferably between 100 nM and about 25 nM, or more preferably between 50 nM and about 25 nM in an in vivo assay of hepcidin-25 bioactivity, 3) an $IC_{50}$ between about 100 nM and about 1 nM, preferably, between about 75 nM and about 1 nM, more preferably, between about 50 nM and about 1 nM, even more preferably, between about 25 nM and about 1 nM in an in vitro assay of hepcidin-25 bioactivity, and 4) a dissociation rate ($k_{off}$) for human ferroportin 1 between about $7.5 \times 10^{-3}$ $s^{-1}$ and about $1 \times 10^{-4}$ $s^{-1}$, preferably between about $2.5 \times 10^{-3}$ $s^{-1}$ and about $1 \times 10^{-4}$ $s^{-1}$, more preferably between about $1 \times 10^{-3}$ $s^{-1}$ and about $1 \times 10^{-4}$ $s^{-1}$, and even more preferably between about $5 \times 10^{-4}$ $s^{-1}$ and about $1 \times 10^{-4}$ $s^{-1}$, as determined by SPR, preferably, at 25° C. for Mabs and 37° C. for Fabs. Preferably, the in vivo assay measures an IL-6-induced decrease in serum iron levels. Preferably, the in vitro assay of hepcidin-25 bioactivity assay measures hepcidin-induced internalization and/or degradation of ferroportin 1.

The term "treating" (or "treat" or "treatment") refers to slowing, interrupting, arresting, controlling, stopping, reducing, or reversing the progression or severity of a symptom, disorder, condition, or disease, but does not necessarily involve a total elimination of all disease-related symptoms, conditions, or disorders.

The term "preventing" (or "prevent" or "prevention") means prohibiting, restraining, or inhibiting the incidence or occurrence of a symptom, disorder, condition, or disease. Acute events and chronic conditions may be treated and prevented. In an acute event, an antibody or antigen-binding fragment thereof is administered at the onset of a symptom, disorder, condition, or disease, and is discontinued when the acute event ends. In contrast, a chronic symptom, disorder, condition, or disease is treated over a more protracted time frame.

A "disorder" is any condition that would benefit from treatment according to the present invention. The terms "disorder", "condition" and "disease" are used interchangeably herein and include chronic and acute mature hepcidin-promoted disorders, including, but not limited to, anemia including, but not limited to, anemia of chronic disease.

The term "anemia of chronic disease" refers to any anemia that develops as a result of, for example, extended infection, inflammation, and neoplastic disorders. The anemia which develops is often characterized by a shortened red blood cell life span and sequestration of iron in macrophages, which results in a decrease in the amount of iron available to make new red blood cells. Conditions associated with anemia of chronic disease include, but are not limited to, chronic bacterial endocarditis, osteomyelitis, rheumatic fever, ulcerative colitis, and neoplastic disorders. Further conditions include other diseases and disorders associated with infection, inflammation, and neoplasms, including, for example, inflammatory infections (e.g., pulmonary abscess, tuberculosis), inflammatory noninfectious disorders (e.g., rheumatoid arthritis, systemic lupus erythrematosus, Crohn's disease, hepatitis, inflammatory bowel disease), and various cancers, tumors, and malignancies (e.g., carcinoma, sarcoma, lymphoma). Anemia of chronic disease is associated with hypoferremia and reticuloendothelial cell iron sequestration.

Inflammatory cytokines are potent inducers of hepcidin expression, and hepcidin excess may play a key role in the pathogenesis of anemia in these patients (Weiss, et al., N. Engl. J. Med., 352:1011-1023 (2005); Pigeon. et al., J. Biol. Chem. 276:7811-7819 (2001); Nicolas, et al., J. Clin. Invest. 110:1037-1044 (2002); Nemeth, et al., J. Clin. Invest. 113: 1271-1276 (2004); Nemeth, et al., Blood, 101:2461-2463 (2003); Lee, et al., Proc. Natl. Acad. Sci. USA., 102:1906-1910 (2005)). Inflammatory mediators such as IL-6 may regulate hepcidin expression through STAT3 (Wrighting, et al., Blood, 108:3204-3209 (2006); Verga Falzacappa, et al., Blood, 109:353-358 (2007); Pietrangelo et al., Gastroenterology, 132:294-300 (2007)). The data presented herein provide in vivo evidence that anti-FPN1 Mabs of the present invention increase serum iron levels.

Also provided by the present invention are methods of treating anemia comprising the administration of anti-FPN1 Mabs, or antigen-binding fragments thereof, of the present invention. In some embodiments, the method of treating anemia comprises the step of administering a pharmaceutical composition comprising an anti-FPN1 Mab, or antigen-binding fragment thereof, to a subject at risk for or exhibiting pathologies as described herein, e.g., anemia disorders, using standard administration techniques.

The phrase "effective amount" as used herein refers to an amount necessary (at dosages and for periods of time and for the means of administration) to achieve the desired therapeutic result. An effective amount of the antibody may vary according to factors such as the disease state, age, gender, and weight of the individual, and the ability of the antibody or antibody portion to elicit a desired response in the individual. An effective amount is also one in which any toxic or detrimental effect of the antibody, are outweighed by the therapeutically beneficial effects.

An effective amount is at least the minimal amount, but less than a toxic amount, of an active agent which is necessary to impart therapeutic benefit to a subject. Stated another way, an effective amount or therapeutically effective amount of an antibody of the invention is an amount which, in mammals, preferably humans, (i) increases serum iron levels, reticulocyte count, red blood cell count, hemoglobin, and/or hematocrit, or (ii) treats a disorder wherein the presence of mature hepcidin causes or contributes to an undesirable pathological effect, or (iii) decreases mature hepcidin bioactivity resulting in a beneficial therapeutic effect in a mammal, preferably a human, including, but not limited to, having anemia including, but not limited to, anemia of chronic disease, including, but not limited to, anemia resulting from infection, inflammation, and/or cancer. An effective amount of an antibody of the invention may be administered in a single dose or in multiple doses. Furthermore, an effective amount of an antibody of the invention may be administered in multiple doses of amounts that would be less than an effective amount if not administered more than once.

As is well known in the medical arts, dosages for any one subject depends upon many factors, including the patient's size, body surface area, age, the particular compound to be administered, gender, time and route of administration, general health, and other drugs being administered concurrently. Dose may further vary depending on the type and severity of the disease. A typical dose can be, for example, in the range of about 1 mg to about 100 mg; preferably, about 2 mg to about 100 mg; more preferably, about 5 mg to about 100 mg; even more preferably, about 5 mg to about 50 mg, even more preferably, about 5 mg to about 25 mg; even more preferably, about 5 mg to about 20 mg; even more preferably, about 5 mg to about 15 mg; however, doses below or above this exemplary range are envisioned, especially considering the aforementioned factors. A daily parenteral dosage regimen can be from about 10 µg/kg to about 100 mg/kg, preferably, from about 100 µg/kg to about 100 mg/kg, more preferably, from about 1 mg/kg to about 100 mg/kg, even more preferably, from about 1 mg/kg to about 30 mg/kg, even more preferably, from about 3 mg/kg to about 30 mg/kg, or most preferably from about 3 mg/kg to about 30 mg/kg. Progress may be monitored by periodic assessment, and the dose adjusted accordingly.

These suggested amounts of anti-FPN1 antibody are subject to a great deal of therapeutic discretion. The key factor in selecting an appropriate dose and scheduling is the result obtained. Factors for consideration in this context include the particular disorder being treated, the clinical condition of the individual patient, the cause of the disorder, the site of delivery of the antibody, the particular type of antibody, the method of administration, the scheduling of administration, and other factors known to medical practitioners.

The antibodies of the present invention can be used as medicaments in human medicine, administered by a variety of routes. Most preferably, such compositions are for parenteral administration. Such pharmaceutical compositions can be prepared by methods well known in the art. See, e.g., *Remington: The Science and Practice of Pharmacy, 19th* ed. (1995), Gennaro, A., et al., Mack Publishing Co. Accordingly, this invention also provides pharmaceutical compositions comprising one or more antibodies of the invention in combination with one or more pharmaceutically acceptable carriers, diluents, or excipients. In a particular embodiment, the pharmaceutical composition further comprises one or more other therapeutic agents.

The term parenteral as used herein includes intravenous, intramuscular, subcutaneous, rectal, vaginal, or intraperitoneal administration. Parenteral delivery by intravenous infusion or intravenous, intraperitoneal, or subcutaneous injection is preferred. Subcutaneous injection is most preferred. Suitable vehicles for such injections are well known in the art.

The pharmaceutical composition typically must be sterile and stable under the conditions of manufacture and storage in the container provided, including e.g., a sealed vial, syringe or other delivery device, e.g., a pen. Therefore, pharmaceutical compositions may be sterile filtered after making the formulation, or otherwise made microbiologically acceptable.

An antibody of the invention can be incorporated into a pharmaceutical composition suitable for administration to a human subject. An antibody of the invention may be administered to a human subject alone or in combination with a pharmaceutically acceptable carrier and/or diluent in single or multiple doses. Such pharmaceutical compositions are designed to be appropriate for the selected mode of administration, and pharmaceutically acceptable diluents, carrier, and/or excipients such as dispersing agents, buffers, surfactants, preservatives, solubilizing agents, isotonicity agents including but not limited to sodium chloride, stabilizing agents and the like are used as appropriate. Said compositions can be designed in accordance with conventional techniques disclosed in, for example, *Remington, The Science and Practice of Pharmacy, 19th* Edition, Gennaro, Ed., Mack Publishing Co., Easton, Pa. (1995) which provides a compendium of formulation techniques as are generally known to practitioners. Suitable carriers for pharmaceutical compositions include any material which, when combined with an antibody of the invention, retains the molecule's activity and is non-reactive with the subject's immune system.

The terms "subject" and "patient" used interchangeably herein, refer to a mammal, preferably, a human. In certain embodiments, the patient has a disorder that would benefit from a decreased level of mature hepcidin, a decrease in mature hepcidin bioactivity, and/or an increase in serum iron level, reticulocyte count, red blood cell count, hemoglobin, and/or hematocrit.

Administration of a FPN1 antibody compound alone may be useful in patients intolerant to one or more ESAs, either at any dose or only at high doses, due to, for example, undesirable side effects. A FPN1 Mab, or antigen-binding fragment thereof, of the present invention administered alone or in combination with an ESA, may also be useful in ESA-resistant patients who are incapable of reaching their hematocrit goals with ESAs alone, either at conventional or high doses.

A FPN1 Mab, or antigen-binding fragment thereof, of the present invention may also be administered when combination drug therapy, including the use of ESAs, is inadequate in allowing patients to reach their hematocrit goals.

In another embodiment, the present invention provides the use of a monoclonal antibody or an antigen-binding fragment thereof, of the present invention for the manufacture of a medicament for increasing serum iron levels, reticulocyte count, red blood cell count, hemoglobin, and/or hematocrit in a human.

In another embodiment, the present invention provides the use of the monoclonal antibody or an antigen-binding fragment thereof in the manufacture of a medicament for use in combination therapy for increasing serum iron levels, reticulocyte count, red blood cell count, hemoglobin, and/or hematocrit in a human, wherein said medicament is to be administered in combination with one or more ESAs selected from the group consisting of epoetin alfa, epoietin beta, darbepoetin alfa, hematide, methoxy polyethylene glycol-epoetin beta, or other therapeutic agent or therapeutic treatment conventionally employed to increase serum iron levels, reticulocyte count, red blood cell count, hemoglobin, and/or hematocrit in a human.

The following non-limiting examples illustrate various properties of the anti-FPN1 antibodies disclosed herein.

EXAMPLE 1

Production of Human Hepcidin-25

Human hepcidin-25 can be obtained from commercial sources (e.g., Peptide International (Louisville, Ky.)) or produced by a variety of synthetic or recombinant techniques known in the art. Alternatively, a fusion protein comprising the twenty-five amino acids of human hepcidin-25 sequence and having the amino acid sequence as shown in SEQ ID NO: 91 is expressed in *E. coli*. Inclusion bodies are isolated from 3 liters of *E. coli* expressing the human hepcidin fusion protein after a 3-6 hour induction with 1 mM IPTG at 37° C. The inclusion bodies are solubilized in buffer A (50 mM Tris and 8 M urea (pH 8.0)). The supernatant is passed over an IMAC column (20 mL resin). The column is washed with buffer A until the absorbance returned to baseline and the bound polypeptides are batch eluted from the column by 0.5 M imidazole in buffer A. The human hepcidin-25 fusion protein is pooled and reduced with 50 mM DTT. This fusion protein is then refolded by diluting pooled material into 2 M urea, 3 mM cysteine, 50 mM Tris (pH 8.0) to a final protein concentration less than 50 µg/mL. This material is stirred at room temperature and air oxidized for 48 hours. The oxidized polypeptides are passed over an IMAC column (20 mL) at a flow rate of 5 mL/min, and the human hepcidin-25 fusion protein is batch eluted from the column by 0.5 M imidazol in buffer A. The pooled fractions containing the human hepcidin-25 fusion protein are concentrated and passed over a Superdex 75 (GE Healthcare, XK26/60) sizing column equilibrated with 50 mM Tris, 4 M urea, pH 8.0, at a flow rate of 3 mL/min. The monomeric fusion protein is pooled and then diluted to 50 mM Tris, 2M urea, 5 mM $CaCl_2$, pH 8.0 and then is cleaved with enterokinase to produce human hepcidin-25 of SEQ ID NO: 1. Uncleaved human hepcidin-25 fusion protein is removed by passive IMAC chromatography (as outlined above). The flow through from the IMAC column is then passed over a C-18 Reversed Phase column at a flow rate of 4.0 mL/minute. The column is washed with 0.1% TFA in water until the absorbance returned to baseline and the bound polypeptides are eluted from the column with a linear gradient of acetonitrile from 20% to 40% with 0.1% TFA at a rate of 0.5%/min. Fractions which contain the human hepcidin-25 polypeptide are pooled and analyzed by N-terminal amino acid sequencing and matrix assisted laser desorption/ionization mass spectrometry (MALDI-MS). Polypeptides encoding rat, mouse, and Cynomolgus monkey hepcidin-25 and various N-terminally truncated forms of human hepcidin-25, including hepcidin-22 and hepcidin-20 were obtained commercially (e.g., Peptide International).

EXAMPLE 2

Generation of 34A9 Fab

Anti-FPN1 antibodies may be obtained by immunizing mice with an immunogenic peptide having the amino acid sequence as shown in SEQ ID NO: 11. More specifically, an immunogenic peptide comprising an OVA epitope linked by a peptide linker to the amino acid sequence shown in SEQ ID NO: 12, which is thought to be at least part of an extracellular loop of human FPN1, may be used to immunize mice. After immunization, mice spleens are harvested and spleen cells are sorted by Magnetic Activated Cell Sorting using a biotinylated peptide having the amino acid sequence shown in SEQ ID NO: 12 and streptavidin beads. RNA is isolated from antigen binding cells and converted into cDNA using oligo dT. Antibody heavy and light chain variable regions are obtained by PCR using antibody framework primers and cloned into a phage vector to make a Fab antibody library. The phage antibody library is screened with a biotinylated peptide, e.g., 100 nM, having the amino acid sequence shown in SEQ ID NO: 12. Positively binding clones are then characterized by DNA sequencing, Fabs expression and binding to the immunizing peptide and/or cells expressing human ferroportin. Fab 34A9 was identified following the procedure essentially as described above.

EXAMPLE 3

Epitope Mapping of Anti-FPN1 Mabs

Peptides containing partial sequences of the FPN1 related immunogen may be used in dot blot hybridization experiments to determine the epitopes of the mouse Mab 34A9. The following peptides may be synthesized and dissolved in water (underlined amino acids denote actual FPN1 amino acid sequence):

```
FpnE3a
(SEQ ID NO: 96):      GGSPFEDIRSRFIQGESITPTKGC 060719Z
(SEQ ID NO: 97):      GGSPFEDIRSRFIQGC 060719Y
(SEQ ID NO: 98):      GGIQGESITPTKIPEITTEGC

0708L4A
(SEQ ID NO: 99):      GGMPGSPLDLSVSPFEDGC

0708L4B
(SEQ ID NO: 100):     GGSPLDLSVSPFEDIRSGC

0708L4C
(SEQ ID NO: 101):     GGEDIRSRFIQGESITGC

0708L4D
(SEQ ID NO: 102):     GGRSRFIQGESITPTKGC
```

For each peptide, 3 μl of 1-5 μg/mL peptide is spotted onto a piece of nitrocellulose membrane and air dried. The membrane is blocked with blocking buffer (e.g., PBS containing 1% BSA), then incubated with 3-5 μg/mL FPN1 antibody in blocking buffer at room temperature for an hour. The membrane is washed three times, 5 min each, with 1×PBST (10 mM sodium phosphate, 150 mM NaCl, 0.1% Tween-20, pH 7.4) before it is incubated with IR700-labeled-Goat-anti-Mouse antibody according to manufacturer's protocol (Li-Cor, Inc; Lincoln, Nebr.). The membrane is washed three times, five minutes each, with 1×PBST, is imaged on Odyssey imaging system and Odyssey software (LiCor, Inc).

FIG. 1 indicates that Mab 34A9 binds to peptides FpnE3a, 060719Z, 0708L4C, and 0708L4D, all of which contain amino acids 409 to 415 of SEQ ID NO: 1. Mab 34A9 does not require the amino acids sequence of EDI as indicated by the binding to peptide 0708L4D. Mab 34A9 binds more weakly to peptide 060719Z than 0708L4C; the latter peptide contains amino acids 416-419 of FPN1 (SEQ ID NO: 1).

EXAMPLE 4

Affinities of Anti-FPN1 Fabs and Mabs as Determined by SPR

The affinities of FPN1 binding Fabs and Mabs may be determined on Biacore T100 and using 1:1 binding model in the Biacore T100 evaluation software (BIAcore® AB, Upsala, Sweden). Briefly, the T-REx system, a commercially available tetracycline-regulated expression system without viral transactivators (Invitrogen, Carlsbad, Calif.) is used for stable cell line generation in T-Rex HEK 293 cells. All growth conditions are described in the T-REx manual provided by Invitrogen. FPN1 is C-terminally fused with GFP. Expression of FPN1-GFP is induced by 1-10 ng/mL doxycycline for 1-24 hours. Induced cells are harvested by scraping off from flasks and then washed with 1×PBS. Cell pellets can be stored at −80° C. before use. About five million induced cells are resuspended in 10 mM phosphate buffer with 0.2% Tween-20 and protease inhibitors, e.g., Complete™ Protease Inhibitor Cocktail Tablet (Roche Diagnostics Corp., Indianapolis, Ind.). Three cycles of freeze/thaw/sonication are used to lyse the cells. The lysate is diluted two-fold with Biacore running buffer and centrifuged to remove debris.

On Biacore T100, rabbit anti-GFP antibody or goat anti-GFP antibody is immobilized onto flow cell 1 to 4 of a CM5 chip at 5000-15000 Rus. FPN1-GFP is captured onto flow cell 2, 3, or 4 from the lysate of induced cells. Flow cell 1 is used as reference. Then all flow cells are injected with different concentrations of antibodies to evaluate the binding and kinetics. Surface plasmon resonance based measurements using univalent antigen-binding fragments such as Fabs are generally preferred to those using multivalent antibodies in this assay format to minimize avidity effects. Tables 4a and 4b show the binding characteristics for anti-human FPN1 binding Fabs using rabbit anti-GFP antibody (Invitrogen, Carlsbad, Calif. (catalog #A11122)) and goat anti-GFP antibody (R&D Systems, Minneapolis, Minn. (catalog #AF4240)), respectively.

TABLE 4(a)

Binding Kinetics of Fabs from FPN1 Antibodies to Human FPN1 (Determined by Biacore T100 at 37° C.)

| Fab | Kon ($M^{-1}s^{-1}$) | Koff ($s^{-1}$) | Kinetic $K_D$ (M) |
|---|---|---|---|
| 34A9 | 6.321E+04 | 2.620E−03 | 4.145E−08 |
| 1G9 | 1.269E+05 | 8.974E−04 | 7.707E−09 |
| 3D8 | 1.920E+05 | 2.000E−03 | 1.042E−08 |

As shown in Table 4(a), the $K_D$ for human FPN1 of the mouse Fab 34A9 is approximately 41 nM as determined by SPR at 37° C. in this assay format. The $K_D$ for human FPN1 of the mouse Fab 1G9, an affinity matured form of the mouse Fab 34A9 is about 7.7 nM as determined by SPR at 37° C., an improvement in binding affinity of approximately 5-fold. Fab 3D8, a humanized form of the mouse Fab 1G9 having the human heavy chain framework VH1-69 and light chain framework O2, demonstrated a $K_D$ for human FPN1 of about 10 nM as determined by SPR at 37° C. in this assay format.

TABLE 4(b)

Binding Kinetics of Fabs from FPN1 Antibodies to Human FPN1
(Determined by Biacore T100 at 37° C.)

| Fab | (n) | Kon ($M^{-1}s^{-1}$) | Koff ($s^{-1}$) | Kinetic $K_D$ (M) |
|---|---|---|---|---|
| mouse 1G9 | 4 | 1.726E+05 | 4.968E-04 | 2.900E-09 |
| human 3D8 | 3 | 3.284E+05 | 2.061E-03 | 6.293E-09 |
| human 4A10-3 | 4 | 8.443E+05 | 1.483E-03 | 1.761E-09 |
| human Combi11 | 3 | 2.309E+06 | 6.369E-03 | 2.395E-09 |
| human L2.2-4 | 3 | 4.308E+05 | 7.905E-04 | 1.959E-09 |

As shown in Table 4(b), the $K_D$ for human FPN1 of the mouse Fab 1G9, an affinity matured form of the mouse Fab 34A9 is about 2.9 nM as determined by SPR at 37° C. in this assay format. Fab 3D8, a humanized form of the mouse Fab 1G9 having the human heavy chain framework VH1-69 and light chain framework O2, demonstrated a $K_D$ for human FPN1 of about 6.3 nM as determined by SPR at 37° C. in this assay format. Affinity matured Fabs 4A10-3, Combi11, and L2.2-4 demonstrated a $K_D$ for human FPN1 between about 2.4 nM to about 1.8 nM as determined by SPR at 37° C. in this assay format.

Table 5 shows the binding characteristics for anti-human FPN1 binding Mabs using rabbit anti-GFP antibody (Invitrogen, Carlsbad, Calif. (catalog #A11122)).

TABLE 5

Binding Kinetics of MAbs to Human FPN1
(Determined by Biacore T100 at 25° C. or 37° C.)

| Mab | Temp. | Kon ($M^{-1}s^{-1}$) | Koff ($s^{-1}$) | Kinetic $K_D$ (M) |
|---|---|---|---|---|
| mouse 34A9 | 25° C. | 6.901E+04 | 8.155E-05 | 1.182E-09 |
| mouse 1G9 | 25° C. | 1.348E+05 | 9.813E-05 | 7.281E-10 |
| human 3D8 | 37° C. | 3.252E+05 | 1.095E-03 | 3.366E-09 |

The $K_D$ for human FPN1 of the mouse 34A9 Mab is approximately 1.1 nM as determined by SPR at 25° C. The $K_D$ for human FPN1 of the mouse 1G9 Mab, an affinity matured form of the mouse 34A9 Mab is about 0.73 nM as determined by SPR at 25° C. A humanized form of the mouse 1G9 Mab, 3D8 Mab, having the human heavy and light chain frameworks, VH1-69 and O2, respectively, demonstrated a $K_D$ for human FPN1 of about 3.4 nM as determined by SPR at 37° C.

The $K_D$ for human FPN1, determined as described in this Example, illustrates the generation of antibodies to human FPN1 which bind human FPN1 with high affinity and, more specifically, bind to an epitope of FPN1 that is present even when human FPN1 is expressed by cells and localized to the cellular membrane.

EXAMPLE 5

In Vitro Assay of the Effects of FPN1 Mabs on Cellular Ferritin Levels

Caco-2 cells, a human enterocyte cell line, endogenously expressing FPN1 may be monitored for changes in ferritin. Ferritin concentration in the Caco-2 cells may be increased by adding an exogenous iron source and the concentration may be further augmented with the addition of hepcidin which prevents iron export. Accordingly, the effect of anti-human FPN1 antibodies on mature hepcidin modulated iron regulation in Caco-2 cells may be determined as follows.

Caco-2 cells are removed from the cell culture vessel using trypsin (Invitrogen, Carlsbad, Calif.). The cells are collected and washed in growth medium (e.g., DMEM+10% FBS+1% non-essential amino acids+1% antibiotics/antimycotic) and collected by gentle centrifugation. Cells are resuspended in culture medium and counted. Cell concentration is adjusted to $1 \times 10^6$ cells/mL in growth medium and 2.5 µM Fe:NTA (prepared 1:4 molar ratio) is added to the cells. One hundred µl of cells are added to wells of a 96 flat well plate, followed by incubation for 24 hours at 37° C., 5% $CO_2$. Mouse $IgG_1$, a negative control, and two antibodies with different affinities to human FPN1 are prepared in growth medium at 6× the final concentration. Antibody dilutions (25 µL) or medium are added to wells in triplicate. The plates are incubated at room temperature for 15 minutes at which time 25 µL 5 µM Fe:NTA with or without 600 nM hepcidin (100 nM final concentration) are added to the appropriate wells. The cells are incubated for 24 hours 37° C., 5% $CO_2$ and then washed 3× with 200 µl Dulbecco's PBS and lysed in 50 µL radioimmunoprecipitation assay buffer (50 mM Tris, pH 7.5, 150 mM NaCl, 0.1% SDS, 1% Triton-X100®, and 0.5% sodium deoxycholate) plus protease inhibitors, e.g., Complete™ Protease Inhibitor Cocktail Tablet (Roche Diagnostics Corp., Indianapolis, Ind.), mixed and frozen at −70° C. until assayed for ferritin using an ELISA.

Briefly, microtiter plates are coated with 110 µL/well of 1 µg/mL anti-human ferritin (Leinco Technologies, St. Louis, Mo.) and incubated overnight at 4° C. The plates are washed 2 times with wash buffer (0.02 M Tris, 0.15M NaCl, 0.1% Tween 20, pH 7.4) and blocked with 150 µL of 1% casein in PBS (Thermo Fisher Scientific, Rockford, Ill.). The plates are incubated for 1 hour at room temperature. One hundred microliters (µL) of lysates and standards (human liver ferritin, Calbiochem/EMD Biosciences, La Jolla, Calif.) are added to the appropriate wells and incubated for 1 hour at room temperature. The plates are washed 3 times and bound ferritin is detected using an anti-ferritin-HRP conjugate (Leinco Technologies) at 1:2000 dilution at 100 µL per well and incubation for 1 hour at room temperature. The plates are washed 4 times and 100 µL OPD substrate (5 mg substrate tablet, dissolved in 12.5 mL of 0.1 M $Na_2HPO_4$, 0.05 M citric acid, pH 5.0 with 5 µL of 30% $H_2O_2$) is dispensed to all wells. The reaction is stopped with 100 µL 1 N HCl after 10 minutes. Absorbance at 490 nm ($A_{490}$) is read using an appropriate ELISA plate reader. The protein concentration in each sample is also measured using a BCA protein assay kit (Thermo Fisher Scientific). To account for possible well-to-well differences in cell number, ferritin concentration data are normalized to protein concentration and the effect of added antibodies is expressed as percent inhibition.

Experiments conducted as described in this Example indicate that the effects of human hepcidin-25 on ferritin concentration in the cells are inhibited by Mabs 34A9 and 1G9 (Table 6). Furthermore, the results show that the affinity of the anti-FPN1 Mab has direct implications on its functionality. More specifically, the lower affinity Mab 34A9, even at the highest concentration (200 μg/mL) only slightly inhibited mature hepcidin-induced effects (25% inhibition±0.5%), whereas the higher affinity Mab 1G9 exhibited marked inhibition in a dose-dependent matter.

TABLE 6

| Sample | Ferritin (ng)/ protein (μg) | STD | % Inhibition |
| --- | --- | --- | --- |
| NTA:Fe only | 5.11 | 0.25 | NA |
| NTA + Fe + hepcidin | 9.95 | 0.86 | NA |
| 200 μg/mL mIgG$_1$ | 9.40 | 0.25 | 11.6 |
| 100 μg/mL mIgG$_1$ | 9.78 | 0.68 | 3.5 |
| 50 μg/mL mIgG$_1$ | 10.06 | 0.96 | 0 |
| 25 μg/mL mIgG$_1$ | 9.6 | 1.29 | 7.2 |
| 12.5 μg/mL mIgG$_1$ | 10.01 | 1.11 | 0 |
| 6.25 μg/mL mIgG$_1$ | 10.45 | 2.05 | 0 |
| 200 μg/mL Mab 1G9 | 6.07 | 0.34 | 80.2 |
| 100 μg/mL Mab 1G9 | 5.68 | 0.34 | 88.2 |
| 50 μg/mL Mab 1G9 | 7.11 | 0.54 | 58.7 |
| 12.5 μg/mL Mab 1G9 | 7.93 | 0.43 | 41.7 |
| 6.25 μg/mL Mab 1G9 | 8.02 | 0.45 | 39.9 |
| 200 μg/mL Mab 34A9 | 8.74 | 0.50 | 25 |
| 50 μg/mL Mab 34A9 | 9.65 | 0.80 | 6.2 |

This data illustrates that Mabs 1G9 and 34A9 block the ability of human hepcidin-25 to induce internalization and degradation of ferroportin and hence reduce iron exported from the cells.

EXAMPLE 6

Assay for the Inhibition of Human Hepcidin-25 Binding to FPN1

Stably transfected FPN-GFP/293 cells are plated in poly-D-lysine coated plates at 60,000 cells per well in 80 μL of assay medium (DMEM 11965, 10% dialyzed FBS, 20 μM FAC, penicillin-streptomycin) and incubated 4 hours at 37° C., 10% $CO_2$. Doxycycline is added to a final concentration of 11.2 nM to induce FPN1 expression. Doxycycline induced and un-induced control cells are incubated overnight at 37° C. Next, the growth media is discarded and replaced with test antibody or an isotype control antibody in 30 μL of assay medium or 30 μL of assay medium alone control and incubated at 37° C. for 1 hour. Next, 20 μL of biotinylated mature human hepcidin is added to the wells to a final concentration of 30 nM. The samples are set aside for 1 hour, at 37° C. before washing 4 times with 200 μL 2% FBS, D-PBS (Invitrogen, Carlsbad, Calif.). Next, 65 μL of lysing buffer (0.5% Triton X-100, 10 mM EDTA) are added and the plates are shaken for 10 minutes. Next, 50 μL of the solution in each well is transferred to individual wells of a streptavidin coated plate (60 μL of 2 μg/mL streptavidin in PBS, incubated at 4° C. overnight, washed 2 times (0.1% Tween 20, TBS), blocked with casein/PBS), and then incubated for one hour at room temperature. Next, the wells of the plate are washed 3 times (0.1% Tween 20, TBS) and 50 μL anti-human hepcidin-25 Mab 3.23 at 0.5 μg/mL is added and the samples are incubated one hour at room temperature. The anti-human hepcidin-25 Mab 3.23 is described in PCT International Patent Application Publication WO 2009/058797. Next, the plates are washed three times and 50 μL anti-human IgG-horseradish peroxidase (HRP) is added at 1:2000 dilution. After incubating one hour at room temperature, 50 μL of OPD substrate is added. The reaction is stopped with 100 μL 1 N HCl after 4 minutes. Absorbance at 490 nm ($A_{490}$) is read using an appropriate ELISA plate reader.

TABLE 7

| | | % Inhibition | | | |
| --- | --- | --- | --- | --- | --- |
| | | Antibody concentration | | | |
| Antibody | | 1.2 uM | 0.3 uM | 0.75 uM | 0.019 uM |
| 1G9 | Mean | 58.1 | 55.5 | 33.7 | 17.5 |
| | SD | 1.7 | 6.7 | 20.4 | 8.7 |
| | | Antibody concentration | | | |
| | | 6.0 uM | 1.2 uM | 0.24 uM | 0.048 uM |
| 34A9 | Mean | 26.4 | 31.2 | 9.6 | −7.2 |
| | SD | 26.8 | 6.9 | 6.0 | 12.1 |
| ms IgG1 | Mean | −3.4 | 0.5 | −4.0 | −11.0 |
| | SD | 8.8 | 6.1 | 7.3 | 9.6 |

Data generated in experiments conducted essentially described in Example 6 demonstrate that Mabs 1G9 and 34A9 inhibit the ability of human hepcidin-25 to bind human FPN1.

EXAMPLE 7

Cell-based Assay for anti-FPN1 Antibody Inhibition of Hepcidin-25-induced Internalization and Degradation An in vitro cell based assay may be used to measure the mature hepcidin neutralization activity of Mabs, or antigen-binding fragments thereof, directed against human FPN1. Such an assay may be based on mature hepcidin-induced internalization and degradation of its receptor, FPN1. For instance, a HEK 293 stable cell line is prepared that allows for the inducible expression of FPN1. FPN1 is C-terminally fused with GFP for tracking purposes. The inducible expression of the FPN1-GFP molecule is controlled using the T-REx system (Invitrogen, Carlsbad, Calif.). The FPN1-GFP coding sequence is cloned into pcDNA4/TO vector, which contains an inducible promoter and a Zeocin resistance marker. The resulting construct is transfected into T-REx-293 cells which expresses the regulatory protein required for doxycycline inducible expression. Zeocin resistant clones are tested for the inducible expression of FPN-GFP. Cell growth conditions are essentially as described in the manufacturer's user manual for the T-REx System (Invitrogen). Briefly, cells are grown in DMEM, 10% dialyzed FBS, 20 μM FAC, plus 5 μg/mL penicillin-streptomycin. Selection is maintained with 100 μg/mL zeocin and 5 μg/mL blasticidin. Cells are plated onto 96-well black/clear plates that are coated with poly-D-lysine. An Acumen Explorer HTS, high resolution fluorescent plate reader is used for reading the total fluorescence per well.

Following trypsinization, 96-well assay plate is seeded with 9,000 cells/well using the FPN1-GFP/TREx 293 stable cell line. Seeding volume per well is 80 μL. Cells are allowed to attach overnight. Early the next morning, 9 μL of 30 ng/mL doxycyline is added to each well to induce FPN1-GFP expression. After 8 hours of induction at 37° C., the medium is aspirated and the wells are washed carefully with 150 μL/well of PBS.

The desired treatments (e.g., human hepcidin-25 and/or test antibodies) are set up in a 96-well format for quick addition to an assay plate after washing. Final assay volume per well is 45 μL Immediately after adding the treatments, the assay plate is read using the Acumen Explorer (set at 550 volts in channel 1). This reading is generally the 0 hour reading and is used to normalize for cell number per well, which correlates with the total fluorescence units (FLU) per well. For mature human hepcidin-induced internalization and degradation of FPN1, the maximum effect is seen at 0.5 μM mature human hepcidin. The $IC_{50}$ of mature human hepcidin is approximately 10 nM. For anti-FPN1 antibody neutralization assays, the human hepcidin-25 concentration is kept at 120 nM and the anti-FPN1 Mabs were tested at 600 nM, 200 nM, 67 nM, 22 nM, and 7.4 nM. The plates are incubated for 24 hours, after which, they are read again, and the data is generated as the ratio of total FLU per well at 24 hours divided by the total FLU per well at 0 hours. All data points are done in quadruplicate. The percent (%) inhibition is determined by subtracting the values for 120 nM mature human hepcidin treatment, and then dividing the FPN1 antibody treated values by the no human hepcidin-25 treated value.

In an in vitro assay conducted essentially as described above, human hepcidin-25 bioactivity was neutralized with various anti-FPN1 Mabs with a percent inhibition measured as shown in Table 8 below.

TABLE 8

Anti-FPN1 Mab Percent (%) Inhibition of Mature Human Hepcidin-induced Internalization and Degradation In Vitro

| | Mab 34A9 | Mab 1G9 | Mab 3D8 |
|---|---|---|---|
| Mab at 600 nM | 39.0% | 67.9% | 66.4% |
| Mab at 200 nM | 30.8% | 62.4% | 63.8% |
| Mab at 67 nM | 23.6% | 61.8% | 55.7% |
| Mab at 22 nM | 14.1% | 49.9% | 50.2% |
| Mab at 7.4 nM | 4.8% | 24.3% | 28.1% |

Data generated in experiments conducted essentially as described in Example 7 support the conclusion that Mabs 1G9, 34A9, and 3D8 greatly inhibit the ability of human hepcidin-25 to cause the internalization and degradation of human FPN1 in vitro.

EXAMPLE 8

Bioactivity of Mab 1G9 Relative to a Control Murine IgG1 following a Single Intravenous Dose to Cynomolgus Monkeys The physiological effects of anti-human FPN1 murine Mab 1G9 on serum hepcidin and serum iron levels were investigated by administering the Mab as a single intravenous dose to male Cynomolgus monkeys (*Macaca fascicularis*; 3-4 kg) and comparing its effects to a control administration of murine IgG1. Following administration blood samples were collected for analysis of serum iron and serum hepcidin. The dose (30 mg/kg) was administered as an injection via a saphenous vein. Immediately after dose administration, but before the needle was removed from the animal, the dose apparatus was flushed with approximately 2 mL of saline.

TABLE 9

| | | Concentration (mg/mL) | Volume (mL/kg) |
|---|---|---|---|
| 1 | Murine IgG1 Control | 9.53 | 3.15 |
| 2 | Murine 1G9 | 12.6 | 2.38 |

Sampling for Serum Hepcidin:

Blood was collected prior to dosing and at 0.5, 1, 3, 6, 10, 24, 48, 72, 96, and 168 hours post-dose. Blood (approximately 0.5 mL) was collected via a femoral vein into tubes containing no anticoagulant. Blood was allowed to clot under ambient conditions prior to centrifugation to obtain serum. Serum samples were placed on dry ice prior to storage at approximately −70° C.

Sampling for Serum Iron:

Blood was collected prior to dosing and at 1, 3, 6, 24, 48, 72, 96, and 168 hours post-dose. All blood samples were collected, handled, processed, stored, and analyzed in accordance with methods considered acceptable within the medical community. Serum iron levels may be measured by any method known in the art which is generally considered within the medical community to be an acceptable method of measuring total serum iron (Fe). Serum concentrations of hepcidin were determined by liquid chromatography-mass spectrometry essentially as described in Murphy, et al., Blood, 110:1048-54 (2007). Assays for measuring serum iron are well-known in the art (see, for example, Goodwin, J. F., et al., Clinical Chemistry 12: 47-57 (1966), and J. Clin. Path., 24:334-335 (1971)).

Serum hepcidin concentrations were unaffected by the administration of control murine IgG1 and ranged from 1.5 to 31 ng/mL over the time course studied. Average hepcidin levels in the control animals were 11.5±8.8 ng/mL (mean±SD). After administration of murine Mab 1G9, serum hepcidin levels were elevated from a baseline of 7.6 and 14.7 ng/mL to a peak of 49.7 and 79.1 ng/mL, respectively. The peak in serum hepcidin occurred approximately 10 hours after administration of the murine Mab 1G9 (FIG. 6). The elevation of serum hepcidin is likely due to the interaction of murine Mab 1G9 with its target FPN1, which, upon binding to FPN1 blocks the interaction of FPN1 and hepcidin, thereby slowing FPN1 clearance and/or internalization.

Serum iron was not elevated in animals treated with control murine IgG and ranged from 64 to 97 μg/dL over the time frame studied. After administration of murine Mab 1G9, serum iron levels were elevated from a baseline of 136 and 144 μg/dL to a peak of 306 and 292 μg/dL, respectively. The peak in serum iron occurred approximately 48 hrs after administration of murine Mab 1G9 (FIG. 7). Serum iron levels gradually returned to baseline by 96 hours after administration, indicating that the elevation of serum iron levels is irreversible.

EXAMPLE 9

Cell-Based Assay for Anti-FPN1 Antibody Inhibition of Hepcidin-25-Induced Internalization and Degradation Experiments conducted essentially as described in Example 7 above demonstrate that Mabs Combi-11, 4A10-3, and L2.2-4 inhibit human hepcidin-25 induced internalization and degradation of human FPN1 more effectively in vitro as compared with Mabs 34A9, 3D8, and 1G9 (see Table 10). More specifically, the anti-FPN1 Mabs were tested in a 9-point concentration curve starting at 900 nM and performing 3-fold serial dilutions. The percent (%) inhibition was determined by subtracting the values for 120 nM hepcidin treatment, and then dividing the Mab treated values by the no hepcidin treated value. Relative $IC_{50}$ were determined in Sigma Plot. Top percent (%) inhibition as well as relative and absolute $IC_{50}$ are shown in Table 10.

TABLE 10

| Mab (IgG4) | Top % Inhibition (n = 3) | Relative $IC_{50}$ (nM) (n = 3) | Absolute $IC_{50}$ (nM) (n = 3) |
|---|---|---|---|
| Combi11 | 92.6 ± 4.5 | 3.7 ± 0.2 | 3.8 ± 0.1 |
| 4A10-3 | 85.9 ± 2.2 | 4.7 ± 1.5 | 5.7 ± 1.7 |
| L2.2-4 | 81.6 ± 1.0 | 4.8 ± 1.2 | 6.2 ± 1.6 |
| 3D8 | 86.8 ± 7.0 | 10.2 ± 2.2 | 13.7 ± 3.4 |
| 1G9 | 69.0 ± 8.0 | 9.2 ± 3.3 | 18.8 ± 8.1 |
| 34A9 | 55.2 ± 7.1 | 58.9 ± 18.6 | N.C. |

N.C.: Fitted top of curve does not reach 50% so absolute $IC_{50}$ can not be calculated.

EXAMPLE 10

Pharmacodynamic Effect of Humanized Anti-Ferroportin Monoclonal Antibodies 4A10-3 in Cynomolgus Monkeys The pharmacodynamics of anti-ferroportin Mabs may be studied after administration of intravenous doses to male Cynomolgus monkeys according to methods known to those skilled in the art. For example, in five independent studies Mab 4A10-3 was administered to Cynomolgus monkeys as a single intravenous bolus (n=4/group) at doses of 0.3, 1.0, 3.0, 10 and 30 mg/kg. Blood samples (approximately 0.5 mL for iron parameters) were taken prior to the first dose and at 1, 6, 12, 24, 48, 72, 96, 168 and 264 hours post-dose. At higher dose levels, additional blood samples were taken at 360, 456, 552, and 648 hours post-dose. At the time of dosing, the animals weighed between 2 to 3 kg. Blood samples were collected from each animal via a femoral vein into tubes containing no anticoagulant.

Serum iron concentration-time profiles following intravenous administration of 0.3, 1.0, 3.0, 10 and 30 mg/kg Mab 4A10-3 to male Cynomolgus monkeys was associated with a dose dependent increase in serum iron which peaked at 24 hours after dosing. Peak iron responses (approximately 2-fold increase) and duration of response between the mg/kg and 30 mg/kg doses were similar. In the animals administered 0.3, 1.0, and 3.0 mg/kg doses serum iron returned to baseline values about 48 hours after dosing. In the animals administered 10 mg/kg and 30 mg/kg doses, serum iron returned to baseline values about 72 hours after dosing.

Furthermore, in a single study, administration of a single subcutaneous injection of Mab 4A10-3 at a dose of 10 mg/kg produced an identical response (n=2; mean±SD) in serum iron, in both intensity and duration, as observed after the equivalent intravenous dose (n=4; mean±SD).

EXAMPLE 11

Pharmacokinetics of Humanized Anti-Ferroportin Monoclonal Antibodies in Rats and Cynomolgus Monkeys The pharmacokinetics of anti-ferroportin Mabs may be studied in vivo according methods well-known to those skilled in the art. The pharmacokinetics of anti-FPN1 Mabs 4A10-3 and Combi 11 were investigated after single intravenous doses to male Cynomolgus monkeys and Sprague Dawley rats, for example. At the time of dosing the Cynomolgus monkeys used weighed between 2.2 and 5.5 kg and the Sprague Dawley rats weighed between 240 and 265 g.

The pharmacokinetic study conducted in Cynomolgus monkeys was performed in three phases, with doses at 1.0 mg/kg, 3.0 mg/kg, and 0.3 mg/kg administered at approximately 2 week intervals. At each phase, either Mab 4A10-3 or Mab Combi11 was administered as a single intravenous bolus (n=4 per group). Blood samples were taken prior to the first dose and at 1, 6, 12, 24, 48, 72, 96, 168, and 264 hours post-dose.

In rats, Mab 4A10-3 or Mab Combi 11 was administered as a single intravenous bolus dose of 3 mg/kg (n=3 per group). Serial blood samples were taken prior to dose and at 0.08, 1, 4, 8, 24, 48, 72, 120 and 168 hours post-dose.

Serum concentrations of Mabs 4A10-3 and Combi 11 were determined using a human IgG sandwich ELISA format. The standard curve range was 5 to 400 ng/mL, with a working lower limit of quantitation (LLOQ) defined as 10 ng/mL. Pharmacokinetic parameters were determined using non-compartmental analysis in WinNonlin version 5.2.

Serum concentration-time profiles following intravenous administration to male Cynomolgus monkeys are plotted in FIG. 10. Mab 4A10-3 was cleared much more slowly (approximately 5-fold) than Mab Combi11 at all doses studied. Differences were apparent at the first time point examined (1 hour) when serum concentrations of Mab Combi11 were approximately 50% of that observed for Mab 4A10-3. At 24 hours post-dose, serum concentrations of Mab 4A10-3 were 20-33% of Cmax compared to only 6-9% for Combi11. Peripheral concentrations of Mab Combi11 were not evident after the 0.3 mg/kg dose. The clearance of Mab 4A10-3 was somewhat faster at the two lower doses compared to the 3 mg/kg dose. The $T_{1/2}$ for Mab 4A10-3 ranged from 2 to 3 days. However, the $T_{1/2}$ for Mab Combi11 ranged from about 12 to about 27 hours.

The enhanced clearance of Mab Combi11 relative to Mab 4A10-3 was hypothesized to result from increased non-specific interactions of Mab Combi11 with cell surface proteins which do not occur for Mab 4A10-3. In order to evaluate this hypothesis the pharmacokinetics of Mab 4A10-3 and Mab Combi11 was studied in rats since neither Mab binds effectively to rat ferroportin.

Serum concentration-time profiles following intravenous administration to male rats are plotted in FIG. 11. Similar to the observation in primates, Mab 4A10-3 cleared more slowly (approximately 5-fold) than Mab Combi11 in rats (data not shown). Again, differences were apparent at the first time point examined (0.08 hours) when serum concentrations of Mab Combi11 were approximately 50% of that observed for Mab 4A10-3. The $T_{1/2}$ for Mab 4A10-3 and Mab Combi11 was approximately 4.5 days and 3 days, respectively, in rats (data not shown).

These data strongly suggest that the more rapid clearance observed for Mab Combi11 was not attributable to target receptor-mediated clearance since neither Mab 4A10-3 nor Mab Combi11 binds rat ferroportin.

EXAMPLE 12

Anti-Human FPN1 Mabs with Delayed Clearance and/or Low Non-Specific (Heparin) Binding The pharmacokinetic studies of Mab Combi11 described above in Example 11 suggested that Mab Combi11 was more rapidly cleared from serum as compared to Mab 4A10-3. The data also suggested that the more rapid clearance of Mab Combi11 as compared to Mab 4A10-3 was not attributable to increased target receptor-mediated clearance of Mab Combi11 relative to that of Mab 4A10-3.

Because multiple arginine residues had been introduced during the engineering of Mab Combi11, it was suspected that the resulting increase in positive charge of Mab Combi11 as compared with Mab 4A10-3, for example, resulted in increased undesirable non-specific binding to negatively-charged membrane surfaces and to heparin. Indeed, modeling of the structure of Mab Combi11 showed a strong positively-charged patch on the surface of Mab Combi11 which was more pronounced in Mab Combi11 than some of the other human engineered anti-FPN1 Mabs, including Mab 4A10-3 and Mab L2.2-4.

Mabs Combi11, 4A10-3, and L2.2-4 were tested for non-specific heparin binding using a heparin ELISA according to methods known to one skilled in the art. Mabs Combi11, 4A10-3, 3D8, and L2.2-4 were also tested for binding to human FPN1 expressing HEK 293 cells as well as to control HEK 293 cells lacking human FPN1 expressed on the cell surface.

The heparin ELISA using Mab Combi-11 showed that Mab Combi11 binds strongly to heparin whereas Mabs 4A10-3 and L2.2-4 did not. Furthermore, Mab Combi-11 also bound strongly to both human FPN1 expressing HEK 293 cells and control HEK 293 cells lacking human FPN1 expressed on the cell surface. On the other hand, Mabs 4A10-3, 3D8, and L2.2-4 significantly bound to human FPN1 expressing HEK 293 cells but not to the control HEK 293 cells.

Mab Com11GY was therefore generated to reduce the non-specific binding observed with Mab Combi11 by replacing the arginine amino acid residue in the HCDR2 with a glycine amino acid residue. In addition, another potentially problematic amino acid residue found in Mab Combi11, the tryptophan amino acid residue in the LCDR2, was substituted with a tyrosine amino acid residue in Mab Com11GY. Preliminary binding data, using supernatants from cells expressing Mabs Com11GY, demonstrated a lack of non-specific binding to control HEK 293 cells, i.e., human FPN1 non-expressing cells, whereas both Mabs 1B7 and 1F8 demonstrated significantly more non-specific binding to the same control cells.

EXAMPLE 13

Assay for the Inhibition of Human Hepcidin-25 Binding to FPN1

Human engineered, affinity matured anti-human FPN1 antibodies may be assayed for the ability to inhibit human hepcidin-25 binding to human FPN1 expressed in HEK 293 cells. Briefly, transfected FPN/293 cells are plated in poly-D-lysine coated plates on 96 well plates (BD Biosciences, San Jose, Calif.; BD Biocoat plates #35 4640) at 40,000 cells per well in 80 µL of assay medium (DMEM 11965, 10% dialyzed FBS, 20 µM FAC, penicillin-streptomycin), centrifuged for 1 minute at 1000 revolutions per minute, and then incubated 4 hours at 37° C., 10% $CO_2$. FPN1 expression is induced by adding 20 µL of Doxycycline at 10 nM to the plated cells (2 nM final concentration of doxycycline. Doxycyline induced and un-induced control cells are incubated for 5 hours at 37° C., 10% $CO_2$. Next, the inducing agent is removed by washing the plate 2× with DMEM. The cells are incubated overnight in 100 µL of assay medium. Next, the assay media is removed and replaced with 40 µL test antibody or an isotype control antibody solution in triplicate and incubated at 37° C., 10% $CO_2$ for 20 minutes. Next, 20 µL of biotinylated mature human hepcidin is added to the wells to a final concentration of 30 nM per well. The samples are incubated for 1 hour, at 37° C., 10% 10% $CO_2$ before washing 4 times with 200 µL 2% FBS, D-PBS (Gibco, catalog no. 14040). Next, 65 µL of lysing buffer (0.5% Triton X-100, 10 mM EDTA) are added to all the wells and the plates are shaken for 10 minutes. Next, 50 µL of the solution in each well is transferred to individual wells of a streptavidin coated Greiner microtiter plate (60 µL of 2 µg/mL streptavidin (Sigma, St. Louis, Mo.; catalog no. 54762) in PBS, incubated at 4° C. overnight, washed 2 times (0.1% Tween 20, TBS), blocked with casein/PBS), and then incubated for one hour at room temperature. Next, the wells of the plate are washed 3 times (0.1% Tween 20, TBS) and 50 µL anti-human hepcidin-25 Mab 3.23 at 0.5 µg/mL is added and the samples are incubated one hour at room temperature. The anti-human hepcidin-25 Mab 3.23 is described in PCT International Patent Application Publication WO 2009/058797. Next, the plates are washed three times and 50 µL of goat anti-human IgG-horseradish peroxidase (Southern Biotech catalog no. 2060-05) is added at 1:2000 dilution. After incubating one hour at room temperature, the plate is washed 4× and 50 µL of OPD substrate (Sigma; catalog no. P6912) is added. The reaction is stopped with 100 µL 1 N HCl after 4 minutes. Absorbance at 490 nm ($A_{490}$) is read using an appropriate ELISA plate reader. The assay range is determined by subtracting the $A_{490}$ of un-induced wells from the induced wells receiving control antibody.

The data shown in Table 11 demonstrate that humanized Mab 3D8 and affinity matured variants thereof significantly inhibit the ability of human hepcidin-25 to bind human FPN1. More specifically, Mab 3D8, a humanized form of the mouse Mab 1G9, having the human heavy chain framework VH1-69 and light chain framework O2, demonstrated an $IC_{50}$ of about 400 nM as determined in this assay format. Affinity matured Mabs 4A10-3, Combi11, and L2.2-4 demonstrated significantly improved inhibition of binding as determined in this assay format.

TABLE 11

| | | % Inhibition | | | | |
| --- | --- | --- | --- | --- | --- | --- |
| | | Antibody concentration | | | | |
| Antibody | | 2000 nM | 500 nM | 125 nM | 31.25 nM | 7.8 nM |
| 3D8 | Mean | 54.7 | 64.7 | 21.8 | 4.0 | −2.8 |
| | SD | 9.0 | 2.5 | 14.9 | 11.5 | 2.7 |
| 4A10-3 | Mean | 95.3 | 84.9 | 59.3 | 13.4 | 5.4 |
| | SD | 2.1 | 1.7 | 6.4 | 4.2 | 14.4 |
| combi 11 | Mean | 79.9 | 81.6 | 88.4 | 32.1 | 18.7 |
| | SD | 9.0 | 8.8 | 4.8 | 3.1 | 8.4 |
| L2.2-4 | Mean | 85.1 | 99.8 | 76.5 | 27.5 | −0.1 |
| | SD | 20.8 | 6.5 | 9.3 | 3.9 | 2.9 |
| control IgG | Mean | −2.5 | −0.7 | 1.9 | 7.9 | 2.5 |
| | SD | 5.8 | 10.3 | 6.2 | 6.5 | 14.1 |

Note:
75 kg/mole was the molecular weight used to calculate the antibody concentration.

EXAMPLE 14

In Vitro Assay of the Effects of FPN1 Mabs on Cellular Ferritin Levels

As described in Example 5, Caco-2 cells, a human enterocyte cell line, endogenously expressing FPN1, may be monitored for changes in ferritin. In experiments conducted essentially as described in Example 5, the effect of anti-human FPN1 antibodies on mature hepcidin modulated iron regulation in Caco-2 cells was determined and is expressed as percent inhibition, averaged over a number of independent experiments in Table 12 below.

The data indicate that the effects of hepcidin on ferritin concentration in the cells can be inhibited by anti-human FPN1 Mabs in a dose-dependent manner. As indicated by the EC50 values, some anti-human Mabs are more potent in inhibiting the effect of hepcidin than others, for example, Combi11≅4A10-3>L2-2-4>3D8.

TABLE 12

Percentage inhibition (± SEM) by anti-human FPN1 Mabs on mature hepcidin induced increases in cellular ferritin levels in Caco-2 cells in vitro

| Concentration (M) | Combi11 | 4A10-3 | L2-2-4 | 3D8 | Control human IgG$_4$ |
|---|---|---|---|---|---|
| 6.67E−7M | 75.2 (7.4) | 61.9 (6.3) | 61.7 (3.9) | 29.8 (6.1) | 18.7 (3.8) |
| 2.22E−7M | 69.3 (6.2) | 59.6 (5.4) | 53.8 (11.7) | 25.2 (4.4) | 24.2 (5.2) |
| 7.4E−8M | 61.1 (5.6) | 45.6 (5.1) | 40.6 (10.3) | 12.0 (5.6) | 21.1 (4.4) |
| 2.47E−8M | 45.3 (6.5) | 36.2 (8.1) | 30.1 (4.4) | 3.4 (4.7) | 22.1 (3.8) |
| 8.0E−9M | 31.6 (9.1) | 28.0 (7.5) | 39.5 (6.3) | 14.9 (3.6) | 16.1 (3.7) |
| 2.7E−9M | 34.8 (5.7) | 24.9 (7.6) | 39.6 (7.5) | 10.6 (10.6) | 22.4 (3.6) |
| 9.0E−10M | 23.3 (6.3) | 19.5 (4.8) | 24.4 (8.2) | 8.6 (6.4) | 17.5 (3.9) |
| 3.0E−10M | 14.2 (5.6) | 12.0 (10.6) | 24.1 (9.8) | 7.3 (6.6) | 15.5 (3.2) |
| Number of experiments (n) | 6 | 6 | 3 | 4 | 16 |
| EC50 (nM) | 28 | 37 | 193 | 360 | N.C. |

N.C.: Negative control EC$_{50}$ can not be calculated.

We claim:

1. A monoclonal antibody comprising:
   a. the light chain and the heavy chain as shown in SEQ ID NO: 154 and SEQ ID NO: 152, respectively;
   b. the light chain and the heavy chain as shown in SEQ ID NO: 181 and SEQ ID NO: 179, respectively; or
   c. the light chain and the heavy chain as shown in SEQ ID NO: 158 and SEQ ID NO: 156, respectively.

2. The monoclonal antibody of claim 1 comprising two light chain polypeptides and two heavy chain polypeptides, and wherein each of the light chain polypeptides have the amino acid sequence as shown in SEQ ID NO: 154 and each of the heavy chain polypeptides have the amino acid sequence as shown in SEQ ID NO: 152.

3. The monoclonal antibody of claim 1 comprising two light chain polypeptides and two heavy chain polypeptides, and wherein each of the light chain polypeptides have the amino acid sequence as shown in SEQ ID NO: 181 and each of the heavy chain polypeptides have the amino acid sequence as shown in SEQ ID NO: 179.

4. The monoclonal antibody of claim 1 comprising two light chain polypeptides and two heavy chain polypeptides, and wherein each of the light chain polypeptides have the amino acid sequence as shown in SEQ ID NO: 158 and each of the heavy chain polypeptides have the amino acid sequence as shown in SEQ ID NO: 156.

5. A pharmaceutical composition, comprising the monoclonal antibody of claim 1, and a pharmaceutically acceptable carrier, diluent, or excipient.

6. A monoclonal antibody obtained by a process comprising the steps of:

a. transforming a host cell with a recombinant expression vector comprising a nucleotide sequence encoding the light chain polypeptide as shown in SEQ ID NO: 154 and a nucleotide sequence encoding the heavy chain polypeptide as shown in SEQ ID NO: 152;

b. culturing said host cell under conditions suitable to allow expression of the monoclonal antibody; and c. recovering the expressed monoclonal antibody.

7. The monoclonal antibody of claim 6 wherein the host cell is a Chinese hamster ovary (CHO), NS0 myeloma, COS, or SP2/0 cell.

* * * * *